(12) United States Patent
Yamazaki et al.

(10) Patent No.: US 9,241,488 B2
(45) Date of Patent: Jan. 26, 2016

(54) AZOLE DERIVATIVE, METHOD FOR PRODUCING AZOLE DERIVATIVE, AND INTERMEDIATE COMPOUND

(75) Inventors: Toru Yamazaki, Tokyo (JP); Emiko Obata, Tokyo (JP); Taiji Miyake, Tokyo (JP); Hisashi Kanno, Tokyo (JP)

(73) Assignee: KUREHA CORPORATION, Tokyo (JP)

( * ) Notice: Subject to any disclaimer, the term of this patent is extended or adjusted under 35 U.S.C. 154(b) by 49 days.

(21) Appl. No.: 14/124,033

(22) PCT Filed: Jun. 6, 2012

(86) PCT No.: PCT/JP2012/064605
§ 371 (c)(1),
(2), (4) Date: Dec. 5, 2013

(87) PCT Pub. No.: WO2012/169559
PCT Pub. Date: Dec. 13, 2012

(65) Prior Publication Data
US 2014/0113815 A1     Apr. 24, 2014

(30) Foreign Application Priority Data

Jun. 7, 2011  (JP) ................. 2011-126817
Jan. 6, 2012  (JP) ................. 2012-001476

(51) Int. Cl.
| C07D 405/06 | (2006.01) |
| A01N 43/653 | (2006.01) |
| A01P 3/00 | (2006.01) |
| C07D 249/08 | (2006.01) |
| C07D 319/08 | (2006.01) |
| A01N 43/50 | (2006.01) |

(52) U.S. Cl.
CPC ............ *A01N 43/653* (2013.01); *A01N 43/50* (2013.01); *C07D 249/08* (2013.01); *C07D 319/08* (2013.01); *C07D 405/06* (2013.01)

(58) Field of Classification Search
None
See application file for complete search history.

(56) References Cited

U.S. PATENT DOCUMENTS

| 4,938,792 A | 7/1990 | Kumazawa et al. |
| 5,028,254 A | 7/1991 | Kumazawa et al. |
| 5,159,118 A | 10/1992 | Kumazawa et al. |
| 5,239,089 A | 8/1993 | Kumazawa et al. |
| 5,256,683 A | 10/1993 | Hutt et al. |
| 5,292,764 A | 3/1994 | Arahira et al. |
| 5,380,743 A | 1/1995 | Hutt et al. |
| 5,414,105 A | 5/1995 | Kumazawa et al. |
| 5,504,096 A | 4/1996 | Arahira et al. |
| 5,639,918 A | 6/1997 | Butt et al. |
| 2014/0128611 A1 | 5/2014 | Sunagawa et al. |
| 2014/0179517 A1 | 6/2014 | Araki et al. |

FOREIGN PATENT DOCUMENTS

| CN | 1030232 A | 1/1989 |
| CN | 1044814 A | 8/1990 |
| CN | 103562187 A | 2/2014 |
| CN | 103764636 A | 4/2014 |
| DE | 3902031 A1 | 7/1990 |
| EP | 0329397 A1 | 8/1989 |
| JP | 1-93574 A | 4/1989 |
| JP | 1-186871 A | 7/1989 |
| JP | 1-301664 A | 12/1989 |
| JP | 2-42003 A | 2/1990 |
| JP | 2-237979 A | 9/1990 |
| JP | 5-271197 A | 10/1993 |
| JP | 3138055 B2 | 12/2000 |
| WO | WO 2009/088070 A1 | 7/2009 |
| WO | WO 2010/023862 A1 | 3/2010 |
| WO | WO 2010/122171 A1 | 10/2010 |
| WO | WO 2011/070771 A1 | 6/2011 |
| WO | WO 2011070771 A1 * | 6/2011 ........... C07D 233/60 |

OTHER PUBLICATIONS

PCT/ISA/210—International Search Report mailed on Jul. 31, 2012, issued in PCT/JP2012/064605.
PCT/ISA/237—mailed on Jul. 31, 2012, issued in PCT/JP2012/064605.
Extended European Search Report issued Sep. 22, 2014, in European Patent Application No. 12796434.4.
Notification of First Office Action issued Dec. 2, 2014, in Chinese Patent Application No. 201280028080.0, with English translation.
Srinivas et al., "A Mild and Efficient Bisaldolization of Ketones and its Application towards Spirocyclic 1,3-Dioxanes and Novel 1,3,5-Trioxocanes," SYNLETT (2009) No. x, pp. 1346-1350.
English translation of International Preliminary Report on Patentability and Written Opinion issued Dec. 27, 2013, in PCT International Application No. PCT/JP2012/064605.
Japanese Office Action, issued Jul. 28, 2015, for Japanese Application No. 2013-519518, along with an English translation.
Second Office Action, dated May 20, 2015, issued in Chinese Patent Application No. 201280028080.0, with English translation.
European Office Action for Application No. 12796434.4 dated Jul. 9, 2015.

* cited by examiner

*Primary Examiner* — Mina Haghighatian
*Assistant Examiner* — Erin Hirt
(74) *Attorney, Agent, or Firm* — Birch, Stewart, Kolasch & Birch, LLP

(57) ABSTRACT

In order to provide a novel azole derivative, an azole derivative of the present invention is an azole derivative represented by a general formula (V'). (where $R^6$ and $R^7$ independently represent a hydrogen atom, a $C_1$-$C_4$ alkyl group, a phenyl group, or a benzyl group; X represents a halogen atom, a $C_1$-$C_4$ alkyl group, a haloalkyl group, an alkoxy group or a haloalkoxy group, a phenyl group, a cyano group, or a nitro group; m represents an integer of 0 to 5; and A represents a nitrogen atom or a methyne group.)

13 Claims, No Drawings

AZOLE DERIVATIVE, METHOD FOR PRODUCING AZOLE DERIVATIVE, AND INTERMEDIATE COMPOUND

TECHNICAL FIELD

The present invention relates to a novel azole derivative, a method for producing the same, a method for using the same, and an intermediate compound thereof.

BACKGROUND ART

It is known that certain kinds of 2-substituted-5-benzyl-1-azolylmethylcyclopentanol derivative show biocidal activities (e.g., see Patent Literatures 1 and 2).

Further, it is reported that some compounds encompassed in 2-(halogenated alkyl hydrocarbon)-5-benzyl-1-azolylmethylcyclopentanol derivative show an anticonvulsive property and an anti-anxiety fighting activity (see Patent Literature 3). Note that Patent Literature 3 does not disclose agro-horticultural agents or industrial material protecting agents, and does not specifically disclose compounds that are encompassed in the scope of the present invention.

CITATION LIST

Patent Literature 1
Japanese Patent Application Publication, Tokukaihei, No. 01-93574 A
Patent Literature 2
Japanese Patent Application Publication, Tokukaihei, No. 01-186871 A
Patent Literature 3
German Patent Application Publication, No. 3902031, specification
Patent Literature 4
Japanese Patent Application Publication, Tokukaihei, No. 05-271197 A
Patent Literature 5
Japanese Patent Application Publication, Tokukaihei, No. 01-301664 A

SUMMARY OF INVENTION

Technical Problem

Conventionally, an agro-horticultural pesticide having a low toxicity to humans, capable of being handled safely, and exhibiting a high controlling effect on a wide range of plant diseases has been desired. Also, there has been a need for a plant growth regulator which regulates the growth of a variety of crops and horticultural plants thereby exhibiting yield-increasing effects and quality-improving effects, or for an industrial material protecting agent which protects an industrial material from a wide range of hazardous microorganisms which invade such materials.

A main object of the present invention is to provide a compound and a method for producing the same which can be used to produce an agro-horticultural agent and an industrial material protecting agent which fulfill the need described above.

Solution to Problem

In order to attain the object, an azole derivative in accordance with the present invention is an azole derivative represented by the following general formula (V').

[Chem. 1]

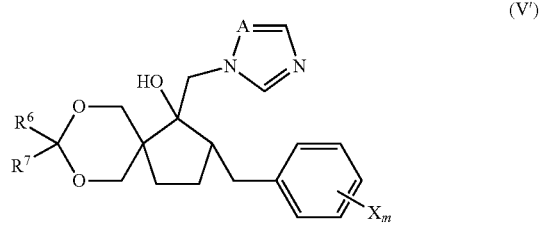

(where, $R^6$ and $R^7$ independently represent a hydrogen atom, a $C_1$-$C_4$ alkyl group, a phenyl group, or a benzyl group, and one or more hydrogen atoms of the phenyl group and one or more hydrogen atoms in a phenyl part of the benzyl group may be substituted with a $C_1$-$C_4$ alkyl group, a $C_1$-$C_4$ alkoxy group, or a halogen atom; X represents a halogen atom, a $C_1$-$C_4$ alkyl group, a $C_1$-$C_4$ haloalkyl group, a $C_1$-$C_4$ alkoxy group, a $C_1$-$C_4$ haloalkoxy group, a phenyl group, a cyano group, or a nitro group; m represents an integer of 0 to 5, and a plurality of Xs may be different from each other in the case where m is 2 or more; and A represents a nitrogen atom or a methyne group.)

Further, in order to attain the object, a first aspect of a method for producing an azole derivative in accordance with the present invention is a method for producing the above azole derivative, and the method includes the step of: reacting a compound represented by the following general formula (VII'), which compound has been obtained by converting a compound represented by the following general formula (VIII') into an oxirane, with a compound represented by the following general formula (VI) in order to obtain an azole derivative represented by the general formula (V').

[Chem. 2]

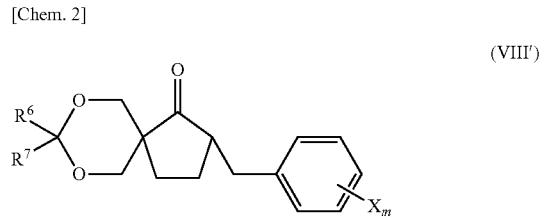

(where $R^6$, $R^7$, X, and m in the formula (VIII') are identical with those in the formula (V'), respectively.)

[Chem. 3]

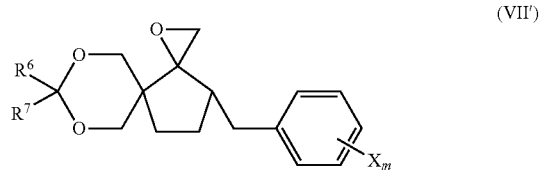

(where $R^6$, $R^7$, X, and m in the formula (VII') are identical with those in the formula (V'), respectively.)

[Chem. 4]

(where M represents a hydrogen atom or an alkalin metal, and A in the formula (VI) is identical with that in the formula (V').)

Further, in order to attain the object, a second aspect of a method for producing an azole derivative in accordance with the present invention is a method for producing the above azole derivative represented by the following general formula (IV'), and the method includes the step of: reacting the azole derivative recited in claim 1 in the presence of an acid, in order to obtain the azole derivative represented by the following general formula (IV').

[Chem. 5]

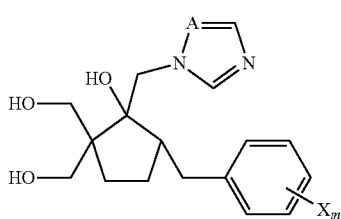

(IV')

(where X, m, and A in the formula (IV') are identical with those in the formula (V'), respectively.)

Further, in order to attain the object, a first aspect of an intermediate compound in accordance with the present invention is an intermediate compound represented by the following general formula (VIII'), the intermediate compound being used for producing the above azole derivative (V').

[Chem. 6]

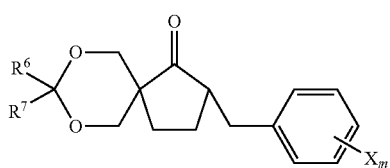

(VIII')

(where $R^6$, $R^7$, X, and m in the formula (VIII') are identical with those in the formula (V), respectively.)

Further, in order to attain the object, a second aspect of an intermediate compound in accordance with the present invention is an intermediate compound represented by the following general formula (IX'), the intermediate compound being used for producing the above azole derivative (V').

[Chem. 7]

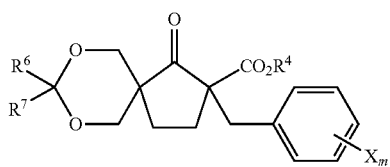

(IX')

(where $R^6$, $R^7$, X, and m in the formula (IX') are identical with those in the formula (V'), respectively, and $R^4$ represents a $C_1$-$C_4$ alkyl group.)

Further, an azole derivative represented by the following general formula (Ia'), the azole derivative being produced by the above is also encompassed in the scope of the present invention.

[Chem. 8]

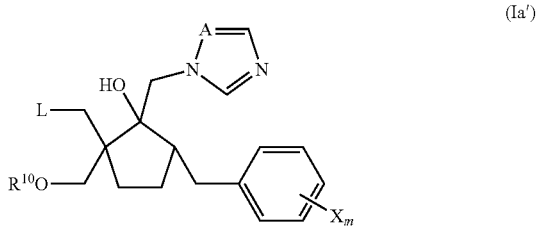

(Ia')

(where $R^{10}$ represents a $C_1$-$C_3$ alkyl group, L represents a halogen atom, and X, m, A in the formula (Ia') are identical with those in the formula (V'), respectively.)

Note that an agro-horticultural agent or an industrial material protecting agent containing as an active ingredient an azole derivative in accordance with the present invention is also encompassed in the scope of the present invention.

In the present specification etc., identical functional groups (or atoms) in general formulae are denoted by identical symbols and the detailed description thereof is omitted appropriately. For example, $R^1$ shown in a general formula (I) is identical with $R^1$ shown in a different general formula. As a matter of course, in addition to $R^1$, the same applies to other functional groups (or atoms).

Advantageous Effects of Invention

An azole derivative and a method for producing an azole derivative in accordance with the present invention make it possible to obtain, with a good yield, an intermediate compound of a compound having a biocidal activity.

DESCRIPTION OF EMBODIMENTS

The following description will discuss favorable embodiments for implementing the present invention. Note that Embodiments described below are merely examples of typical embodiments of the present invention, so that the scope of the present invention should not be limited by such embodiments.

[1. Azole Derivative]

The inventors of the present invention studied chemical structures and biological activities of a large number of azole derivatives in detail. As a result, the inventors found that an azole derivative (specifically, 2-substituted alkyl-2-haloalkyl-5-benzyl-1-azolylmethylcyclopentanol) represented by the following general formula (I) had an excellent activity. First, the following description will discuss an azole derivative (hereinafter, referred to as "Compound (I)") represented by the following general formula (I) in accordance with the present invention. Compound (I) has, at position 2 of a cyclopentane ring, a hydrocarbon substituent group in which a hydrogen atom(s) is/are substituted by a halogen atom(s). Compound (I) is a novel compound that any literatures do not disclose.

[Chem. 9]

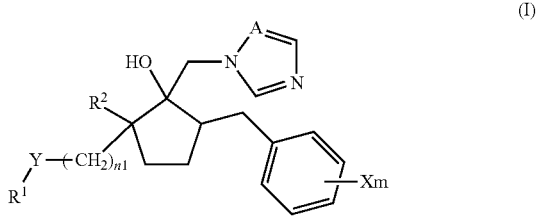

(I)

The following description will discuss specific examples of symbols ($R^1$, $R^2$, X, m, A, Y, and n1) of Compound (I).

(1) $R^1$—Y—$(CH_2)_{n1}$

First, the following description will be discussed on the assumption that $R^1$—Y—$(CH_2)_{n1}$, which is attached to a carbon atom to which $R^2$ (described below) is also attached, in Compound (I) is regarded as a single functional group.

(1-1) $R^1$ $R^1$ represents a hydrogen atom or a $C_1$-$C_3$ alkyl group. In the case where $R^1$ represents a $C_1$-$C_3$ alkyl group, specific examples of $R^1$ encompass a methyl group, an ethyl group, a (1-methyl)ethyl group, and an n-propyl group. Among them, a methyl group and an ethyl group are preferable.

(1-2) Y and n1

Y represents an oxygen atom, a sulfur atom, or $NR^3$. Further, n1 represents 1 or 2. Note that $R^3$ represents a hydrogen atom or a $C_1$-$C_3$ alkyl group.

In the case where Y represents an oxygen atom, specific examples of $R^1$—Y—$(CH_2)_{n1}$ encompass methoxymethyl group, ethoxymethyl group, propoxymethyl group, methoxyethyl group, ethoxyethyl group, and propoxyethyl group.

In the case where Y represents a sulfur atom, specific examples of $R^1$—Y—$(CH_2)_{n1}$ encompass methylsulfanylmethyl group, ethylsulfanylmethyl group, propylsulfanylmethyl group, methylsulfanylethyl group, propylsulfanylethyl group, and propylsulfanylpropyl group.

In the case where Y represents $NR^3$, specific examples of $R^1$—Y—$(CH_2)_{n1}$ encompass methylaminomethyl group, ethylaminomethyl group, propylaminomethyl group, methylaminoethyl group, ethylaminoethyl group, propylaminoethyl group, (dimethylamino)methyl group, (ethylmethylamino)methyl group, (methylpropylamino)methyl group, (diethylamino)methyl group, (ethylmethylamino)methyl group, (ethylpropylamino)methyl group, (dipropylamino)methyl group, (dimethylamino)ethyl group, (ethylmethylamino)ethyl group, (methylpropylamino)ethyl group, (diethylamino)ethyl group, (ethylmethylamino)ethyl group, (ethylpropylamino)ethyl group, and (dipropylamino)ethyl group.

Among them, Y preferably represents an oxygen atom, n1 preferably represents 1. That is, $R^1$—Y—$(CH_2)_{n1}$ preferably represents a methoxymethyl group or an ethoxymethyl group.

(2) $R^2$

The following description will discuss $R^2$ in detail. $R^2$ represents, for example, a haloalkyl group. The term "haloalkyl group" in the present specification etc. means a functional group in which at least one hydrogen atom of an alkyl group is substituted by a halogen atom.

$R^2$ preferably represents a haloalkyl group having a $C_1$-$C_4$ alkyl chain. The alkyl chain may be a linear or branched. Further, $R^2$ preferably represents a haloalkyl group in which a hydrogen atom to be attached to a carbon atom positioned at an end of an alkyl chain is substituted by a halogen atom. That is, $R^2$ preferably represents a haloalkyl group represented by a general formula $(CH_2)_{n3}CH_{3-q}Z_q$. In the general formula, n3 represents 0 to 3, and q represents 1 to 3. Z represents a halogen atom. Specific examples of Z encompass a chlorine atom, a fluorine atom, a bromine atom, and an iodine atom.

More specifically, examples of $R^2$ encompass chloromethyl group, dichloromethyl group, trichloromethyl group, 2-chloroethyl group, 1-chloroethyl group, 2,2-dichloroethyl group, 1,2-dichloroethyl group, 2,2,2-trichloroethyl group, 3-chloropropyl group, 2,3-dichloropropyl group, 1-chloro-1-methylethyl group, 2-chloro-1-methylethyl group, 2-chloropropyl group, 4-chlorobutyl group, 5-chloropentyl group, fluoromethyl group, difluoromethyl group, trifluoromethyl group, 2-fluoroethyl group, 1-fluoroethyl group, 2,2-difluoroethyl group, 1,2-difluoroethyl group, 2,2,2-trifluoroethyl group, 3-fluoropropyl group, 2,3-difluoropropyl group, 1-fluoro-1-methylethyl group, 2-fluoro-1-methylethyl group, 2-fluoropropyl group, 3,3,3-trifluoropropyl group, 2,2,3,3-tetrafluoropropyl group, 2,2,3,3,3-pentafluoropropyl group, 4-fluorobutyl group, 5-fluoropentyl group, bromomethyl group, dibromomethyl group, tribromomethyl group, 2-bromoethyl group, 1-bromoethyl group, 2,2-dibromoethyl group, 1,2-dibromoethyl group, 2,2,2-tribromoethyl group, 3-bromopropyl group, 2,3-dibromopropyl group, 1-bromo-1-methylethyl group, 2-bromo-1-methylethyl group, 2-bromopropyl group, 4-bromobutyl group, 5-bromopentyl group, iodomethyl group, diiodomethyl group, 2-iodoethyl group, 1-iodoethyl group, 2,2-diiodoethyl group, 1,2-diiodoethyl group, 2,2,2-triiodoethyl group, 3-iodopropyl group, 2,3-diiodopropyl group, 1-iodo-1-methylethyl group, 2-iodo-1-methylethyl group, 2-iodopropyl group, and 4-iodobutyl group. Among them, $R^2$ preferably represents a chloromethyl group.

(3) X and m

The following substituents are examples of X.

Halogen atom: specifically, a chlorine atom, a fluorine atom, a bromine atom, and an iodine atom.

$C_1$-$C_4$ alkyl group: specifically, a methyl group, an ethyl group, an n-propyl group, a 1-methylethyl group, a 2-methylpropyl group, an n-butyl group, a 1,1-dimethylethyl group, and the like.

$C_1$-$C_4$ haloalkyl group: specifically, a trifluoromethyl group, a 1,1,2,2,2-pentafluoroethyl group, a chloromethyl group, a trichloromethyl group, a bromomethyl group, and the like.

$C_1$-$C_4$ alkoxy group: specifically, a methoxy group, an ethoxy group, an n-propoxy group, and the like.

$C_1$-$C_4$ haloalkoxy group: specifically, a trifluoromethoxy group, a difluoromethoxy group, a 1,1,2,2,2-pentafluoroethoxy group, a 2,2,2-trifluoroethoxy group, and the like.

Note that X may be a phenyl group, a cyano group, or a nitro group.

X preferably represents a halogen atom, a $C_1$-$C_3$ haloalkyl group, a $C_1$-$C_3$ haloalkoxy group, a $C_1$-$C_3$ alkyl group, or a $C_1$-$C_3$ alkoxy group, and particularly preferably represents a halogen atom, a $C_1$-$C_2$ haloalkyl group, or a $C_1$-$C_2$ haloalkoxy group.

The symbol m is an integer of 0 to 5. In the case where m is 2 or more, a plurality of Xs may be identical with or different from each other. Here, m preferably represents an integer of 0 to 3, and more preferably an integer of 0 to 2.

(4) A

A is a nitrogen atom or a methyne group. A preferably represents a nitrogen atom.

(5) Stereoisomer

Compound (I) has stereoisomers (Type C and Type T) which are represented by the following general formulae (CC), (TT), (CT), and (TC). Compound (I) may be any one of isomers, or a mixture thereof. Note that, in the following general formulae, in a case where a hydroxy group at position 1 and a haloalkyl group ($R^2$) at position 2 are in a cis position and a hydroxy group at position 1 and a benzyl group at position 5 are in a cis position, a relative configuration is (CC). Further, although a hydroxy group at position 1 and a haloalkyl group ($R^2$) at position 2 are in a trans position and a hydroxy group at position 1 and a benzyl group at position 5 are in a trans position, a relative configuration is (TT). Furthermore, although a hydroxy group at position 1 and a haloalkyl group ($R^2$) at position 2 are in a cis position and a hydroxy group at position 1 and a benzyl group at position 5 are in a trans position, a relative configuration (CT). Still further, although a hydroxy group at position 1 and a haloalkyl group ($R^2$) at position 2 are in a trans position and a hydroxy group at position 1 and a benzyl group at position 5 are in a cis position, a relative configuration is (TC). Note that, in this specification, a position of a carbon to which a hydroxy group is attached is defined as a position 1 of a cyclopentane ring.

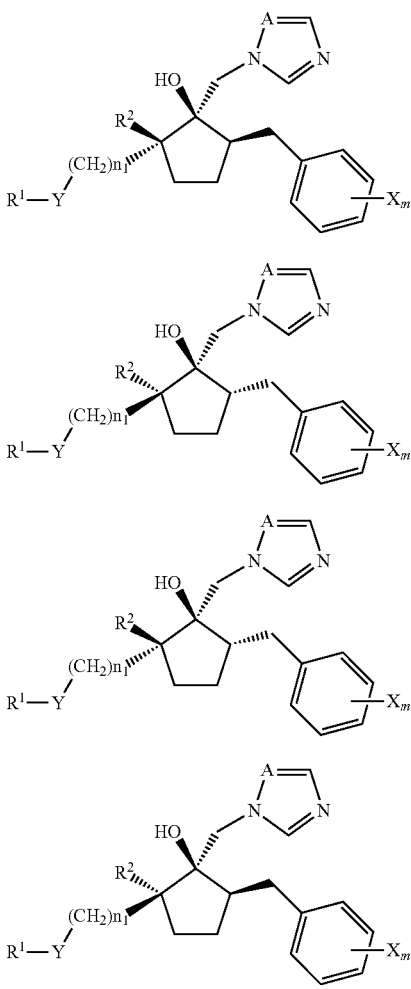

CC

TT

CT

TC

An azole derivative of the present invention has an excellent biocidal effect on a wide range of microorganisms which are pathogenic to plants. Therefore, an agro-horticultural agent containing the azole derivative of the present invention as an active ingredient can advantageously exhibit a high controlling effect on a wide range of plant diseases.

Moreover, the agro-horticultural agent containing the azole derivative of the present invention as an active ingredient can advantageously regulate the growth of a variety of crops and horticultural plants thereby increasing their yields while improving their qualities.

An industrial material protecting agent containing the azole derivative of the present invention as an active ingredient can further advantageously protect an industrial material from a wide range of hazardous microorganisms which invade such materials.

2. Methods for Producing Azole Derivatives

A method for producing an azole derivative referred to as Compound (I) will be described below. Solvents, bases, acids, and the like employed in each Step in the production method according to the invention may be those listed below unless otherwise specified.

(1) Solvents

A solvent employed is not particularly limited provided that the solvent does not affect any reaction. Examples of the solvent generally encompass: ethers such as diethyl ether, tetrahydrofuran (hereinafter, also referred to as "THF"), and dioxane; alcohols such as methanol, ethanol, and isopropanol; aromatic hydrocarbons such as benzene, toluene, and xylene; aliphatic hydrocarbons such as petroleum ether, hexane, and methylcyclohexane; and amides such as N,N-dimethylformamide (hereinafter, also referred to as "DMF"), N,N-dimethylacetamide, and N-methyl-2-pyrrolidinone. In addition, for example, water, acetonitrile, ethyl acetate, acetic anhydride, acetic acid, pyridine, and dimethyl sulfoxide may be also used as the solvent. Two or more of these solvents may be used in combination.

Exemplified as a solvent is a solvent composition consisting of solvents which do not form a homogenous layer with each other. In this case, a phase transfer catalyst such as customary quaternary ammonium salt or crown ether may be added to the reaction system.

(2) Bases and Acids

A base or an acid may be added to the solvent described above.

A base employed is not particularly limited. Examples of the base encompass: a carbonate of an alkaline metal such as sodium carbonate, sodium hydrogen carbonate, potassium carbonate, and potassium hydrogen carbonate; a carbonate of an alkaline earth metal such as calcium carbonate and barium carbonate; a hydroxide of an alkaline metal such as sodium hydroxide and potassium hydroxide; an alkaline metal such as lithium, sodium, and potassium; an alkoxide of an alkaline metal such as sodium methoxide, sodium ethoxide, and potassium t-butoxide; an alkaline metal hydride such as sodium hydride, potassium hydride, and lithium hydride; an organometallic compound of an alkaline metal such as n-butyl lithium; an alkaline metal amide such as lithium diisopropyl amide; and an organic amine such as triethylamine, pyridine, 4-dimethylaminopyridine, N,N-dimethylaniline, and 1,8-diazabicyclo-7-[5.4.0]undecene.

An acid employed is not particularly limited. Examples of the acid encompass: an inorganic acid such as hydrochloric acid, hydrobromic acid, hydroiodic acid, and sulfuric acid; an organic acid such as formic acid, acetic acid, butyric acid, trifluoroacetic acid, and p-toluenesulfonic acid; a Lewis acid such as lithium chloride, lithium bromide, rhodium chloride, aluminum chloride, and boron trifluoride.

(3) First Method for Producing Compound (I)

(3-1) Step 1A

The following description will discuss a first method for producing azole derivatives in accordance with the present invention.

Among the azole derivatives of the present invention, a method for producing the following Compound (Ia) will be described in Step 1A.

[Chem. 11]

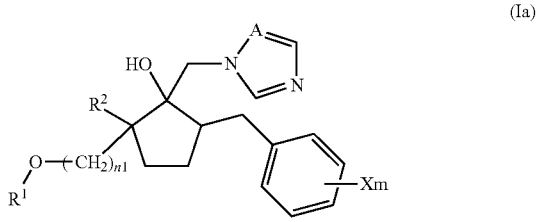

(Ia)

where $R^1$, $R^2$, X, m, A, and n1 are as having been already described above.

One embodiment of the method includes the steps of alkylating a hydroxy group of a compound represented by the following general formula (IIIa) in order to obtain Compound (IIa), and opening, with use of an arbitrary halogen acid, a heterocycle in Compound (IIa), which heterocycle contains an oxygen atom, in order to obtain Compound (Ia).

This embodiment will exemplify a step of alkylating a hydroxyalkyl group of a compound represented by the following general formula (IIIa), which compound has a hydroxyalkyl group at position 2 of a cyclopentane ring, and subjecting the resultant compound to ring opening (Step 1A; see a reaction formula (1)).

Note that the compound represented by the general formula (Ia) is a compound having a haloalkyl group at position 2 of a cyclopentane ring. Hereinafter, a compound represented by the general formula α is referred to as "Compound α". For example, the compound represented by the general formula (Ia) is referred to as "Compound (Ia)".

Reaction formula (1)

[Chem. 12]

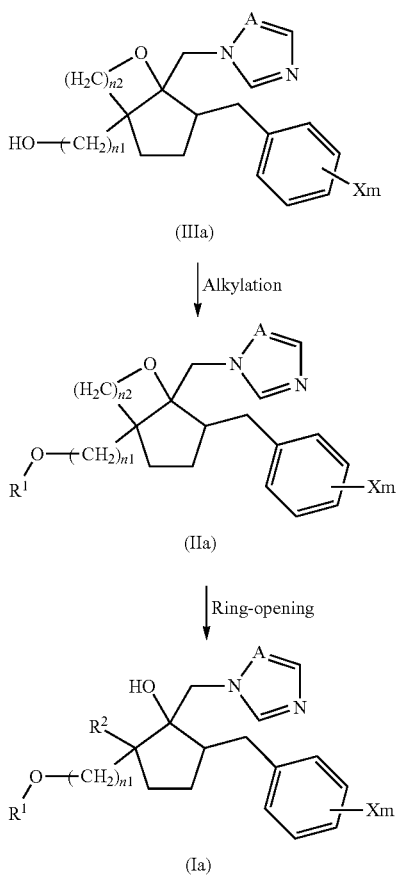

where $R^1$, $R^2$, X, m, A, and n1 are as having been already described above. n2 represents the number of carbons of an alkyl group in $R^2$.

(3-1-1) Step 1A1 (Alkylating Step)

The following description will discuss a step (Step 1A1) of alkylating Compound (IIIa) in Step 1A in order to obtain Compound (IIa).

A method for performing alkylation to obtain Compound (IIa) is not particularly limited. For example, the alkylation can be performed such that metalalkoxide, prepared from a hydroxy group of Compound (IIIa) and alkaline metal base, is reacted in a solvent with alkyl having a leaving group at a room temperature.

Examples of the solvent encompass: ether solvents such as THF; solvents of amides such as N-methylpyrrolidone (NMP), N,N-dimethylformamide (DMF), and N,N-dimethylacetamide; aromatic solvents such as benzene and toluene; and halide solvents such as methylene chloride. Among them, THF can be more preferably used.

Examples of the alkyl having a leaving group encompass: alkyl halide such as iodide and bromide; and sulfonic acid ester such as tosyloxyalkyl and mesyloxyalkyl. Among them, alkyl iodides can be preferably used. Further, among the alkyl iodides, a methyl iodide is more preferably used.

Examples of alkaline metal base encompass sodium, sodium hydride, sodium hydroxide, and potassium hydroxide. Among them, sodium hydride is preferably used.

Note that, in the case where $R^1$ of Compound (Ia) is a hydrogen atom, the above step is unnecessary.

(3-1-2) Step 1A2 (Ring-Opening Step)

The following description will discuss a step (Step 1A2) of subjecting Compound (IIa) to ring opening in Step 1A in order to obtain Compound (Ia).

Compound (Ia) can be preferably produced by mixing Compound (IIa) and a halogen acid with each other in a solvent, performing a ring-opening reaction of a heterocycle having an oxygen atom, whereby producing an alkyl halide group and a tertiary hydroxy group.

Examples of the halogen acid encompass hydrogen fluoride, hydrogen chloride, hydrogen bromide, and hydrogen iodide. Among them, the hydrogen chloride and the hydrogen bromide are preferably used. The halogen acid may be introduced as gas, or may be dissolved in a solvent and then the resultant solution may be added. Note that Compound (Ia) may be obtained from Compound (IIa) by adding a halide salt and another kind of acid (e.g., toluenesulfonic acid, methanesulfonic acid, or sulfuric acid) to thereby produce a halogen acid in a system. Examples of the halide salt encompass lithium chloride, lithium bromide, lithium fluoride, sodium chloride, sodium bromide, sodium fluoride, potassium chloride, potassium bromide, and potassium fluoride.

The solvent is not particularly limited. Examples of the solvent encompass: amides such as N,N-dimethylacetamide, N-methylpyrrolidone, and N,N-dimethylformamide; alcohols such as methanol and ethanol; ethers such as tetrahydrofuran and dioxane; and water. Among them, N,N-dimethylformamide is preferably used.

While a reaction temperature can be set appropriately in accordance with a solvent, a base, and the like to be used, the reaction temperature is preferably −20° C. to 250° C., and more preferably −10° C. to 150° C. A reaction time can be set appropriately in accordance with a solvent, a base, and the like to be used, and is preferably 0.1 hour to several days, and more preferably 0.5 hour to 2 days.

Note that, in the case where $R^1$ of Compound (Ia) is a hydrogen atom, the above step is performed with use of Compound (IIIa) instead of Compound (IIa).

(3-2) Step 1B

The following description will discuss a method for producing Compound (IIIa) for use in Step 1A.

Compound (IIIa) for use in Step 1A can be preferably produced by the following synthesizing method.

Step 1B includes the step of subjecting a hydroxyalkyl compound, represented by the following general formula (IV), to ring closing in order to obtain Compound (IIIa) (Step 1B; see the following reaction formula (2)).

Reaction formula (2)

[Chem. 13]

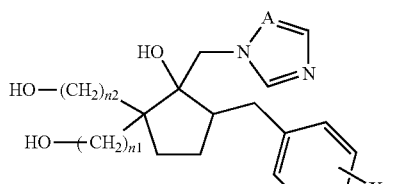

(IV)

↓ Ring closing

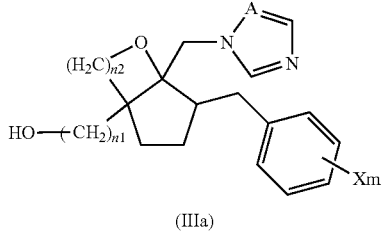

(IIIa)

where X, m, A, n1, and n2 are as having been already described above.

Compound (IIIa) is preferably synthesized by reacting Compound (IV) in a solvent in the presence of sulfonyl chlorides and an excess amount of the base.

Examples of the sulfonyl chlorides encompass p-toluene sulfonyl chloride and methan sulfonyl chloride. Among them, p-toluene sulfonyl chloride is preferably used.

The base is not particularly limited. Examples of the base encompass: metal hydrides such as sodium hydride; and alkoxide of alkalin metal such as sodium methoxide, sodium ethoxide, sodium t-butoxide, and potassium t-butoxide. Among them, a sodium hydride can be preferably used.

An amount of the sulfonyl chloride to be used per mole of Compound (IV) is preferably 1 mole to 2 moles. An amount of the base employed per mole of Compound (IV) is preferably 2.5 moles to 10 moles, and more preferably 2.8 moles to 6 moles.

The solvent is not particularly limited. Examples of the solvent encompass: amides such as N,N-dimethylacetamide, N-methylpyrrolidone, and N,N-dimethylformamide; and ethers such as tetrahydrofuran and dioxane; dimethylsulfoxide; and mixture solvents thereof. Among them, tetrahydrofuran can be preferably used.

A reaction temperature can be set appropriately in accordance with the kinds of a solvent, Compound (IV), a sulfonyl chloride, and a base to be used, and is preferably −100° C. to 200° C., and more preferably −50° C. to 150° C. A reaction time can be set appropriately in accordance with the kinds of a solvent, Compound (IV), a sulfonyl chloride, and a base to be used, and is preferably 0.1 hour to several days, and more preferably 0.5 hour to 2 days.

(3-3) Step 1C

Compound (IV) for use in Step 1B can be preferably produced by the following synthesizing method.

First, an oxirane derivative represented by the following general formula (VII) is obtained by converting a carbonyl compound represented by the following general formula (VIII) into an oxirane. Next, the resultant Compound (VII) is reacted with 1,2,4-triazole or an imidazole compound ("Compound (VI)") represented by the following general formula (VI) to thereby obtain a compound represented by the following general formula (V). Then, a protective group of a hydroxy group represented by G is deprotected in the resultant Compound (V), which results in synthesis of Compound (IV). A series of the above reaction steps (Step 1C) is represented by the following Reaction formula (3).

Reaction formula (3)

[Chem. 14]

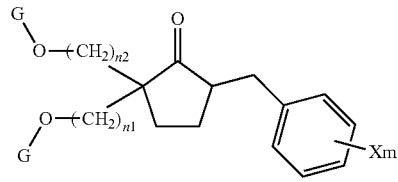

(VIII)

↓ Conversion into oxirane

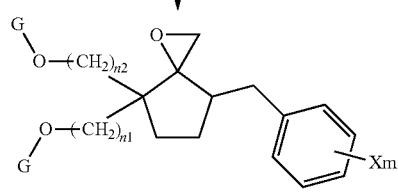

(VII)

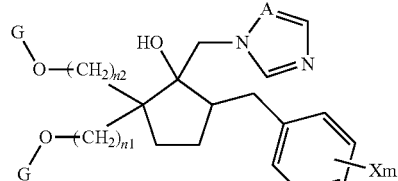

(V)

↓ Deprotection

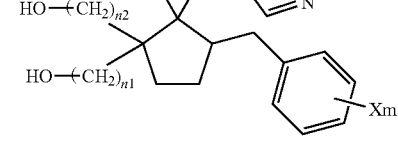

(IV)

where X, m, A, n1, and n2 are as having been already described above. M represents a hydrogen atom or an alkalin metal. G represents a protective group, and is not particularly limited provided that Compound (V) can be produced from Compound (VII). Further, two G may be identical with or different from each other. Examples of the protective group encompass: alkoxymethyl groups such as methoxymethyl group and ethoxymethyl group; lower alkyl groups such as t-butyl group and methyl group; and substituted or unsubstituted benzyl group. Further, two G may form a ring, and, in this case, methylene acetal, isopropylidene ketal, or the like may be used as a protective group. A specific example where two G form a ring will be described below.

(3-3-1) Step 1C1 (Conversion into Oxirane)

The following description will discuss more specifically a step (Step 1C1) of converting Compound (VIII) into oxirane in Step 1C in order to obtain Compound (VII).

As a first method for synthesizing Compound (VII), for example, Compound (VIII) and sulfur ylide can be reacted with each other in a solvent. Examples of sulfur ylide encompass sulfonium methylides such as dimetylsulfonium methylide and sulfoxonium methylides such as dimethylsulfoxonium methylide.

The sulfonium methylides and the sulfoxonium methylides employed can be produced by reacting, in a solvent, a sulfonium salt (e.g., sulfonium halide such as trimethylsulfonium iodide and trimethylsulfonium bromide) or a sulfoxonium salt (e.g., sulfoxonium halide such as trimethylsulfoxonium iodide and trimethylsulfoxonium bromide) with a base.

In this case, an amount of sulfonium methylides or sulfoxonium methylides to be used per mole of Compound (VIII) is preferably 0.5 mole to 5 moles, and more preferably 0.8 mole to 2 moles.

The solvent to be used is not particularly limited. Examples of the solvent encompass: amides such as N-methylpyrrolidone, N,N-dimethylacetamide, and N,N-dimethylformamide; ethers such as tetrahydrofuran and dioxane; dimethylsulfoxide; and mixture solvents thereof.

The base to be used to produce sulfonium methylides or sulfoxonium methylides is not particularly limited. Examples of the base encompass: metal hydrides such as sodium hydride; and alkoxide of alkalin metals such as sodium methoxide, sodium ethoxide, sodium t-butoxide, and potassium t-butoxide.

A reaction temperature and a reaction time can be set appropriately in accordance with the kinds of solvent, Compound (VIII), sulfonium salt or sulfoxonium salt, base, etc. to be used. The reaction temperature is preferably −100° C. to 200° C., and more preferably −50° C. to 150° C. The reaction time is preferably 0.1 hour to several days, and more preferably 0.5 hour to 2 days.

Next, another method for synthesizing Compound (VII) (second synthesizing method) will be described. Specifically, Compound (VII) can be produced by reacting Compound (VIII) with samarium iodide and diiodomethane in a solvent, and then treating the compound thus reacted with a base.

While the base is not particularly limited, sodium hydroxide, for example, can be used. Samarium iodide to be used can be produced by reacting metal samarium with 1,2-diiodoethane or diiodomethane in an anhydrous solvent. The solvent to be used is not particularly limited. Examples of the solvent encompass ethers such as tetrahydrofuran.

While an amount of the base with respect to Compound (VIII) is not particularly limited, the amount of the base employed per mole of Compound (VIII) is preferably 0.5 mole to 10 moles, and more preferably 0.8 mole to 6 moles. Further, in the case where the compound thus reacted is processed with a base, a sodium hydroxide aqueous solution or the like may be used since no anhydrous system is required.

A reaction temperature and a reaction time can be set appropriately in accordance with the kinds of solvent, base, etc. to be used. The reaction temperature is preferably −100° C. to 150° C., and more preferably −50° C. to 100° C. The reaction time is preferably 0.1 hour to several days, and more preferably 0.5 hour to 2 days.

(3-3-2) Step 1C2 (Conversion into Azole)

The following description will discuss more specifically a step (Step 1C2) of reacting Compound (VII) and Compound (VI) with each other in Step 1C in order to obtain Compound (V).

Compound (V) is produced by mixing Compound (VII) with Compound (VI) in a solvent, and then forming a carbon-nitrogen bond between a carbon atom constituting an oxirane ring in an oxirane derivative (Compound (VII)) and a nitrogen atom in 1,2,4-triazole or imidazole (Compound(VI)).

While the solvent employed is not particularly limited, can be, for example, amides such as N-methylpyrrolidone, N,N-dimethylacetamide, and N,N-dimethylformamide.

The amount of Compound (VI) employed per mole of Compound (VII) is preferably 0.5 to 10 moles, and more preferably 0.8 to 5 moles. A base may be added if necessary. In a case where the base is added, the amount of the base employed per mole of Compound (VI) is preferably 0 mole to 5 moles (excluding 0), and more preferably 0.5 mole to 2 moles.

A reaction temperature may be set appropriately in accordance with the kinds of the solvent, the base, and the like to be used. The reaction temperature is preferably 0° C. to 250° C., and more preferably 10° C. to 150° C. A reaction time may be set appropriately in accordance with the kinds of the solvent, the base, and the like to be used. The reaction time is preferably 0.1 hour to several days, and more preferably 0.5 hour to 2 days.

It is possible to produce Compound (V) by producing Compound (VII) and then reacting it stepwise with Compound (VI). However, when a reaction for conversion into an oxirane is carried out alone in the first synthetic method described above, a by-product (such as an oxetane derivative) is produced, resulting in a reduced yield. In order to avoid this reduced yield, it is necessary to carry out conversion into an azole while producing Compound (VII) (see the following reaction formula (4)).

Reaction formula (4)

[Chem. 15]

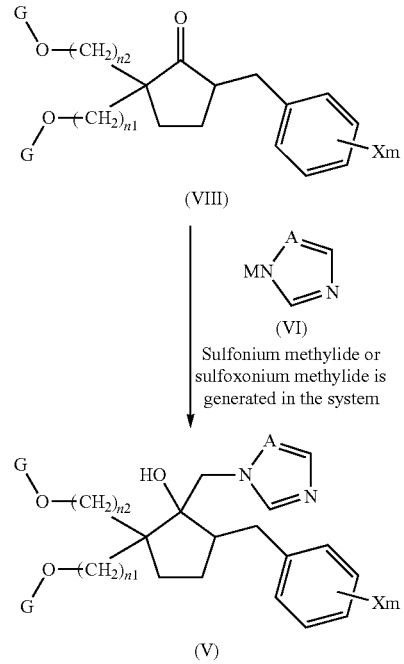

where X, m, A, G, M, n1, and n2 are as having been already described above.

In such a case, Compound (VIII) and Compound (VI) are dissolved in (i) a polar solvent having an amide bond, (ii) dimethyl sulfoxide, or (iii) a mixture solvent of a polar solvent and an alcohol. Then, (a) a sulfonium salt such as a trimethylsulfonium salt or a sulfoxonium salt such as a trimethylsulfoxonium salt and (b) a base are added to this, so that sulfonium methylides such as dimetylsulfonium methylide or sulfoxonium methylides such as dimethyl sulfoxonium methylide are produced in the reaction system. In this way, Compound (VII) is produced while being converted into an azole. In a case where it is preferable to intermittently add at least one of (i) a sulfonium salt such as a trimethylsulfonium salt or a sulfoxonium salt such as a trimethylsulfoxonium salt and (ii) a base, it is preferable to intermittently add one of them or both of them.

The solvent to be used is not particularly limited. Examples of the solvent encompass: polar solvents having an amide bond such as N-methylpyrrolidone, N,N-dimethylacetamide, and N,N-dimethylformamide; and dimethyl sulfoxide. The alcohol to be added to the mixture solvent may be, for example, t-butanol.

The base employed for producing sulfonium methylides or sulfoxonium methylides are not particularly limited. Examples of the base encompass: a metal hydride such as sodium hydride; and an alkoxide of an alkaline metal such as sodium methoxide, sodium ethoxide, sodium t-butoxide, and potassium t-butoxide. In addition, an alkaline metal salt of 1,2,4-triazole or imidazole may also be used.

A reaction temperature may be set appropriately in accordance with the kinds of the solvent, Compound (VIII), sulfonium salt or sulfoxonium salt, base, and the like to be used. The reaction temperature is preferably −100° C. to 250° C., and more preferably −50° C. to 200° C. A reaction time may be set appropriately in accordance with the kinds of the solvent, Compound (VIII), sulfonium salt or sulfoxonium salt, base, and the like to be used. The reaction time is preferably 0.1 hour to several days, and more preferably 0.5 hour to 2 days.

The number of times when at least one of (i) a sulfonium salt (e.g., trimethyl sulfonium halide) or a sulfoxonium salt (e.g., trimethyl sulfonium halide) and (ii) a base is added intermittently is not particularly limited provided that it is the number of times allowing a predetermined aim to be accomplished. For example, the number of times is preferably 2 to 20 times, and more preferably 3 to 15 times. The total amount of a sulfonium salt or a sulfoxonium salt employed per mole of Compound (VIII) is preferably 0.5 mole to 5 moles, more preferably 0.8 mole to 2 moles.

The amount of Compound (VI) employed per mole of Compound (VIII) is preferably 0.5 mole to 10 moles, and more preferably 0.8 mole to 5 moles. It is preferable to use Compound (VI) in which M is an alkaline metal.

A method for converting Compound (VII) into an azole while producing the oxirane derivative may be carried out by referring to a known technique.

(3-3-3) Step 1C3 (Deprotecting Step)

The following description will discuss more preferably a step (Step 1C3) for deprotecting a protective group of Compound (V) in Step 1C in order to obtain Compound (IV).

A preferable condition of the deprotection differs depending on the kind of the protective group. Note, however, that, in the case of using an alkoxymethyl group such as a methoxymethyl group and an ethoxyethyl group, a lower alkyl group such as a t-butyl group and a methyl group, or a cyclic acetal or ketal protective group such as methylene acetal and isopropylidene ketal, the deprotection is carried out preferably in a solvent under an acidic condition involving hydrogen chloride or sulfuric acid and the like.

The acid preferably employed in the deprotection may be a halogenated hydrogen such as hydrogen chloride or an inorganic acid such as sulfuric acid. While the amount employed is not particularly limited, the amount of the acid employed per mole of Compound (V) is 0.5 mole to 100 moles, and preferably 0.8 mole to 20 moles.

A reaction temperature is preferably 0° C. to 200° C., and more preferably a room temperature to 100° C. A reaction time is preferably 0.1 hour to several days, and more preferably 0.5 hour to 2 days.

Note that, in the case where two G are different from each other, a protective group G for protecting —$(CH_2)_{n1}$—OH may be maintained when Compound (IV) is obtained. In this case, the protective group G for protecting —$(CH_2)_{n1}$—OH may be appropriately selected so as not to be deprotected in this step.

Further, the protective group maintained may be deprotected in the same way as Step 1C3 after a ring-closing reaction in Step 1B. With this method, it is possible in some cases to reduce a side reaction of the ring-closing reaction.

(3-4) Step 1D

Compound (VIII) for use in Step 1C can be synthesized preferably by the method shown below.

That is, a keto ester compound represented by the following general formula (XII), which has been obtained by causing a compound represented by the following general formula (XIII) to be subjected to benzylation, is hydroxyalkylated to obtain a compound represented by the following general formula (XI). Further, Compound (XI) is hydroxyalkylated to obtain a compound represented by the following general formula (X). Then, for example, a protective group such as a methoxymethyl group or a t-butyl group is introduced into the hydroxy group in Compound (X) to effect derivatization into a compound represented by the following general formula (IX). Thereafter, Compound (IX) is hydrolyzed/decarbonated to obtain a carbonyl compound represented by the following general formula (VIII). A series of these reaction steps ("Step 1D") is represented by the following reaction formula (5).

[Chem. 16]

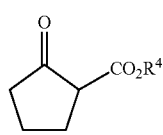
(XIII)

Reaction formula (5)

[Chem. 17]

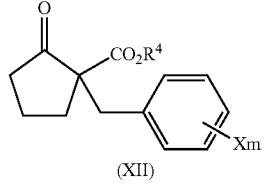
(XII)

↓ Hydroxyalkylation

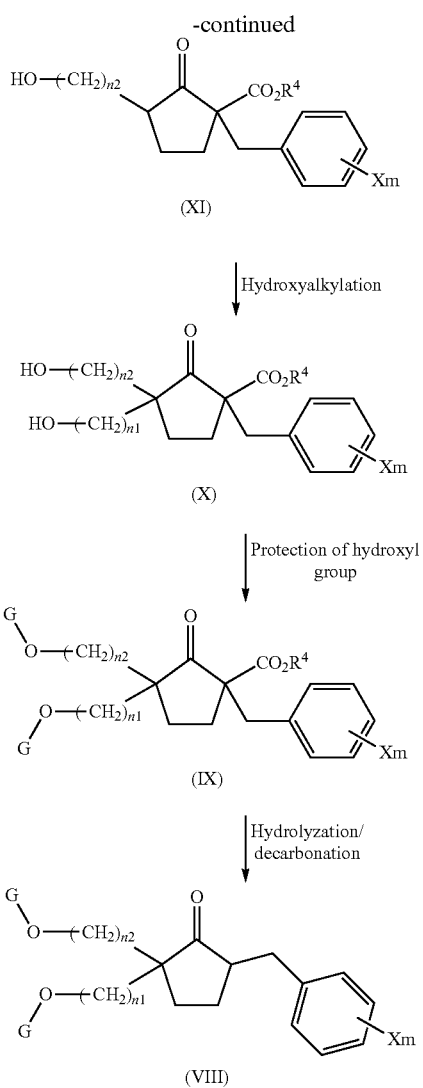

where X, m, G, n1, and n2 are as having been already described above. $R^4$ represents a $C_1$-$C_4$ alkyl group.

(3-4-1) Step 1D1 (Hydroxyalkylating Step)

The following description will discuss a step (Step 1D1) of hydroxyalkylating Compound (XII) in Step 1D in order to obtain Compound (X). Step 1D1 includes the step (Step 1D1a) of hydroxyalkylating Compound (XII) in order to obtain Compound (XI) and the step of (Step 1D1b) further hydroxyalkylating Compound (XI) in order to obtain Compound (X). Hereinafter, Step 1D1a and Step 1D1b will be described below more specifically.

(Step 1D1a: First Hydroxyalkylating Step)

In Step 1D1a, Compound (XI) can be produced by reacting Compound (XII) and hydroxyalkyl halide with each other in a solvent in the presence of a base. A hydroxy group of hydroxyalkyl halide to be used may be protected by a protective group G in advance.

The amount of hydroxyalkyl halide employed per mole of Compound (XII) is 0.5 mole to 20 moles, and preferably 0.8 mole to 10 moles.

The base can for example be, but not limited to, a carbonate of an alkaline metal such as sodium carbonate and potassium carbonate, a hydroxide of an alkaline metal such as sodium hydroxide, or an organic base such as triethylamine. The amount of the base employed per mole of Compound (XII) is 0.1 mole to 10 moles, and preferably 0.2 mole to 5 moles.

A reaction temperature is preferably 0° C. to 250° C., and more preferably 0 to 100° C. A reaction time is preferably 0.1 hour to several days, and more preferably 0.5 hour to 2 days.

While the solvent is not particularly limited, examples of the solvent encompass: ethers such as diethyl ether, tetrahydrofuran, and dioxane; aromatic hydrocarbons such as benzene, toluene, and xylene; and water, and these solvents may be used in combination as necessary. Note that, in the case where the reaction system forms two phases, it is preferable to use a phase transfer catalyst such as a customary quaternary ammonium salt (e.g., benzyltriethylammonium chloride).

In the case where a hydroxyalkyl group to be introduced is a hydroxymethyl group, Compound (XII) may be reacted with formaldehyde or a formaldehyde derivative (hereinafter, referred to as "formaldehyde etc.") in a solvent in the presence of a base.

Examples of the formaldehyde derivative encompass paraformaldehyde, 1,3,5-trioxane, and formaldehyde dialkyl acetal.

Note that, as Compound (XII), a compound produced by a known method (e.g., a method described in Patent Literature 1) may be used.

(Step 1D1b: Second Hydroxyalkylating Step)

A hydroxyalkyl group in Step 1D1b can be introduced in the same way as the method in Step 1D1a.

Note that, in the case where two hydroxyalkyl groups to be introduced are identical with each other (in the case of n1=n2), it is not always necessary to carry out Step 1D1b. In this case, Compound (XII) can be hydroxyalkylated at a time by setting an amount of hydroxyalkyl halide employed per mole of Compound (XII) to 2 or more moles in. Step 1D1a. For example, in the case where Compound (XII) is bishydroxymethylated (n1=n2=1), an amount of formaldehyde etc. employed per mole of Compound (XI) may be set to 2 or more moles.

(3-4-2) Step 1D2 (Protective Group Introducing Step)

The following description will discuss a step (Step 1D2) of introducing a protective group for a hydroxy group of Compound (X) in Step 1D in order to obtain Compound (IX).

The protective group for protecting the hydroxy group is not particularly limited. The protective group is preferably an alkoxymethyl group such as a methoxymethyl group and an ethoxymethyl group or a lower alkyl group such as a t-butyl group. Introduction of these protective groups is carried out with use of an acid catalyst. Note that, (a) in the case of introduction of an alkoxymethyl group, it is preferable to employ a method involving an acetal exchange of the hydroxy group in Compound (X) with use of a formaldehyde dialkylacetal. Meanwhile, (b) in the case of introduction of a t-butyl group, it is preferable to employ a method involving introduction of the protective group to the hydroxy group in Compound (X) with use of isobutene. Further, (c) in the case of protecting two hydroxy groups with acetal and ketal simultaneously, it is preferable to employ a method involving a suitable aldehyde, ketone, acetal corresponding to the aldehyde, or ketal corresponding to the ketone under an acidic catalyst.

First, the description will discuss the case where the protective group is an alkoxymethyl group (case (a)).

Preferable examples of an acid encompass: an inorganic acid such as hydrochloric acid, phosphoric acid (including a compound allowing an acidic group to be produced by addition of an alcohol or water, such as diphosphorus pentoxide), and sulfuric acid; and an organic acid such as p-toluenesulfonic acid and methanesulfonic acid. The formaldehyde dialkylacetal is employed preferably in the presence of an acid in a solvent or in a solvent-free system. It is further preferable to add a compound (for example, diphosphorus pentoxide) capable of removing a produced alcohol.

The amount of the formaldehyde dialkylacetal employed per mole of Compound (X) is preferably 0.5 mole to 50 moles, and more preferably 0.8 mole to 10 moles. The amount of the acid employed per mole of Compound (X) is preferably 0.001 mole to 10 moles, and more preferably 0.002 mole to 5 moles.

A reaction temperature is preferably 0° C. to 250° C., and more preferably 0° C. to 150° C. A reaction time is preferably 0.1 hour to several days, and more preferably 0.5 hour to 2 days.

In a case where the protective group is a t-butyl group (case (b)), it is preferable to react Compound (X) with isobutene in a solvent in the presence of an inorganic acid (such as hydrochloric acid, phosphoric acid, and sulfuric acid) or an organic acid (such as p-toluenesulfonic acid and trifluoroacetic acid).

An amount of isobutene employed per mole of Compound (X) is preferably 0.5 mole to 100 moles, and more preferably 0.8 mole to 20 moles. The amount of the acid employed per mole of Compound (X) is preferably 0.001 mole to 10 moles, and more preferably 0.002 mole to 5 moles.

A reaction temperature is preferably 0° C. to 200° C., and more preferably 0° C. to 100° C. A reaction time is preferably 0.1 hour to several days, and more preferably 0.5 hour to 2 days.

In a case where the protective group is isopropylidene ketal (case (c)), it is preferable to react Compound (X) with acetone or acetone dimethyl acetal in a solvent in the presence of an inorganic acid (such as hydrochloric acid, phosphoric acid, and sulfuric acid) or an organic acid (such as p-toluenesulfonic acid, methanesulfonic acid, and trifluoroacetic acid).

An amount of acetone or acetone dimethyl acetal employed per mole of Compound (X) is preferably 0.5 to 100 moles, and more preferably 0.8 to 20 moles. The amount of the acid employed per mole of Compound (X) is preferably 0.001 to 10 moles, and more preferably 0.002 to 5 moles.

A reaction temperature is preferably 0° C. to 200° C., and more preferably 0° C. to 100° C. A reaction time is preferably 0.1 hour to several days, and more preferably 0.5 hour to 2 days.

In the case where hydroxyalkyl halide whose hydroxy group has been protected in advance is used in Step 1D1a and 1D1b, Step 1D2 does not have to be carried out.

(3-4-3) Step 1D3 (Hydrolyzing/Decarbonating Step)

The following description will discuss a step (Step 1D3) of hydrolyzing/decarbonating Compound (IX) in Step 1D in order to obtain Compound (VIII).

Step 1D3 is preferably carried out in a solvent in the presence of a base. As the base, an alkaline metal base such as sodium hydroxide and potassium hydroxide can be used. An amount of the base employed per mole of Compound (IX) is preferably 0.1 mole to 50 moles, and more preferably 0.2 mole to 20 moles.

Examples of the solvent encompass water, water combined with, for example, an alcohol, a solvent composition consisting of solvents which do not form a homogenous layer (such as water and toluene). When using a solvent which does not form a homogenous layer, a phase transfer catalyst (e.g., a customary quaternary ammonium salt) may be used in the reaction system.

A reaction temperature is preferably 0° C. to a reflux temperature, and more preferably a room temperature to the reflux temperature. A reaction time is preferably 0.1 hour to several days, and more preferably 0.5 hour to 24 hours.

The method for producing Compound (Ia) among azole derivatives in accordance with the present invention have been described so far. The above Steps 1A to 1D can be summarized as a flow shown in the following reaction formula (6).

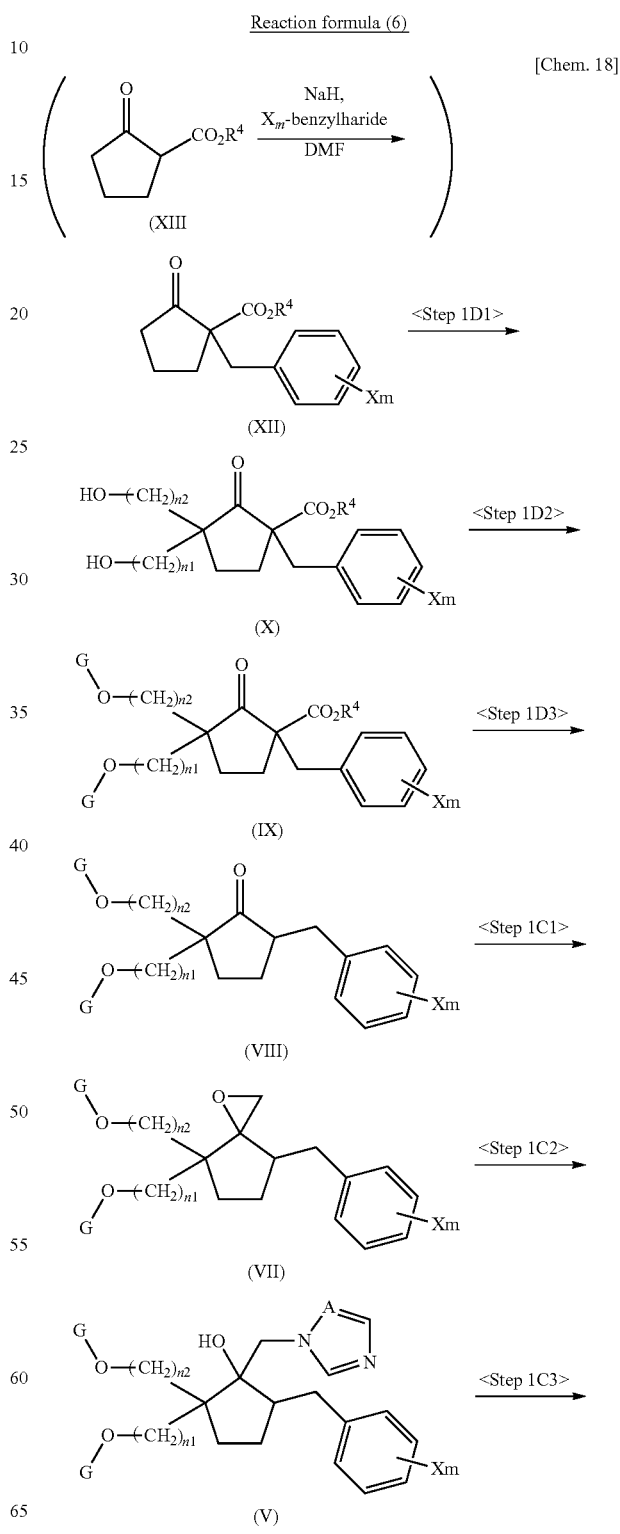

-continued

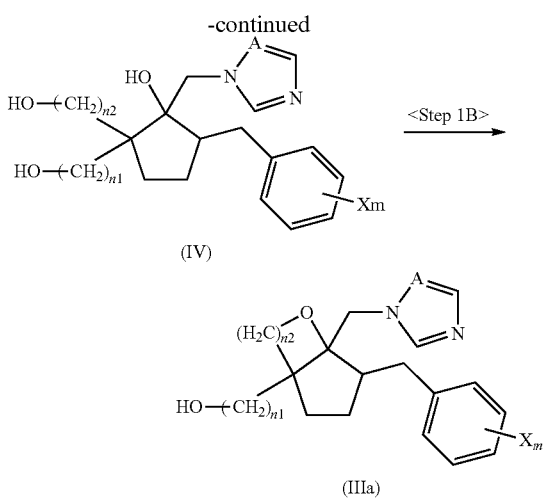

(IV)

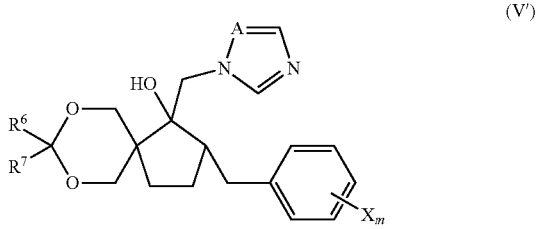

(IIIa)

(3-5) Examples of Step 1C and Step 1D

As Compound (V) in which two G form a ring, there is an azole derivative (hereinafter, referred to as azole derivative (V')) represented by the following general formula (V').

[Chem. 19]

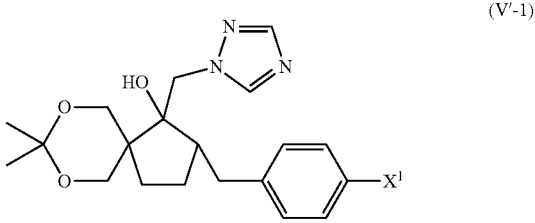

(V')

In the general formula (V'), $R^6$ and $R^7$ independently represent a hydrogen atom, a $C_1$-$C_4$ alkyl group, a phenyl group, or a benzyl group.

Examples of $C_1$-$C_4$ alkyl group encompass methyl group, ethyl group, n-propyl group, 1-methylethyl group, 1-methylpropyl group, 2-methylpropyl group, n-butyl group, and 1,1-dimethylethyl group.

At least one hydrogen atom of a phenyl group in $R^6$ and $R^7$, and at least one hydrogen atom of a phenyl part of a benzyl group in $R^6$ or $R^7$ may be substituted with a $C_1$-$C_4$ alkyl group, a $C_1$-$C_4$ alkoxy group, or a halogen atom. Examples of the $C_1$-$C_4$ alkyl group as a substituent encompass methyl group, ethyl group, n-propyl group, 1-methylethyl group, 1-methylpropyl group, 2-methylpropyl group, n-butyl group, and 1,1-dimethylethyl group. Examples of the $C_1$-$C_4$ alkoxy group as a substituent encompass methoxy group, ethoxy group, and n-propoxy group. Examples of the halogen atom as a substituent encompass fluorine atom, chlorine atom, and bromine atom.

In particular, it is preferable that $R^6$ and $R^7$ independently represent a hydrogen atom or a $C_1$-$C_4$ alkyl group, more preferable that $R^6$ and $R^7$ independently represent a $C_1$-$C_4$ alkyl group, further preferable that $R^6$ and $R^7$ independently represent a $C_1$-$C_2$ alkyl group, and particularly preferable that both $R^6$ and $R^7$ represent a methyl group.

X is identical with X described above, and represents a halogen atom, a $C_1$-$C_4$ alkyl group, a $C_1$-$C_4$ haloalkyl group, a $C_1$-$C_4$ alkoxy group, a $C_1$-$C_4$ haloalkoxy group, a phenyl group, a cyano group, or a nitro group.

Examples of the halogen atom encompass chlorine atom, fluorine atom, bromine atom, and iodine atom.

Examples of the $C_1$-$C_4$ alkyl group encompass methyl group, ethyl group, n-propyl group, 1-methylethyl group, 2-methylpropyl group, n-butyl group, and 1,1-dimethylethyl group.

Examples of $C_1$-$C_4$ haloalkyl group encompass trifluoromethyl group, 1,1,2,2,2-pentafluoroethyl group, chloromethyl group, trichloromethyl group, and bromomethyl group.

Examples of the $C_1$-$C_4$ alkoxy group encompass methoxy group, ethoxy group, and n-propoxy group.

Examples of the $C_1$-$C_4$ haloalkoxy group encompass trifluoromethoxy group, difluoromethoxy group, 1,1,2,2,2-pentafluoroethoxy group, and 2,2,2-trifluoroethoxy group.

X preferably represents a halogen atom, a $C_1$-$C_3$ haloalkyl group, a $C_1$-$C_3$ haloalkoxy group, a $C_1$-$C_3$ alkyl group, or a $C_1$-$C_3$ alkoxy group, more preferably a halogen atom, $C_1$-$C_2$ haloalkyl group or $C_1$-$C_2$ haloalkoxy group, further preferably a halogen atom, and particularly preferably a fluorine atom or a chlorine atom.

The symbol m is identical with the m described above, and represents an integer of 0 to 5. In the case where m is 2 or more, the plurality of Xs may be identical with or different from each other. In particular, m preferably represents an integer of 0 to 3, and more preferably an integer of 0 to 2.

A bond position of X is not particularly limited. In the case where m is 1, X is preferably positioned such that the benzyl becomes 4-substituted benzyl.

A represents a nitrogen atom or a methyne group. Preferably A is a nitrogen atom.

A preferable example of the azole derivative (V') is an azole derivative represented by the following general formula (V'-1), however, the azole derivative (V') is not limited thereto.

[Chem. 20]

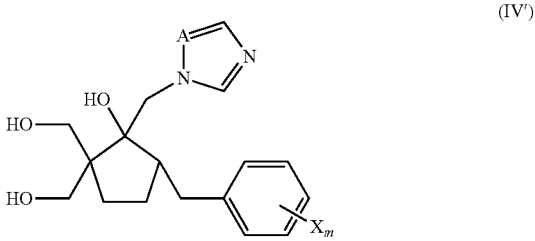

(V'-1)

(where $X^1$ represents a hydrogen atom, a fluorine atom, or a chlorine atom.)

The azole derivative (V') is preferably used in production of an azole derivative (hereinafter, referred to as "azole derivative (IV')") represented by the following general formula (IV').

[Chem. 21]

(IV')

(where X, m, and A in the formula (IV') are identical with those in the formula (V'), respectively.)

The azole derivative (IV') is one form of Compound (IV), and is preferably used as an intermediate compound of an azole derivative which is advantageous in exhibiting an excellent biocidal effect on a wide range of microorganisms which are pathogenic to plants.

Note that the azole derivative (V') itself is also advantageous in exhibiting an excellent biocidal effect on a wide range of microorganisms which are pathogenic to plants.

The azole derivative (V') is one form of Compound (V), and can be produced from Compound (XII) by carrying out the above Step 1D and Step 1C. That is, the azole derivative (V') can be produced in accordance with the following scheme 1 from Compound (XII) that can be produced by using a known technique. Note that scheme 1 shows, in addition to the steps of producing the azole derivative (V'), a step of producing the azole derivative (IV') from the azole derivative (V').

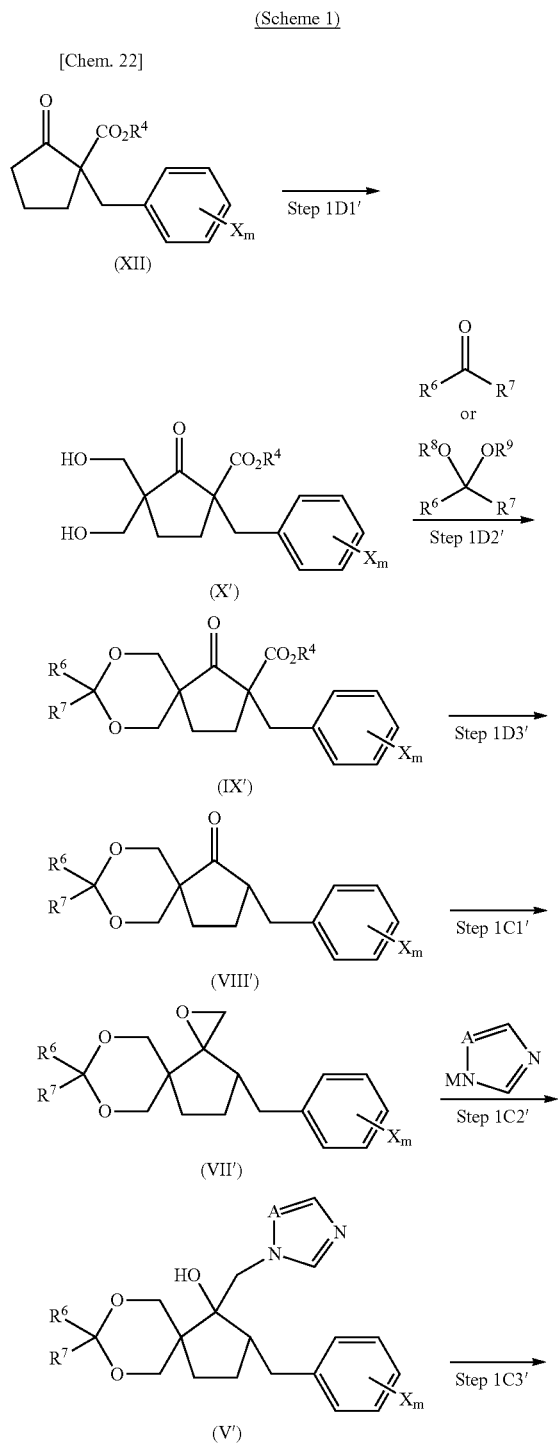

(Scheme 1)

[Chem. 22]

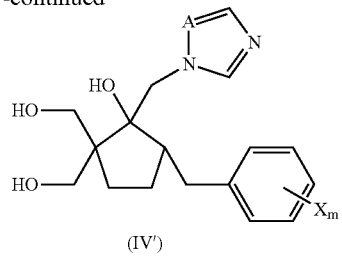

(IV')

Hereinafter, each step will be described.

(Step 1D1': Hydroxymethylating Step)

In Step 1D1', which is one form of Step 1D1, Compound (XII) described above is hydroxymethylated in order to obtain a compound (Compound (X) where n1 is 1 and n2 is 1; hereinafter, referred to as "Compound (X')") represented by a general formula (X').

As a method for hydroxymethylating Compound (XII), for example, Compound (XII) is reacted with formaldehyde or a formaldehyde derivative in a solvent in the presence of a base.

Examples of the base encompass: carbonates of an alkaline metal such as sodium carbonate, potassium carbonate, sodium hydrogen carbonate, and potassium hydrogen carbonate; hydroxides of alkaline metal such as sodium hydroxide; and organic bases such as triethylamine, however, the base is not limited thereto. An amount of the base per mole of Compound (XII) is, for example, 0.01 mole to 10 moles, and more preferably 0.1 mole to 5 moles.

A reaction temperature is, for example, 0° C. to 250° C., and preferably 0° C. to 100° C. A reaction time is, for example, 0.1 hour to several days, and preferably 0.5 hour to 2 days.

The solvent is not particularly limited. Examples of the solvent encompass: ethers such as diethyl ether, tetrahydrofuran (THF), dimethoxyethane, and dioxane; aromatic hydrocarbons such as benzene, toluene, and xylene; and alcohols such as methanol and ethanol, amides such as N-methylpyrrolidone, N,N-dimethylacetamide, and N,N-dimethylformamide; and water, and those solvents may be used in combination as necessary. Note that, in the case where the reaction system forms two phases, it is preferable to use a phase transfer catalyst such as a customary quaternary ammonium salt (e.g., benzyltriethylammonium chloride).

Examples of the formaldehyde derivative encompass paraformaldehyde, 1,3,5-trioxane, and formaldehyde dialkyl acetal.

An amount of the formaldehyde or the formaldehyde derivative employed per mole of Compound (XII) is, for example, 1 mole to 40 moles, and preferably 1.6 moles 20 moles.

(Step 1D2': Protective Group Introducing Step)

In Step 1D2', which is one form of Step 1D2, protective groups respectively for protecting each hydroxy group in respective two hydroxymethyl groups of Compound (X') are introduced with use of a compound simultaneously, thereby obtaining a compound (hereinafter, referred to as "Compound (IX')") represented by a general formula (IX').

As a method for introducing a protective group for a hydroxy group of Compound (X'), for example, Compound (X') is reacted with acetal or ketone in the presence of acid.

As acetal, a compound represented by the following general formula (XIV) may be used.

[Chem. 23]

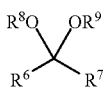

(XIV)

$R^6$ and $R^7$ in the formula (XIV) are identical with functional groups represented by $R^6$ and $R^7$ in the azole derivative (V'). $R^8$ and $R^9$ independently represent a $C_1$-$C_4$ alkyl group such as a methyl group and an ethyl group.

Further, as ketone, a compound represented by the following general formula (XV) can be used.

[Chem. 24]

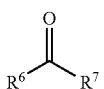

(XV)

$R^6$ and $R^7$ in the formula (XV) are identical with functional groups represented by $R^6$ and $R^7$ in the azole derivative (V').

An amount of acetal or ketone employed per mole of Compound (X') is, for example, 0.5 mole to 20 moles, and preferably 0.8 mole to 10 moles.

Examples of the acid encompass: inorganic acids such as hydrochloric acid, phosphoric acid, and sulfuric acid; and organic acids such as p-toluenesulfonic acid, methanesulfonic acid, and trifluoroacetic acid. An amount of the acid employed per mole of Compound (X') is, for example, 0.001 mole to 10 moles, and preferably 0.002 mole to 2 moles.

A reaction temperature is, for example, 0° C. to 200° C., and preferably 0° C. to 100° C. A reaction time is, for example, 0.1 hour to several days, and preferably 0.5 hour to 2 days.

(Step 1D3': Hydrolyzing/Decarbonating Step)

In Step 1D3', which is a form of Step 1D3, Compound (IX') is hydrolyzed and decarbonated in order to obtain a compound (hereinafter, referred to as "Compound (VIII')") represented by a general formula (VIII').

As a method for hydrolyzing/decarbonating Compound (IX'), for example, Compound (IX') is reacted in a solvent in the presence of a base.

As the base, an alkaline metal salt base such as sodium hydroxide or potassium hydroxide can be preferably used. An amount of the base employed per mole of Compound (IX') is, for example, 0.1 mole to 50 moles, and preferably 0.2 mole to 20 moles.

Examples of the solvent encompass water, water combined with alcohols, a solvent composition consisting of solvents which do not form a homogenous layer (such as water and toluene). When using a solvent which does not form a homogenous layer, a phase transfer catalyst (e.g., a customary quaternary ammonium salt) may be used in the reaction system.

A reaction temperature is, for example, 0° C. to a reflux temperature, and preferably a room temperature to the reflux temperature. A reaction time is, for example, 0.1 hour to several days, and preferably 0.5 hour to 24 hours.

(Step 1C1': Conversion into Oxirane)

In Step 1C1' which is one form of Step 1C1, Compound (VIII') is converted into oxirane in order to obtain an oxirane derivative (hereinafter, referred to as "oxirane derivative (VII')") represented by the general formula (VII').

As a method for converting Compound (VIII') into oxirane, for example, Compound (VIII') and sulfur ylide are reacted with each other in a solvent.

Examples of the sulfur ylide encompass: sulfonium methylides such as dimetylsulfonium methylide; and sulfoxonium methylides such as dimethylsulfoxonium methylide. Sulfonium methylides and sulfoxonium methylides employed can be produced by reacting, in a solvent, a sulfonium salt (e.g., sulfonium halide such as trimethylsulfonium iodide and trimethylsulfonium bromide) or a sulfoxonium salt (e.g., sulfoxonium halide such as trimethylsulfoxonium iodide and trimethylsulfoxonium bromide (TMSOB)) with a base. In this case, an amount of the sulfonium methylides or sulfoxonium methylides employed per mole of Compound (VIII') is preferably 0.5 mole to 5 moles, and more preferably 0.8 mole to 2 moles.

The solvent is not particularly limited, and examples of the solvent encompass: amides such as N-methylpyrrolidone (NMP), N,N-dimethylacetamide (DMA); and N,N-dimethylformamide (DMF); ethers such as tetrahydrofuran and dioxane; dimethylsulfoxide; and mixture solvent thereof.

The base for use in production of sulfonium methylides or sulfoxonium methylides is not particularly limited. It is preferable to use a base such as a metal hydride (e.g., sodium hydride) or an alkoxide of alkalin metal (e.g., sodium methoxide, sodium ethoxide, sodium t-butoxide, and potassium t-butoxide).

A reaction temperature and a reaction time are set appropriately in accordance with the kinds of solvent, Compound (VIII'), sulfonium salt or sulfoxonium salt, and base. The reaction temperature is, for example, −100° C. to 200° C., and preferably −50° C. to 150° C. The reaction time is, for example, 0.1 hour to several days, and preferably 0.5 hour to 2 days.

(Step 1C2': Conversion into Azole)

In Step 1C2', which is one form of Step 1C2, an oxirane derivative (VII') is converted into azole in order to obtain an azole derivative (V').

As a method for converting the oxirane derivative (VII') into azole, for example, the oxirane derivative (VII') is reacted with Compound (VI) described above in a solvent. More specifically, the oxirane derivative (VII') and Compound (VI) are mixed with each other in the solvent, which results in producing a carbon-nitrogen bond between a carbon atom constituting an oxirane ring in the oxirane derivative (VII') and a nitrogen atom of 1,2,4-triazole or imidazole. Thus the azole derivative (V') is produced.

While the solvent is not particularly limited, for example, amides such as N-methylpyrrolidone, N,N-dimethylacetamide, and N,N-dimethylformamide can be used.

An amount of Compound (VI) employed per mole of the oxirane derivative (VII') is, for example, 0.5 mole to 10 moles, and preferably 0.8 mole to 5 moles. Further, a base may be added as necessary. In the case of adding the base, an amount of the base employed per mole of the oxirane derivative (VII') is, for example, 0 mole to 5 moles (excluding 0), and more preferably 0.5 mole to 2 moles.

A reaction temperature can be set appropriately in accordance with the kind of solvent or base, and is, for example, preferably 0° C. to 250° C., and preferably 10° C. to 150° C. A reaction time can be set appropriately in accordance with the kinds of solvent or base, and is, for example, 0.1 hour to several days, and more preferably 0.5 hour to 2 days.

As described above, it is possible to produce the azole derivative (V') by producing the oxirane derivative (VII') and then reacting it stepwise with Compound (VI). However, when a reaction for conversion of Compound (VIII') into an oxirane is carried out alone in the first synthetic method described above, a by-product (such as an oxetane derivative) is produced, resulting in a reduced yield. In order to avoid this reduced yield, it is necessary to carry out conversion into azole may be carried out while producing Compound (VII') (see the following reaction formula (4')).

[Chem. 25]

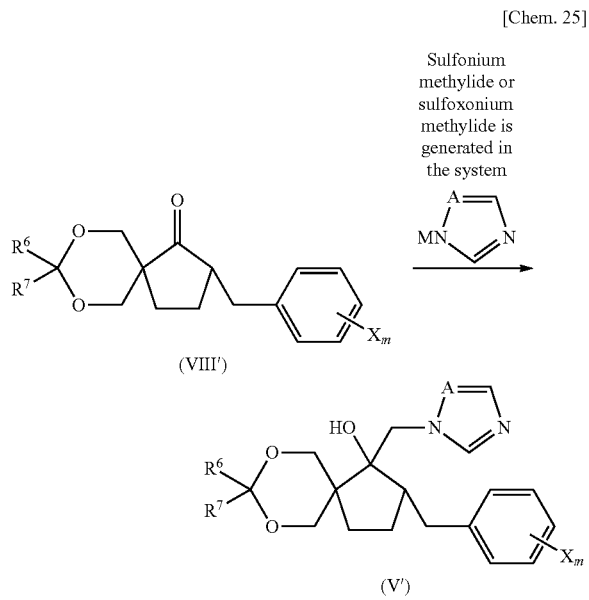

In such a case, Compound (VIII') and Compound (VI) are dissolved in (i) a polar solvent having an amide bond, (ii) dimethyl sulfoxide, or (iii) a mixture solvent of a polar solvent and alcohol. Then, to this, a sulfonium salt such as trimethylsulfonium salt or a sulfoxonium salt such as trimethylsulfoxonium salt and a base are added to produce sulfonium methylides such as dimetylsulfonium methylide or sulfoxonium methylides such as dimethyl sulfoxonium methylide in the reaction system. Then the oxirane derivative (VII') is produced while being converted into azole. In this case, in the case where it is preferable to intermittently add at least one of (i) a sulfonium salt such as a trimethylsulfonium salt or a sulfoxonium salt such as a trimethylsulfoxonium salt and (ii) a base, it is preferable to intermittently add one of them or both of them.

Examples of the solvent encompass: a polar solvent having an amide bond such as N-methylpyrrolidone, N,N-dimethylacetamide, and N,N-dimethylformamide; and dimethylsulfoxide. Further, the alcohol in the mixture solvent is, for example, t-butanol.

The base for use in production of sulfonium methylides or sulfoxonium methylides is not particularly limited. Examples of base encompass metal hydrides such as sodium hydride and alkoxide of alkalin metal such as sodium methoxide, sodium ethoxide, sodium t-butoxide, and potassium t-butoxide. Further, alkaline metal salt of 1,2,4-triazole or imidazole may be used.

A reaction temperature can be set appropriately in accordance with the kinds of solvent, Compound (VIII'), sulfonium salt or sulfoxonium salt, and base. The reaction temperature is, for example, −100° C. to 250° C., and preferably −50° C. to 200° C. A reaction time can be set appropriately in accordance with the kinds of solvent, Compound (VIII'), sulfonium salt or sulfoxonium salt, and base. The reaction time is, for example, 0.1 hour to several days, and preferably 0.5 hour to 2 days.

The number of times at least one of (i) sulfonium salt such as trimethylsulfonium salt or sulfoxonium salt such as trimethylsulfoxonium salt and (ii) a base is intermittently added is not particularly limited provided that it is the number of times allowing a predetermined aim to be accomplished. A preferable number of times is 2 times to 20 times, and more preferably 3 times to 15 times. A total amount of sulfonium salt or sulfoxonium salt employed per mole of Compound (VIII') is preferably 0.5 mole to 5 moles, and more preferably 0.8 mole to 2 moles.

An amount of Compound (VI) employed per mole of Compound (VIII') is, for example, 0.5 mole to 10 moles, and preferably 0.8 mole to 5 moles. It is preferable to use Compound (VI) in which M is an alkaline metal.

(Step 1C3': Deprotecting Step)

Further, in Step 1C3', which is one form of Step 1C3, a protective group of the azole derivative (V') is deprotected in order to obtain the azole derivative (IV') from the azole derivative (V').

As a method for deprotecting the protective group of the azole derivative (V'), for example, the azole derivative (V') is reacted in a solvent in the presence of acid.

The solvent employed is not particularly limited provided that a deprotecting reaction is carried out. As the solvent, for example, both of a solvent which forms a homogenous layer with water such as alcohols (e.g., methanol and ethanol) and a solvent which does not form a homogenous layer with water such as aromatic hydrocarbons (e.g., toluene and xylene) can be preferably used.

An inorganic acid can be preferably used as the acid, and examples of the acid encompass halogenated hydrogens such as hydrogen chloride and sulfuric acid. While an amount of the acid employed is not particularly limited, the amount of the acid employed per mole of the azole derivative (V') is, for example, 0.5 mole to 100 moles, and preferably 0.8 mole to 20 moles.

A reaction temperature is, for example, 0° C. to 200° C., and preferably a room temperature to 100° C. A reaction time is, for example, 0.1 hour to several days, and preferably 0.5 hour to 2 days.

It is possible to preferably produce an azole derivative (V') of the present invention by carrying out those reactions from Step 1D1' to Step 1D3' and those reactions from Step 1C1' to Step 1C2' as described above. Further, it is possible to produce the azole derivative (IV') from the azole derivative (V') by carrying out the reaction of Step 1C3'.

The azole derivative (IV') can be preferably used as a production intermediate of an azole derivative (hereinafter, referred to as "azole derivative (Ia')") represented by the following general formula (Ia').

[Chem. 26]

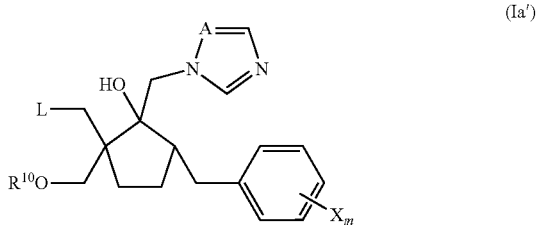

(where A, X, and m in the formula (Ia') are identical with those in the formula (V'), respectively, L represents a halogen atom, and $R^{10}$ represents a $C_1$-$C_3$ alkyl group.)

The azole derivative (Ia') is one form of Compound (Ia), and is a novel azole derivative which is advantageous in exhibiting an excellent biocidal effect on a wide range of microorganisms which are pathogenic to plants. The azole derivative (Ia') is one form of Compound (Ia), and can be produced from the azole derivative (V') by carrying out the above Steps 1B and 1A. The following description will discuss a method for producing the azole derivative (Ia') from the azole derivative (IV') in accordance with Scheme 2.

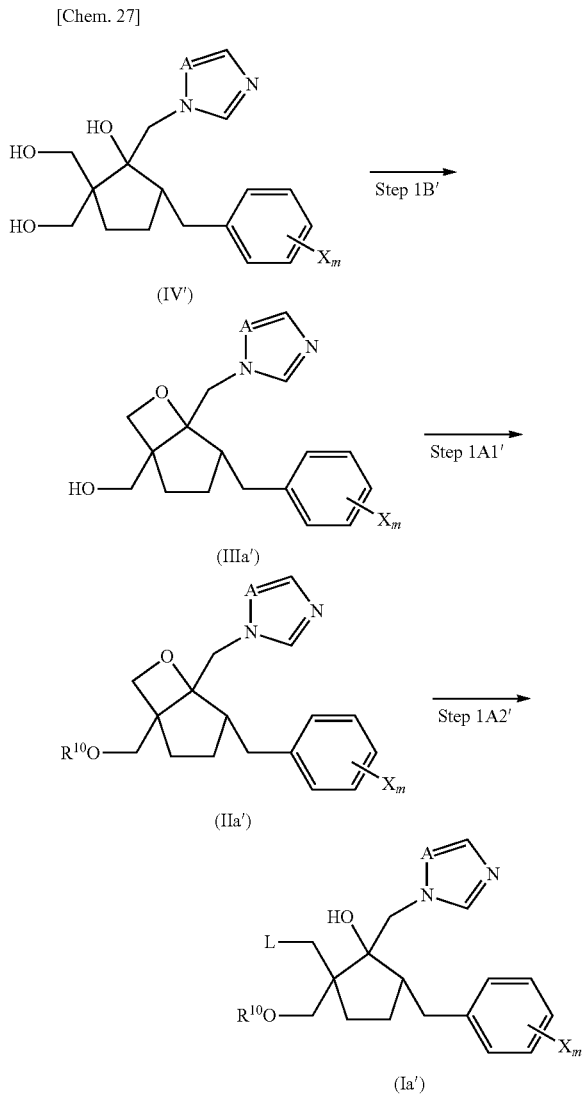

(Step 1B': Ring-Closing Step)

In Step 1B', which is one form of Step 1B, the azole derivative (IV') is subjected to ring closing in order to obtain an azole derivative (hereinafter, referred to as "azole derivative (IIIa')") represented by the general formula (IIIa').

As a preferable method for synthesizing the azole derivative (IIIa'), for example, the azole derivative (IV') is reacted with sulfonyl chlorides in a solvent in the presence of a base.

Examples of the sulfonyl chlorides encompass p-toluene sulfonyl chloride and methanesulfonyl chloride.

The base is not particularly limited. Examples of the base encompass metal hydrides such as sodium hydride and alkoxide of alkalin metal such as sodium methoxide, sodium ethoxide, sodium t-butoxide, and potassium t-butoxide.

An amount of the sulfonyl chlorides employed per mole of the azole derivative (IV') is preferably 1 mole to 2 moles. An amount of the base employed per mole of the azole derivative (IV') is preferably 2.5 moles to 10 moles, and more preferably 2.8 moles to 6 moles.

The solvent is not particularly limited, and examples of the solvent encompass: amides such as N,N-dimethylacetamide, N-methylpyrrolidone, and N,N-dimethylformamide; ethers such as tetrahydrofuran and dioxane; dimethylsulfoxide; and mixture solvents thereof.

A reaction temperature can be set appropriately in accordance with the kinds of solvent, azole derivative (IV'), sulfonyl chloride, and base, and is, for example, −100° C. to 200° C., and preferably −50° C. to 150° C. A reaction time can be set appropriately in accordance with the kinds of solvent, azole derivative (IV'), sulfonyl chloride, and base, and is, for example, 0.1 hour to several days, and preferably 0.5 hour to 2 days.

(Step 1A1': Alkylating Step)

In Step 1A1', which is one form of Step 1A1, the azole derivative (IIIa') is alkylated in order to obtain an azole derivative (hereinafter, referred to as "azole derivative (IIa')") represented by the general formula (IIa').

In the general formula (IIa'), $R^{10}$ represents a $C_1$-$C_3$ alkyl group. Specific examples of $R^{10}$ encompass methyl group, ethyl group, 1-methylethyl group, and n-propyl group.

As a method for alkylating the azole derivative (IIIa'), for example, metalalkoxide prepared from a hydroxy group of the azole derivative (IIIa') and an alkaline metal base is reacted with a $C_1$-$C_3$ alkyl having a leaving group in a solvent at a room temperature.

Examples of the solvent encompass: ether solvents such as THF; solvents of amides such as N-methylpyrrolidone, and N,N-dimethylacetamide; aromatic solvents such as benzene and toluene; and a halide solvent such as methylene chloride.

Examples of the alkyl having a leaving group encompass alkyl halide such as iodide and bromide and sulfonic acid ester such as tosyloxyalkyl and mesyloxyalkyl.

Examples of the alkaline metal base encompass sodium, sodium hydride, sodium hydroxide, and potassium hydroxide.

(Step 1A2': Ring-Opening Step)

In Step 1A2', which is one form of Step 1A2, the azole derivative (IIa') is subjected to ring opening in order to obtain the azole derivative (Ia'). For example, the azole derivative (Ia') can be preferably produced as follows: the azole derivative (IIa') and a halogen acid are mixed with each other in a solvent; and an alkyl halide group and a tertiary hydroxy group are produced by carrying out a ring-opening reaction.

Examples of the halogen acid encompass hydrogen fluoride, hydrogen chloride, hydrogen bromide, and hydrogen iodide. Among them, the hydrogen chloride and the hydrogen bromide are preferably used. The halogen acid may be introduced as gas, or may be dissolved and then added to a solvent. Note that the azole derivative (Ia') may be obtained from the azole derivative (IIa') by adding a halide salt and another kind of acid (e.g., a toluenesulfonic acid, a methanesulfonic acid, or a sulfuric acid) to thereby produce halogen acid in a system. Examples of the halide salt encompass lithium chloride, lithium bromide, lithium fluoride, sodium chloride, sodium bromide, sodium fluoride, potassium chloride, potassium bromide, and potassium fluoride.

While the solvent is not particularly limited, examples of the solvent encompass: amides such as N-methylpyrrolidone, N,N-dimethylacetamide, and N,N-dimethylformamide;

alcohols such as methanol and ethanol; ethers such as tetrahydrofuran and dioxane; and water.

A reaction temperature can be set appropriately in accordance with a solvent and a base, and is, for example, −20° C. to 250° C., and preferably −10° C. to 150° C. A reaction time can be set appropriately in accordance with a solvent and a base, and is, for example, 0.1 hour to several days, and preferably 0.5 hour to 2 days.

The azole derivative (IV') can be preferably used for producing the azole derivative (Ia') as described above. However, the azole derivative (IV') is not used only as an intermediate compound of the azole derivative (Ia'). For example, the azole derivative (IV') can be also preferably used as an intermediate of an azole derivative represented by the following general formula (XVI). An azole derivative (XVI) is also a novel azole derivative which is advantageous in exhibiting an excellent biocidal effect on a wide range of microorganisms which are pathogenic to plants.

[Chem. 28]

(XVI)

(where A, X, and m in the formula (XVI) are identical with those in the formula (V'), respectively, and L represents a halogen atom.)

As described above, the azole derivative (V') is also advantageous in exhibiting an excellent biocidal activity on microorganisms which are pathogenic to plants. Therefore, the azole derivative (V') can be used as an active ingredient of an agro-horticultural agent. An agro-horticultural agent containing the azole derivative (V') is particularly effective for controlling diseases in stems, leaves, seeds of wheat by subjecting the seeds a seed treatment. While the azole derivative (V') can be used solely as the active ingredient of the agro-horticultural agent, i.e., can be used without containing any other components, the azole derivative (V') is usually used in various forms, such as a dust formulation, wettable powder, granule, and emulsifiable concentrate, by mixing the azole derivative (V') with a solid carrier, a liquid carrier, a surfactant, and other formulation auxiliary agents. A carrier and an auxiliary agent are not particularly limited, and it is possible to appropriately select any carrier and auxiliary agent from those which have been conventionally used for the agro-horticultural agent. For example, the following carriers and auxiliary agents can be used. Further, a mixture ratio thereof can be selected from various ratios, and is not limited to ratios described in the following Examples. Further, the seeds which have been subjected to the seed treatment with use of the agro-horticultural agent containing the azole derivative (V') are also encompassed in the present invention.

(4) Second Method for Producing Compound (I)

(4-1) Step 2A

The following description will discuss a second method for producing an azole derivative of the present invention.

Among azole derivatives of the present invention a compound (hereinafter, referred to as "Compound (Ib)") represented by the following general formula (Ib) is produced in Step 2A. Hereinafter, the method for producing Compound (Ib) in Step 2A will be described.

[Chem. 29]

(Ib)

where $R^1$, $R^2$, X, m, A, and n1 are as having been already described above.

The second method for producing Compound (Ib) includes the steps of: thioetherifying Compound (IIIa) with use of a condensing agent; and obtaining Compound (Ib) by reacting the resultant compound represented by the following general formula (IIb) with an arbitrary halogen acid to open a heterocycle having an oxygen atom (Step 2A: see the following reaction formula (7)).

Reaction formula (7)

[Chem. 30]

(IIIa)

↓ Thioetherification (IIb)

↓ Ring-opening (Ib)

where $R^1$, $R^2$, X, m, A, n1, and n2 are as having been already described above.

(4-1-1) Step 2A1 (Thioetherifying Step)

In Step 2A, the following description will discuss more specifically a step (Step 2A1) in which Compound (IIb) is obtained by condensing Compound (IIIa) to thioetherify Compound (IIIa). Note that, in order to obtain Compound (IIIa), a method similar to the method described in the first method for producing Compound (I) described above may be used.

While the method for condensing Compound (IIIa) is not particularly limited, a method for thioetherifying a hydroxy group in Compound (IIIa) with alkyl thiol ($R^1SH$) with use of an acid catalyst or a condensing agent can be preferably used.

The acid catalysts such as acid aqueous solutions (e.g., a sulfuric acid and hydrochloric acid) and organic acids (e.g., formic acid and acetic acid) can be preferably used. Further, as the condensing agent, DCC can be preferably used.

(4-1-2) Step 2A2 (Ring-Opening Step)

As to a step (Step 2A2) of obtaining Compound (Ib) by subjecting Compound (IIb) used in Step 2A to ring opening, Compound (Ib) can be obtained in the same way as Compound (Ia) except that Compound (IIb) is used instead of Compound (IIa) and Compound (IIb) is subjected to ring opening to obtain Compound (Ib) in the above Step 1A2.

Further, Compound (IIIa) can be obtained by performing Step 1B, Step 1C, and Step 1D described above.

(5) Third Method for Producing Compound (I)

(5-1) Step 3A

The following description will discuss a third method for producing an azole derivative in accordance with the present invention.

Among the azole derivatives of the present invention, Compound (Ib) is produced in Step 3A as well as Step 2A described above. The following description will discuss a method for producing Compound (Ib) in Step 3A.

The method for producing Compound (Ib) includes the steps of: halogenating Compound (IIIa); thioetherifying the resultant halogenated Compound (IIIb); opening, with use of an arbitrary halogen acid, a heterocycle containing an oxygen atom of Compound (IIb) which has been obtained by such thioetherification in order to obtain Compound (Ib) (Step 3A: see the following reaction formula (8)).

Reaction formula (8)

[Chem. 31]

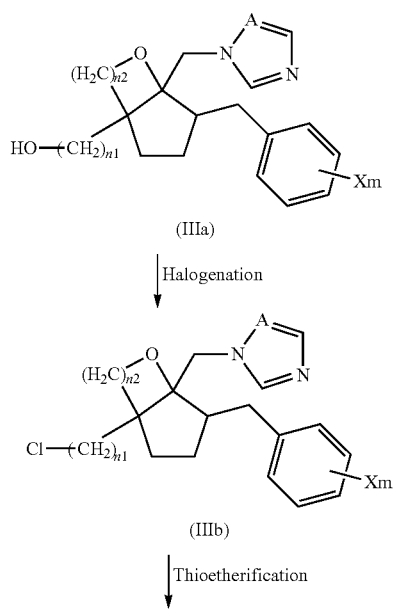

where $R^1$, $R^2$, X, m, A, n1, and n2 are as having been already described above.

(5-1-1) Step 3A1 (Halogenating Step)

In Step 3A, the following description will discuss more specifically a step (Step 3A1) of halogenating Compound (IIIa) in order to obtain Compound (IIIb). Note that Compound (IIIa) can be obtained by a method similar to the method described in the first method for producing Compound (I) described above.

While the method for halogenating Compound (IIIa) is not particularly limited, there can be employed a method with use of a hydrochloric acid, thionyl chloride, an aqueous hydrogen bromide solution, or the like can be used.

(5-1-2) Step 3A2 (Thioetherifying Step)

The following description will discuss a step (Step 3A2) of carrying out a thioetherification reaction with respect to Compound (IIIb) in Step 3A in order to obtain Compound (IIb).

While the method of carrying out the thioetherification reaction is not particularly limited, a method for thioetherifying a hydroxy group of Compound (IIIa) with use of alkyl thiol ($R^1SH$) in the presence of a base catalyst can be preferably used.

Examples of the base encompass: inorganic bases such as sodium hydroxide, potassium hydroxide, and potassium carbonate; and organic bases such as triethylamine and pyridine.

(5-1-3) Step 3A3 (Ring-Opening Step)

As to a step (Step 3A3) of subjecting Compound (IIb) to ring opening to obtain Compound (Ib), Compound (Ib) can be obtained in the same way as Compound (Ia) which is obtained by opening the ring of Compound (IIa) in the above Step 1A2 except that Compound (IIb) is used instead of Compound (IIa) and Compound (IIb) is subjected to ring opening to obtain Compound (Ib) in Step 1A2.

Further, Compound (IIIa) can be obtained by carrying out Step 1B, Step 1C, and Step 1D described above.

(6) Fourth Method for Producing Compound (I)

(6-1) Step 4A

The following description will discuss a fourth method for producing an azole derivative in accordance with the present invention.

Among the azole derivatives of the present invention, a compound represented by the following general formula (Ic) (hereinafter, referred to as "Compound (Ic)") is produced in

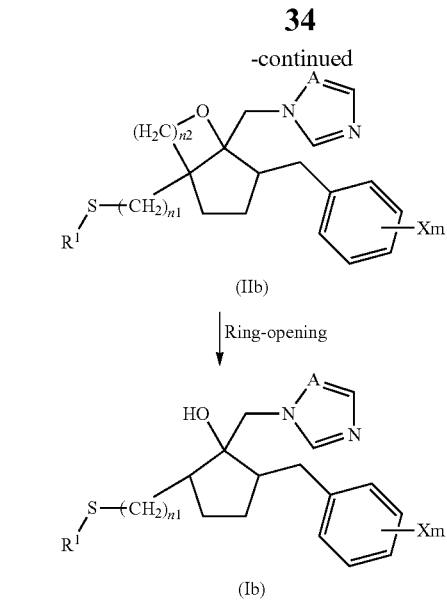

Step 4A. The following description will discuss a method for producing Compound (Ic) in Step 4A.

[Chem. 32]

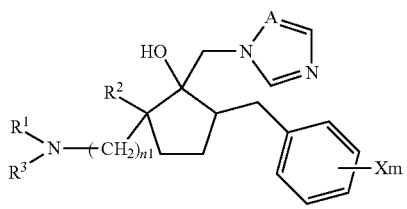

(Ic)

The method for producing Compound (Ic) includes the steps of: reacting Compound (IIIa) with substituted sulfonyl chloride to sulfonylate Compound (IIIa); aminating a compound which has been obtained through such sulfonylation, which compound is represented by the following general formula (IIIc); and opening, with use of an arbitrary halogen acid, a heterocycle containing an oxygen atom in a compound which has been obtained through such amination, which compound is represented by the following general formula (IIc), in order to obtain Compound (Ic) (Step 4A: see the following reaction formula (9)).

Reaction formula (9)

[Chem. 33]

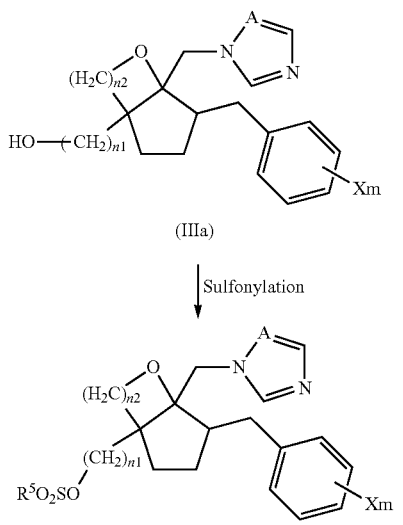

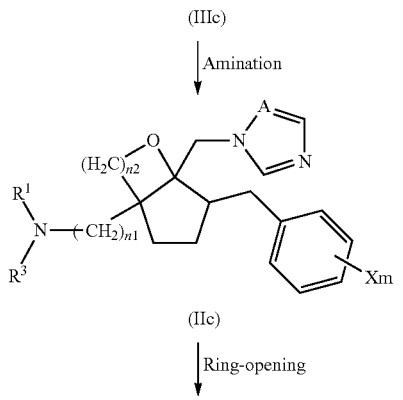

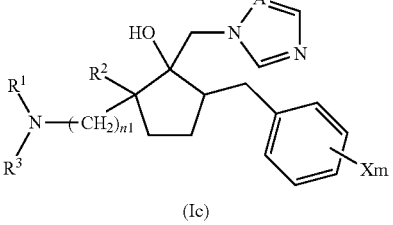

(Ic)

where $R^1$, $R^2$, $R^3$, X, m, A, n1, and n2 are as having been already described above.

$R^5$ represents a lower alkyl group, a phenyl group, or a naphthyl group. Examples of the lower alkyl group encompass methyl group, ethyl group, n-propyl group, isopropyl group, and trifluoromethyl group. The phenyl group and the naphthyl group may be configured such that one or more hydrogen atoms are substituted. Examples of a substituted phenyl group or a substituted naphthyl group encompass 4-methylphenyl group, 2-nitrophenyl group, and 5-dimethylamino naphthyl group. In particular, $R^5$ preferably represents a methyl group or a 4-methylphenyl group.

(6-1-1) Step 4A1 (Sulfonylating Step)

The following description will discuss a step (Step 4A1) of obtaining sulfonylated Compound (IIIc) by reacting Compound (IIIa) with substituted sulfonyl chloride in Step 4A. Note that, in order to obtain Compound (IIIa), a method similar to the method described in the first method for producing Compound (I) described above can be used.

While the method for sulfonylating Compound (IIIa) is not particularly limited, substituted sulfonic acid ester may be obtained by, for example, reacting a hydroxy group of Compound (IIIa) with substituted sulfonyl chloride in the presence of a base. Examples of the substituted sulfonyl chloride encompass p-toluene sulfonyl chloride and methanesulfonyl chloride.

(6-1-2) Step 4A2 (Aminating Step)

The following description will discuss a step (Step 4A2) of aminating Compound (IIIc) obtained in Step 4A1 in order to obtain Compound (IIc).

While the method for aminating Compound (IIIc) is not particularly, limited, for example, Compound (IIIc) can be reacted with alkylamine.

Alternatively, a method for obtaining Compound (IIc) may include the steps of: halogenating Compound (IIIa); and aminating the resultant Compound (IIIb) (see the following reaction formula (10)).

Reaction formula (10)

[Chem. 34]

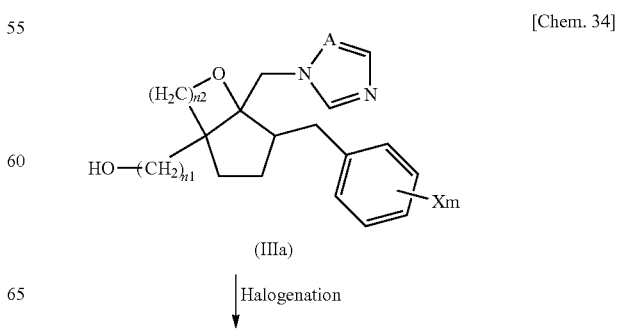

(IIIa)

↓ Halogenation

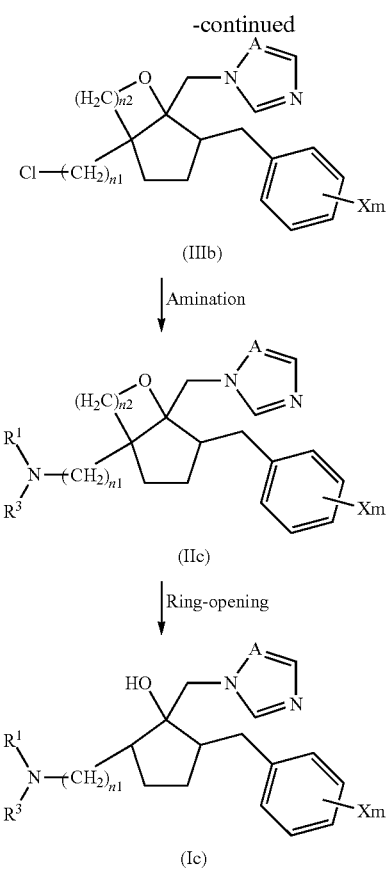

where $R^1$, $R^2$, $R^3$, X, m, A, n1, and n2 are as having been already described above.

Compound (IIIb) can be obtained from Compound (IIIa) by the above method as well as Step 3A1 described above. Further, Compound (IIc) can be produced by reacting a haloalkyl group of Compound (IIIb) with alkylamine ($R^1R^3NH$).

Examples of the base encompass: inorganic bases such as sodium hydroxide, potassium hydroxide, and potassium carbonate; and organic bases such as triethylamine and pyridine.

(6-1-3) Step 4A3 (Ring-Opening Step)

As to a step (Step 4A3) of obtaining Compound (Ic) by subjecting Compound (IIc) used in Step 4A to ring opening, Compound (Ic) can be obtained in the same way as Compound (Ia) which is obtained by subjecting Compound (IIa) to ring opening in the above Step 1A2 except that Compound (IIc) is used instead of Compound (IIa) and Compound (IIc) is subjected to ring opening to obtain Compound (Ia) in Step 1A2.

Further, Compound (IIIa) can be obtained by carrying out Step 1B, Step 1C, and Step 1D described above.

3. Agro-Horticultural Agent/Industrial Material Protecting Agent

The following description will discuss the usability of an agro-horticultural agent and an industrial material protecting agent (hereinafter, also referred to as "agro-horticultural agent etc.") containing an azole derivative (see Compound (I)) of the present invention as an active ingredient.

(1) Plant Disease Controlling Effects

An agro-horticultural agent containing Compound (I) as an active ingredient exhibits a controlling effect on a broad range of plant diseases. Examples of diseases are as follows.

Soybean rust (*Phakopsora pachyrhizi*, *Phakopsora meibomiae*), rice blast (*Pyricularia grisea*), rice brown spot (*Cochliobolus miyabeanus*), rice leaf blight (*Xanthomonas oryzae*), rice sheath blight (*Rhizoctonia solani*), rice stem rot (*Helminthosporium sigmoideun*), rice Bakanae disease (*Gibberella fujikuroi*), rice bacterial seedling blight (*Pythium aphanidermatum*), apple powdery mildew (*Podosphaera leucotricha*), apple scab (*Venturia inaequalis*), apple blossom blight (*Monilinia mali*), apple *alternaria* blotch (*Alternaria alternata*), apple *valsa* canker (*Valsa mali*), pear black spot (*Alternaria kikuchiana*), pear powdery mildew (*Phyllactinia pyri*), pear rust (*Gymnosporangium asiaticum*), pear scab (*Venturia nashicola*), grape powdery mildew (*Uncinula necator*), grape downy mildew (*Plasmopara viticola*), grape ripe rot (*Glomerella cingulata*), barley powdery mildew (*Erysiphe graminis* f. sp *hordei*), barley stem rust (*Puccinia graminis*), barley stripe rust (*Puccinia striiformis*), barley stripe (*Pyrenophora graminea*), barley leaf blotch (*Rhynchosporium secalis*), wheat powdery mildew (*Erysiphe graminis* f. sp *tritici*), wheat brown rust (*Puccinia recondita*), wheat stripe rust (*Puccinia striiformis*), wheat eye spot (*Pseudocercosporella herpotrichoides*), wheat Fusarium blight (*Fusarium graminearum, Microdochium nivale*), wheat glume blotch (*Phaeosphaeria nodorum*), wheat leaf blight (*Septoria tritici*), gourd powdery mildew (*Sphaerotheca fuliginea*), gourd anthracnose (*Colletotrichum lagenarium*), cucumber downy mildew (*Pseudoperonospora cubensis*), cucumber phytophthora rot (*Phytophthora capsici*), tomato powdery mildew (*Erysiphe cichoracearum*), tomato early blight (*Alternaria solani*), eggplant powdery mildew (*Erysiphe cichoracearum*), strawberry powdery mildew (*Sphaerotheca humuli*), tobacco powdery mildew (*Erysiphe cichoracearum*), sugar beet cercpspora leaf spot (*Cercospora beticola*), maize smut (*Ustillaga maydis*), plum brown rot (*Monilinia fructicola*), various plants-affecting gray mold (*Botrytis cinerea*), sclerotinia rot (*Sclerotinia sclerotiorum*) and the like may be exemplified. Among them, wheat leaf blight (*Septoria tritici*), which is a critical disease in wheat, is particularly applicable.

Examples of applicable plants may be, for example, wild plants, cultivated plant cultivars, plants and cultivated plant cultivars obtained by conventional biological breeding such as heterologous mating or plasma fusion, and plants and cultivated plant cultivars obtained by genetic engineering. The genetically-engineered plants and the cultivated plant cultivars may be, for example, herbicide-resistant crops, vermin-resistant crops having insecticidal protein-producing genes integrated therein, disease-resistant crops having disease resistance inducer-producing genes integrated therein, palatably improved crops, productively improved crops, preservably improved crops, and productively improved crops. The genetically-engineered cultivated plant cultivars may be, for example, those involving trademarks such as ROUNDUP READY, LIBERTY LINK, CLEARFIELD, YIELDGARD, HERCULEX, BOLLGARD and the like.

(2) Plant Growth Promoting Effect

Furthermore, on a broad range of crops and horticultural plants, the agro-horticultural agent containing Compound (I) as the active ingredient exhibits yield-increasing effects and quality-improving effects by regulating the growth of the crops and plants. Such crops may be, for example, those listed below.

Wheat, barley, oats, rice, rapeseed, sugarcane, corn, maize, soybean, pea, peanut, sugar beet, cabbage, garlic, radish, carrot, apple, pear, citric fruits such as mandarin, orange, and lemon, peach, cherry, avocado, mango, papaya, red pepper, cucumber, melon, strawberry, tobacco, tomato, eggplant, lawn grass, chrysanthemum, azalea, and other ornamental plants.

(3) Industrial Material Protecting Effect

Moreover, an industrial material protecting agent containing Compound (I) as the active ingredient exhibits an excellent ability of protecting an industrial material from broad spectrum of hazardous microorganisms which invade such a material. Examples of such microorganisms are listed below.

Paper/pulp deteriorating microorganisms (including slime-forming microorganisms) such as *Aspergillus* sp., *Trichoderma* sp., *Penicillium* sp., *Geotrichum* sp., *Chaetomium* sp., *Cadophora* sp., *Ceratostomella* sp., *Cladosporium* sp., *Corticium* sp., *Lentinus* sp., *Lenzites* sp., *Phoma* sp., *Polysticus* sp., *Pullularia* sp., *Stereum* sp., *Trichosporium* sp., *Aerobacter* sp., *Bacillus* sp., *Desulfovibrio* sp., *Pseudomonas* sp., *Flavobacterium* sp., and *Micrococcus* sp.; fiber-deteriorating microorganisms such as *Aspergillus* sp., *Penicillium* sp., *Chaetomium* sp., *Myrothecium* sp., *Curvularia* sp., *Gliomastix* sp., *Memnoniella* sp., *Sarcopodium* sp., *Stachybotrys* sp., *Stemphylium* sp., *Zygorhynchus* sp., *Bacillus* sp. and *Staphylococcus* sp.; lumber-deteriorating microorganisms such as *Tyromyces palustris, Coriolus versicolor, Aspergillus* sp., *Penicillium* sp., *Rhizopus* sp., *Aureobasidium* sp., *Gliocladium* sp., *Cladosporium* sp., *Chaetomium* sp., and *Trichoderma* sp.; leather-deteriorating microorganisms such as *Aspergillus* sp., *Penicillium* sp., *Chaetomium* sp., *Cladosporium* sp., *Mucor* sp., *Paecilomyces* sp., *Pilobus* sp., *Pullularia* sp., *Trichosporon* sp., and *Tricothecium* sp.; rubber/plastic-deteriorating microorganisms such as *Aspergillus* sp., *Penicillium* sp., *Rhizopus* sp., *Trichoderma* sp., *Chaetomium* sp., *Myrothecium* sp., *Streptomyces* sp., *Pseudomonas* sp., *Bacillus* sp., *Micrococcus* sp., *Serratia* sp., *Margarinomyces* sp., and *Monascus* sp.; paint-deteriorating microorganisms such as *Aspergillus* sp., *Penicillium* sp., *Cladosporium* sp., *Aureobasidium* sp., *Gliocladium* sp., *Botryodiplodia* sp., *Macrosporium* sp., *Monilia* sp., *Phoma* sp., *Pullularia* sp., *Sporotrichum* sp., *Trichoderma* sp., *Bacillus* sp., *Proteus* sp., *Pseudomonas* sp., and *Serratia* sp.

(4) Formulations (Agro-Horticultural Agent)

An agro-horticultural formulation containing Compound (I) as an active ingredient may contain various components other than Compound (I). For example, the agro-horticultural formulation containing Compound (I) as an active ingredient may contain a solid carrier, a liquid carrier, a surfactant, and other formulation auxiliary agents. The agro-horticultural formulation containing Compound (I) as an active ingredient may have various dosage forms such as a dust formulation, wettable powder, granule, and emulsifiable concentrate.

The agro-horticultural formulation may contain Compound (I) as an active ingredient in an amount of 0.1 to 95% by weight based on the total amount of the agro-horticultural formulation. Compound (I) as an active ingredient is contained preferably in an amount of 0.5 to 90% by weight, and more preferably 2 to 80% by weight.

Carriers, diluents, and surfactants employed as formulation auxiliary agents are exemplified below. Examples of the solid carriers encompass talc, kaolin, bentonite, diatomaceous earth, white carbon, and clay. Examples of the liquid diluents encompass water, xylene, toluene, chlorobenzene, cyclohexane, cyclohexanone, dimethyl sulfoxide, dimethyl formamide, and alcohols. The surfactant can be employed depending on its effect. In the case where the surfactant is an emulsifier, the emulsifier may be, for example, polyoxyethylene alkylaryl ether, polyoxyethylene sorbitan monolaurate and the like. In the case where the surfactant is a dispersing agent, the dispersing agent may be, for example, lignin sulfonate salt, or dibutylnaphthalene sulfonate salt. In the case where the surfactant is a wetting agent, the wetting agent may be, for example, an alkyl sulfonate salt or alkylphenyl sulfonate salt.

The formulation may be used as it is, or used as being diluted in a diluent such as water to a predetermined concentration. In the case where the formulation is used as being diluted, the concentration of Compound (I) in a spray solution is preferably 0.001% to 1.0%.

The amount of the agro-horticultural agent containing Compound (I) employed per one hectare of the agro-horticultural field such as a farm, paddy field, orchard, or greenhouse is 20 g to 5000 g, and more preferably 50 g to 2000 g. However, because the concentration and the amount may vary depending on the dosage form, timing of use, method for use, place of use, subject crop, and the like, it is possible to increase or decrease the concentration and the amount regardless of the ranges mentioned above.

In addition, the agro-horticultural agent in accordance with the present invention can be used by containing active ingredients other than Compound (I), including bactericides, insecticides, acaricides, and herbicides, such as those listed below, thereby enabling the use as an agro-horticultural agent having an enhanced performance.

<Anti-Bacterial Substances>

Acibenzolar-S-methyl, 2-phenylphenol (OPP), azaconazole, azoxystrobin, amisulbrom, bixafen, benalaxyl, benomyl, benthiavalicarb-isopropyl, bicarbonate, biphenyl, bitertanol, blasticidin-S, borax, Bordeaux mixture, boscalid, bromuconazole, bronopol, bupirimate, sec-butylamine, calcium polysulphide, captafol, captan, carbendazim, carboxin, carpropamid, quinomethionate, chloroneb, chloropicrin, chlorothalonil, chlozolinate, cyazofamid, cyflufenamid, cymoxanil, cyproconazole, cyprodinil, dazomet, debacarb, dichlofluanid, diclocymet, diclomezine, dicloran, diethofencarb, difenoconazole, diflumetorim, dimethomorph, dimethoxystrobin, diniconazole, dinocap, diphenylamine, dithianon, dodemorph, dodine, edifenphos, epoxiconazole, ethaboxam, ethoxyquin, etridiazole, enestroburin, famoxadone, fenamidone, fenarimol, fenbuconazole, fenfuram, fenhexamid, fenoxanil, fenpiclonil, fenpropidin, fenpropimorph, fentin, ferbam, ferimzone, fluazinam, fludioxonil, flumorph, fluoroimide, fluoxastrobin, fluquinconazole, flusilazole, flusulfamide, flutolanil, flutriafol, folpet, fosetyl-Al, fuberidazole, furalaxyl, furametpyr, fluopicolide, fluopyram, guazatine, hexachlorobenzene, hexaconazole, hymexazol, imazalil, imibenconazole, iminoctadine, ipconazole, iprobenfos, iprodione, iprovalicarb, isoprothiolane, isopyrazam, isotianil, kasugamycin, copper preparations, such as:copper hydroxide, copper naphthenate, copper oxychloride, copper sulphate, copper oxide, oxine copper, kresoximmethyl, mancopper, mancozeb, maneb, mandipropamid, mepanipyrim, mepronil, metalaxyl, metconazole, metiram, metominostrobin, mildiomycin, myclobutanil, nitrothal-isopropyl, nuarimol, ofurace, oxadixyl, oxolinic acid, oxpoconazole, oxycarboxin, oxytetracycline, pefurazoate, orysastrobin, penconazole, pencycuron, penthiopyrad, pyribencarb, fthalide, picoxystrobin, piperalin, polyoxin, probenazole, prochloraz, procymidone, propamocarb, propiconazole, propineb, proquinazid, prothioconazole, pyraclostrobin, pyrazophos, pyrifenox, pyrimethanil, pyroquilon, quinoxyfen, quintozene, silthiopham, simeconazole, spiroxamine, Sulfur and sulfur formulations, tebuconazole, tecloftalam, tecnazen, tetraconazole, thiabendazole, thifluzamide, thiophanate-methyl, thiram, thiadinil, tolclofos-methyl, tolylfluanid, triadimefon, triadimenol, triazoxide, tricyclazole, tridemorph, trifloxystrobin, triflumizole, triforine, triticonazole, validamycin, vinclozolin, zineb, ziram, zoxarnide, amisulbrom, sedaxane, flutianil, valiphenal, ametoctradin, dimoxystrobin, metrafenone, hydroxyisoxazole, metasulfocarb and the like.

<Insecticides/Acaricides/Nematocides>

Abamectin, acephate, acrinathrin, alanycarb, aldicarb, allethrin, amitraz, avermectin, azadirachtin, azamethiphos, azinphos-ethyl, azinphos-methyl, azocyclotin, *Bacillus firmus, Bacillus subtilis, Bacillus thuringiensis*, bendiocarb, benfuracarb, bensultap, benzoximate, bifenazate, bifenthrin, bioallethrin, bioresmethrin, bistrifluron, buprofezin, butocarboxim, butoxycarboxim, cadusafos, carbaryl, carbofuran, carbosulfan, cartap, CGA50439, chlordane, chlorethoxyfos, chlorphenapyr, chlorfenvinphos, chlorfluazuron, chlormephos, chlorpyrifos, chlorpyrifos methyl, chromafenozide, clofentezine, clothianidin, chlorantraniliprole, coumaphos, cryolite, cyanophos, cycloprothrin, cyfluthrin, cyhalothrin, cyhexatin, cypermethrin, cyphenothrin, cyromazine, Cyazapyr, cyenopyrafen, DCIP, DDT, deltamethrin, demeton-S-methyl, diafenthiuron, diazinon, dichlorophen, dichloropropene, dichlorvos, dicofol, dicrotophos, dicyclanil, diflubenzuron, dimethoate, dimethylvinphos, dinobuton, dinotefuran, emamectin, endosulfan, EPN, esfenvalerate, ethiofencarb, ethion, ethiprole, ethofenprox, ethoprophos, etoxazole, famphur, fenamiphos, fenazaquin, fenbutatin oxide, fenitrothion, fenobucarb, fenothiocarb, fenoxycarb, fenpropathrin, fenpyroximate, fenthion, fenvalerate, fipronil, flonicamid, fluacrypyrim, flucycloxuron, flucythrinate, flufenoxuron, flumethrin, fluvalinate, flubendiamide, formetanate, fosthiazate, halfenprox, furathiocarb, halofenozide, gamma-HCH, heptenophos, hexaflumuron, hexythiazox, hydramethylnon, imidacloprid, imiprothrin, indoxacarb, isoprocarb, isoxathion, lufenuron, malathion, mecarbam, metam, methamidophos, methidathion, methiocarb, methomyl, methoprene, methothrin, methoxyfenozide, metolcarb, milbemectin, monocrotophos, naled, nicotine, nitenpyram, novaluron, noviflumuron, omethoate, oxamyl, oxydemethon methyl, parathion, permethrin, phenthoate, phorate, phosalone, phosmet, phosphamidon, phoxim, pirimicarb, pirimiphos-methyl, profenofos, propoxur, prothiophos, pymetrozin, pyrachlophos, pyrethrin, pyridaben, pyridalyl, pyrimidifen, pyriproxifen, pyrifluquinazon, pyriprole, quinalphos, silafluofen, spinosad, spirodiclofen, spiromesifen, spirotetramat, sulfluramid, sulphotep, SZI-121, tebufenozid, tebufenpyrad, tebupirimphos, teflubenzuron, tefluthrin, temephos, terbufos, tetrachlorvinphos, thiacloprid, thiamethoxam, thiodicarb, thiofanox, thiometon, tolfenpyrad, tralomethrin, tralopyril, triazamate, triazophos, trichlorfon, triflumuron, vamidothion, valifenal, XMC, xylylcarb, imicyafos, lepimectin and the like.

<Plant Growth Regulators>

Ancymidol, 6-benzylaminopurine, paclobutrazol, diclobutrazole, uniconazole, methylcyclopropene, mepiquat chloride, ethefon, chlormequat chloride, inabenfide, prohexadione and its salts, trinexapac-ethyl and the like. As plant hormones, jasmonic acid, brassinosteroid, gibberellin and the like.

(Industrial Material Protecting Agent)

An industrial material protecting agents containing Compound (I) as an active ingredient may contain various components other than Compound (I). The industrial material protecting agents containing Compound (I) as an active ingredient can be used as being dissolved or dispersed in a suitable liquid carrier or as being mixed with a solid carrier. The industrial material protecting agents containing Compound (I) as an active ingredient may further contain an emulsifier, dispersing agent, spreading agent, penetrating agent, wetting agent, stabilizer, and the like. The industrial material protecting agents containing Compound (I) as an active ingredient may have various dosage forms such as a wettable powder, dust formulation, granule, tablet, paste, suspension, and spray. The industrial material protecting agents containing Compound (I) as an active ingredient may contain other biocides, insecticides, deterioration-preventing agent, and the like.

The liquid carrier is not particularly limited provided that it is unreactive with the active ingredient, and may be selected from water, alcohols (e.g., methyl alcohol, ethyl alcohol, ethylene glycol, and cellosolve), ketones (e.g., acetone and methylethylketone), ethers (for example, dimethyl ether, diethyl ether, dioxane, and tetrahydrofuran), aromatic hydrocarbons (e.g., benzene, toluene, xylene, and methylnaphthalene), aliphatic hydrocarbons (e.g., gasoline, kerosene, paraffin oil, machine oil, and fuel oil), acid amides (e.g., dimethyl formamide, N,N-dimethylacetamide, and N-methylpyrrolidone), halogenated hydrocarbons (e.g., chloroform and carbon tetrachloride), esters (e.g., acetic acid ethyl ester and fatty acid glycerin ester), nitriles (e.g., acetonitrile), and dimethyl sulfoxide and the like.

The solid carrier may be, for example, a microparticle or a granule of kaolin clay, bentonite, acid clay, pyrophylite, talc, diatomaceous earth, calcite, urea, and ammonium sulfate.

The emulsifiers and the dispersing agents may be, for example, soaps, alkyl sulfonates, alkylaryl sulfonates, dialkyl sulfosuccinates, quaternary ammonium salts, oxyalkylamines, fatty acid esters, polyalkylene oxide-based surfactants, and anhydrosorbitol-based surfactants.

Although the content may vary depending on the dosage form and the purpose of use, the concentration may be set to 0.1% by mass to 99.9% by mass of the entire amount of the formulation in the case where Compound (I) is contained as an active ingredient in a formulation. Upon being used practically, it is preferable that a solvent, diluent, extender, and the like be added appropriately so that the treatment concentration is, for example, 0.005% by mass to 5% by mass, and preferably 0.01% by mass to 1% by mass.

Note that the agro-horticultural agent and the industrial material protecting agent may contain, as active ingredients, plural compounds which are encompassed in Compound (I).

As described above, an azole derivative represented by Compound (I) exhibits an excellent biocidal effect on a wide range of microorganisms which are pathogenic to plants. That is, the agro-horticultural disease controlling agent containing an azole derivative represented by Compound (I) as an active ingredient has a low toxicity to humans and animals, are capable of being handled safely, and exhibits a high controlling effect on a wide range of plant diseases.

Note that, since Compound (I) has a 1,2,4-triazolyl group or an imidazolyl group, Compound (I) forms an acid addition salt of an inorganic acid or an organic acid and a metal complex. Accordingly, Compound (I) can be employed also in the form of such an acid addition salt or the metal complex.

Furthermore, Compound (I) has at least three asymmetric carbon atoms. Thus, depending on a composition of Compound (I), Compound (I) is a stereoisomer mixture (enantiomer or diastereomer) or either one of the stereoisomers. Accordingly, at least one of these stereoisomers can be employed also as an active ingredient of an agro-horticultural agent and the like.

(Additional Remark)

The present invention is not limited to the description of the embodiments above, and can be modified in numerous ways by a skilled person as long as such modification falls within the scope of the claims. An embodiment derived from a proper combination of technical means disclosed in different embodiments is also encompassed in the technical scope of the present invention.

EXAMPLES

The invention will be embodied below with reference to Production Examples, Formulation Examples, and Test Examples. The invention is not limited to the following Production Examples, Formulation Examples, and Test Examples unless the inventions departs from its scope.

Production Example 1

Synthesis of (1RS,2RS,5SR)-5-(4-chlorobenzyl)-2-chloromethyl-2-methoxymethyl-1H-[1,2,4]triazole-1-ylmethylcyclopentanol (Compound No. I-16a (azole derivative (Ia'), $R^{10}=CH_3$, L=Cl, $X_m$=4-Cl, A=N), isomer type CC: (Production of a compound by performing Step 1A2 of the first method)

(1SR,4SR,5RS)-4-(4-chlorobenzyl)-1-methoxymethyl-5-(1H-[1,2,4]triazole-1-ylmethyl)-6-oxabicyclo-[3,2,0]heptane (Compound (IIa), $R^1$=CH$_3$, $X_m$=4-Cl, A=N, n1=1, n2=1, isomer type CC; similarly, azole derivative (IIa'), $R^{10}$=CH$_3$, $X_m$=4-Cl, A=N) (1.37 g) was dissolved in N,N-dimethylformamide (25 ml), and lithium chloride (2.25 g) and p-toluenesulfonic acid monohydrate (1.12 g) were added, and the resultant mixture was stirred at 80° C. for 2.2 hours. After the reaction, water was added to the mixture, and extraction was performed with use of ethyl acetate. An organic layer of the extract was washed with water and a saturated brine, and dried with use of anhydrous sodium sulfate. The solvent was distilled off, and the resultant crude product was purified by Silica gel column chromatography. The resultant slightly-yellow viscous liquid was recrystallized, and thus the desired substance was obtained.

Yield: 78%

The following compounds were synthesized in the same way as the compound in Production Example 1 described above.

(1RS,2RS,5RS)-5-(4-chlorobenzyl)-2-chloromethyl-2-methoxymethyl-1H-[1,2,4]triazole-1-ylmethylcyclopentanol (Compound No. I-16b (azole derivative (Ia'), $R^{10}$=CH$_3$, L=Cl, $X_m$=4-Cl, A=N)), isomer type CT $^1$H-NMR(CDCl$_3$)δ=1.31-1.40 (m,1H), 1.55-1.66 (m,1H), 1.79-1.92 (m,2H), 2.22-2.28 (m,2H), 2.80 (m,1H), 3.34 (s,3H), 3.49 (s,2H), 3.69 (d,J=11.0 Hz,1H), 3.74 (d,J=11.0 Hz,1H), 4.29 (s,1H), 4.49 (d,J=14.2 Hz,1H), 4.59 (d,J=14.2 Hz,1H), 6.96 (d,J=8.3 Hz,2H), 7.21 (d,J=8.5 Hz,2H), 8.00 (s,1H), 8.23 (s,1H).

(1RS,2RS,5SR)-5-(4-fluorobenzyl)-2-chloromethyl-2-methoxymethyl-1H-[1,2,4]triazole-1-ylmethylcyclopentanol (Compound No. I-170 (azole derivative (Ia'), $R^{10}$=CH$_3$, L=Cl, $X_m$=4-F, A=N))

$^1$H-NMR(CDCl$_3$)δ=1.35-1.42 (1H,m), 1.53-1.60 (2H,m), 1.85-1.93 (1H,m), 2.32-2.35 (1H,m), 2.43 (1H, dd,J=13.6,4.3 Hz), 2.57 (1H,dd,J=13.6,10.3 Hz), 3.04 (1H,d,J=10.5 Hz), 3.39 (3H,s), 3.43 (1H,d,J=10.4 Hz), 3.47 (1H,d,J=10.4 Hz), 3.55 (1H,d,J=10.5 Hz), 4.23 (1H,d,J=13.9 Hz), 4.58 (1H,d, 13.9 Hz), 4.76 (1H,s), 6.92-6.97 (2H,m), 7.06-7.09 (2H,m), 7.98 (1H,s), 8.12 (1H,s)

(1RS,2RS,5SR)-5-benzyl-2-chloromethyl-2-methoxymethyl-1H-[1,2,4]triazole-1-ylmethylcyclopentanol (Compound No. I-187 (azole derivative (Ia'), $R^{10}$=CH$_3$, L=Cl, $X_m$=unsubstituted, A=N))

$^1$H-NMR(CDCl$_3$)δ=1.34-1.41 (1H,m), 1.57-1.65 (2H,m), 1.85-1.93 (1H,m), 2.37-2.39 (1H,m), 2.48 (1H,dd,J=13.5,4.3 Hz), 2.60 (1H,dd,J=13.5,10.2 Hz), 3.02 (1H,d,J=10.4 Hz), 3.39 (3H,s), 3.43 (1H,d,J=10.5 Hz), 3.46, (1H,d,J=10.5 Hz), 3.55 (1H,d,J=10.4 Hz), 4.23 (1H,d,J=14.0 Hz), 4.58 (1H,d, 14.0 Hz), 4.77 (1H,s), 7.12-7.14 (2H,d J=7.0 Hz), 7.18-7.28 (3H,m), 7.98 (1H,s), 8.12 (1H,s)

(1RS,2RS,5SR)-5-(4-chlorobenzyl)-2-chloromethyl-2-ethoxymethyl-1H-[1,2,4]triazole-1-ylmethylcyclopentanol (Compound No. I-48 (azole derivative (Ia'), $R^{10}$=CH$_2$CH$_3$, L=Cl, $X_m$=4-Cl, A=N))

$^1$H-NMR(CDCl$_3$)δ=1.27 (3H,t,J=7.0 Hz), 1.34-1.42 (1H m), 1.48-1.66 (2H,m), 1.89 (1H,ddd,J=13.4,10.9,6.1 Hz), 2.29-2.39 (1H,m), 2.45 (1H,dd,J=13.6,3.6 Hz), 2.58 (1H,dd, J=13.6,10.2 Hz), 3.06 (1H,d,J=10.4 Hz), 3.44-3.59 (4H m), 3.45 (1H,d,J=10.4 Hz), 4.23 (1H,d,J=13.9 Hz), 4.65 (1H,d, J=13.9 Hz), 4.76 (1H,s), 7.06 (2H,d,J=8.4 Hz), 7.22 (2H,d, J=8.4 Hz), 7.98 (1H,s), 8.18 (1H,s).

(1RS,2RS,5SR)-5-(4-fluorobenzyl)-2-chloromethyl-2-ethoxymethyl-1H-[1,2,4]triazole-1-ylmethylcyclopentanol (Compound No. I-226 (azole derivative (Ia'), $R^{10}$=CH$_2$CH$_3$, L=Cl, $X_m$=4-F, A=N))

$^1$H-NMR(CDCl$_3$)δ=1.28 (3H,t,J=7.0 Hz), 1.37-1.41 (1H, m), 1.53-1.62 (2H,m), 1.86-1.94 (1H,m), 2.34-2.37 (1H,m), 2.46 (1H,dd,J=13.6,4.4 Hz), 2.58 (1H,dd,J=13.6,10.3 Hz), 3.05 (1H,d,J=10.4 Hz), 3.46 (1H,d,J=10.4 Hz), 3.50 (1H,d, J=10.4 Hz), 3.53-3.58 (3H,m), 4.23 (1H,d,J=13.9 Hz), 4.66 (1H,d,J=13.9 Hz), 4.78 (1H,s), 6.93-6.97 (2H,m), 7.07-7.10 (2H,m), 7.98 (1H,s), 8.19 (1H,s).

(1RS,2RS,5SR)-5-benzyl-2-chloromethyl-2-ethoxymethyl-1H-[1,2,4]triazole-1-ylmethylcyclopentanol (Compound No. I-234 (azole derivative (Ia'), $R^{10}$=CH$_2$CH$_3$, L=Cl, $X_m$=unsubstituted, A=N))

$^1$H-NMR(CDCl$_3$)δ=1.28 (3H,t,J=7.0 Hz), 1.34-1.41 (1H, m), 1.51-1.69 (2H,m), 1.86-1.94 (1H,m), 2.35-2.43 (1H, m), 2.52 (1H,dd,J=13.4,4.3 Hz), 2.62 (1H,dd,J=13.4,10.1 Hz), 3.04 (1H,d,J=10.4 Hz), 3.45-3.66 (5H,m), 4.24 (1H,d,J=13.9 Hz), 4.65 (1H,d,J=13.9 Hz), 4.80 (1H,s), 7.13-7.20 (3H,m), 7.25-7.28 (2H,m), 7.98 (1H,s), 8.19 (1H,s)

Production Example 2

Similarly, the following compounds were synthesized.

(1RS,2RS,5SR)-5-(4-fluorobenzyl)-2-bromomethyl-2-methoxymethyl-1H-[1,2,4]triazole-1-ylmethylcyclopentanol (Compound No. I-198 (azole derivative (Ia'), $R^{10}$=CH$_3$, L=Br, $X_m$=4-F, A=N))

$^1$H-NMR(CDCl$_3$) δ=1.33-1.40 (1H,m), 1.50-1.60 (2H,m), 1.86-1.94 (1H,m), 2.36-2.38 (1H,m), 2.49 (1H,dd,J=13.6,4.5

Hz), 2.60 (1H,dd,J=13.6,10.1 Hz), 2.86 (1H,d,J=9.6 Hz), 3.40 (3H,s), 3.45-3.47 (3H,m), 4.22 (1H,d,J=13.9 Hz), 4.58 (1H,d,J=13.9 Hz), 4.86 (1H,s), 6.93-6.97 (2H,m), 7.07-7.11 (2H,m), 7.98 (1H,s), 8.11 (1H,s).

(1RS,2RS,5SR)-5-benzyl-2-bromomethyl-2-methoxymethyl-1H-[1,2,4]triazole-1-ylmethylcyclopentanol (Compound No. I-203 (azole derivative (Ia'), $R^{10}$=CH$_3$, L=Br, $X_m$=unsubstituted, A=N)

$^1$H-NMR(CDCl$_3$)δ=1.33-1.40 (1H,m), 1.54-1.65 (2H,m), 1.86-1.94 (1H,m), 2.39-2.42 (1H,m), 2.54 (1H,dd,J=13.5,4.5 Hz), 2.63 (1H,dd,J=13.5,10.0 Hz), 2.84 (1H,d,J=9.6 Hz), 3.39 (3H,s), 3.46-3.48 (3H,m), 4.23 (1H,d,J=14.0 Hz), 4.57 (1H,d,J=14.0 Hz), 4.88 (1H,s), 7.14-7.20 (3H,m), 7.25-7.29 (2H,m), 7.98 (1H,s), 8.11 (1H,s).

Production Example 3

Synthesis of azole derivative (IIa') ($R^{10}$=CH$_3$, $X_m$=4-Cl, A=N): (Production of a compound by performing Step 1A1 of the first method))

(1SR,4SR,5RS)-4-(4-chlorobenzyl)-1-hydroxymethyl-5-(1H-[1,2,4]-triazole-1-ylmethyl)-6-oxabicyclo-[3,2,0]heptane (azole derivative (IIIa'), $X_m$=4-Cl, A=N) (50.0 mg) was dissolved in THF (1.5 ml), and sodium hydride (7.2 mg) was added. The mixture was stirred at a room temperature for 15 minutes. Iodomethane (0.0112 ml) was added to the mixture, and the resultant mixture was stirred at a room temperature for 1 hour. The mixture was then stirred at 50° C. for 3 hours. Further, iodomethane (0.0112 ml) was added and the resultant mixture was stirred at 50° C. for 5 hours. Then iodomethane (0.0112 ml) and sodium hydride (7.2 mg) were added, and the resultant mixture was stirred at a room temperature for 15 hours and stirred at 50° C. for 4 hours. Then iodomethane (0.0112 ml) and sodium hydride (7.2 mg) were added, and the resultant mixture was further stirred for 1.5 hours. After the reaction, water was added, then extraction was performed with use of ethyl acetate, and an extract was washed with a saturated brine solution. Then, an organic layer of the extract was dried with use of anhydrous sodium sulfate, and a solvent was distilled off. A residue was purified by Silica gel column chromatography, and thus the desired substance was obtained.

Yield: 81.3%

$^1$H-NMR(CDCl$_3$)δ=1.45-1.53 (1H,m), 1.57-1.64 (1H,m), 1.68-1.76 (1H,m), 1.81-1.94 (2H,m), 2.33 (1H,dd,J=13.5,4.0 Hz), 2.45 (1H,dd,J=13.5,9.6 Hz), 3.34 (1H,d,J=10.1 Hz), 3.38 (3H,s), 3.39 (1H,d,J=10.1 Hz), 4.14 (1H,d,J=6.1 Hz), 4.48 (1H,dd,J=6.1,1.3 Hz), 4.53 (1H,d,J=14.8 Hz), 4.73 (1H,d,J=14.8 Hz), 7.05 (2H,d,J=8.4 Hz), 7.21 (2H,d,J=8.4 Hz), 7.96 (1H,s), 8.16 (1H,s).

The following compounds were synthesized in the same way as the compound in Production Example 3 described above.

(1SR,4SR,5SR)-4-(4-chlorobenzyl)-1-methoxymethyl-5-(1H-[1,2,4]triazole-1-ylmethyl)-6-oxabicyclo-[3,2,0]heptane (azole derivative (IIa'), $R^{10}$=CH$_3$, $X_m$=4-Cl, A=N, isomer type CT)

$^1$H-NMR(CDCl$_3$)δ=1.57 (dd,J=12.8, 6.4 Hz, 1H), 1.67 (dd,J=13.4, 6.2 Hz, 1H), 1.97-2.01 (m, 2H), 2.14 (dd,J=12.6, 6.2 Hz, 1H), 2.17 (t-like, J=13.1 Hz, 1H), 3.02 (dd,J=13.1, 3.6 Hz, 1H), 3.36 (d,J=10.0 Hz, 1H), 3.42 (s, 3H), 3.54 (d,J=10.0 Hz, 1H), 4.08 (d,J=6.0 Hz, 1H), 4.49 (d,J=6.0 Hz, 1H), 4.64 (d,J=14.8 Hz, 1H), 4.89 (d,J=14.8 Hz, 1H), 6.96 (d,J=8.3 Hz, 2H), 7.22 (d,J=8.3 Hz, 2H), 7.96 (s,1H), 8.30 (s, 1H).

(1SR,4SR,5RS)-4-(4-fluorobenzyl)-1-methoxymethyl-5-(1H-[1,2,4]triazole-1-ylmethyl)-6-oxabicyclo-[3,2,0]heptane (azole derivative (IIa'), $R^{10}$=CH$_3$, $X_m$=4-F, A=N)

$^1$H-NMR(CDCl$_3$)δ=1.48-1.53 (1H,m), 1.61 (1H,dd,J=13.4,5.6 Hz), 1.71-1.74 (1H,m), 1.81-1.90 (2H,m), 2.36 (1H,dd,J=13.5,3.7 Hz), 2.46 (1H,dd,J=13.5,9.5 Hz), 3.35 (1H,d,J=10.1 Hz), 3.38 (3H,s), 3.39 (1H,d,J=10.1 Hz), 4.15 (1H,d,J=6.1 Hz), 4.48 (1H, dd,6.1,1.3 Hz), 4.53 (1H,d,14.8 Hz), 4.73 (1H,d,J=14.8 Hz), 6.91-6.96 (2H,m), 7.06-7.10 (2H,m), 7.96 (1H,s), 8.15 (1H,s)

(1SR,4SR,5RS)-4-benzyl-1-methoxymethyl-5-(1H-[1,2,4]triazole-1-ylmethyl)-6-oxabicyclo-[3,2,0]heptane (azole derivative (IIa'), $R^1$=CH$_3$, $X_m$=unsubstituted, A=N)

$^1$H-NMR(CDCl$_3$)δ=1.45-1.51 (1H,m), 1.61 (1H,dd,J=13.1,5.6 Hz), 1.75-1.79 (1H,m), 1.88-1.94 (2H,m), 2.45 (1H,dd,J=13.4,4.4 Hz), 2.52 (1H,dd,J=13.4,8.8 Hz), 3.35 (1H,d,J=10.0 Hz), 3.37 (3H,s), 3.42 (1H,d,J=10.0 Hz), 4.15 (1H,d,J=6.1 Hz), 4.47 (1H,d,6.1 Hz), 4.48 (1H,d,14.8 Hz), 4.70 (1H,d,J=14.8 Hz), 7.12-7.19 (3H,m), 7.24-7.27 (2H,m), 7.95 (1H,s), 8.05 (1H,s)

Production Example 4

Similarly, the following compounds were synthesized.

(1SR,4SR,5RS)-4-(4-fluorobenzyl)-1-ethoxymethyl-5-(1H-[1,2,4]triazole-1-ylmethyl)-6-oxabicyclo-[3,2,0]heptane (azole derivative (IIa'), $R^{10}$=CH$_2$CH$_3$, $X_m$=4-F, A=N)

$^1$H-NMR(CDCl$_3$)δ=1.23 (3H,t,J=7.0 Hz), 1.47-1.52 (1H,m), 1.60 (1H,dd,J=13.3,5.5 Hz), 1.69-1.74 (1H,m), 1.81-1.88 (2H,m), 2.32 (1H,dd,J=13.6,3.4 Hz), 2.44 (1H,dd,J=13.5,9.6 Hz), 3.41 (1H,d,J=10.2 Hz), 3.44 (1H,d,J=10.2 Hz), 3.51 (2H,qd,J=7.0,2.0 Hz), 4.15 (1H,d,J=6.0 Hz), 4.53 (1H,dd,J=6.0,1.2 Hz), 4.54 (1H,d,J=14.8 Hz), 4.78 (1H,d,J=14.8 Hz), 6.91-6.96 (2H,m), 7.06-7.10 (2H,m), 7.96 (1H,s), 8.17 (1H,s).

(1SR,4SR,5RS)-4-(4-chlorobenzyl)-1-ethoxymethyl-5-(1H-[1,2,4]triazole-1-ylmethyl)-6-oxabicyclo-[3,2,0]heptane (azole derivative (IIa'), $R^{10}$=CH$_2$CH$_3$, $X_m$=4-Cl, A=N)

$^1$H-NMR(CDCl$_3$)δ=1.23 (3H,t,J=7.0 Hz), 1.44-1.52 (1H,m), 1.56-1.63 (1H,m), 1.67-1.76 (1H,m), 1.81-1.94 (2H, m), 2.30 (1H,dd,J=13.4,3.9 Hz), 2.44 (1H,dd,J=13.4,9.7 Hz), 3.42 (1H,d,J=10.3 Hz), 3.43 (1H,d,J=10.3 Hz), 3.50 (2H,qd,J=7.0,2.0 Hz), 4.14 (1H,d,J=6.0 Hz), 4.52 (1H,dd,J=6.0,1.2 Hz), 4.55 (1H,d,J=14.8 Hz), 4.78 (1H,d,J=14.8 Hz), 7.06 (2H,d,J=8.4 Hz), 7.21 (2H,d,J=8.4 Hz), 7.95 (1H,s), 8.18 (1H,s)

(1SR,4SR,5RS)-4-benzyl-1-ethoxymethyl-5-(1H-[1,2,4]triazole-1-ylmethyl)-6-oxabicyclo-[3,2,0]heptane (azole derivative (IIa'), $R^{10}$=CH$_2$CH$_3$, $X_m$=unsubstituted, A=N)

$^1$H-NMR(CDCl$_3$)δ=1.22 (3H,t,J=7.0 Hz), 1.44-1.52 (1H,m), 1.61 (1H,dd,J=13.2,5.5 Hz), 1.74-1.78 (1H,m), 1.84-1.93

(2H,m), 2.42 (1H,dd,J=13.6,3.8 Hz), 2.50 (1H,dd,J=13.6,9.5 Hz), 3.40 (1H,d,J=10.1 Hz), 3.47 (1H,d,J=10.1 Hz), 3.49-3.51 (2H,m), 4.15 (1H,d,J=6.0 Hz), 4.50 (1H,d,J=14.8 Hz), 4.51 (1H,d,J=6.0 Hz), 4.76 (1H,d,J=14.8 Hz), 7.12-7.19 (3H, m), 7.24-7.26 (2H,m), 7.94 (1H,s), 8.07 (1H,s).

Production Example 5

Synthesis of azole derivative (IIIa') ($X_m$=4-Cl, A=N): (Production of a compound by performing Step 1C2 and Step 1B of the first method)

[Production of a Compound by Performing Step 1C2 of the First Method]

(cis, trans mixture)-2-(4-chlorobenzyl)-8,8-dimethyl-1-[1,2,4]triazole-1-ylmethyl7,9-dioxaspiro[4,5]decane-1-ol (azole derivative (V'), $R^6$=CH$_3$, $R^7$=CH$_3$, $X_m$=4-Cl, A=N) (359 mg) was dissolved in a 10% hydrogen chloride methanol solution, and was stirred at a room temperature for 23 hours. After the reaction, a solvent was distilled off, and water was added to a residue. A 2 mol/L sodium hydroxide aqueous solution was added to this suspension, and the resultant mixture was stirred at a room temperature for 15 minutes. The mixture was filtered to obtain a crystal, and the crystal was dried in vacuum to obtain 271.1 mg of (1SR,5RS)-5-(4-chlorobenzyl)-2,2-bishydroxymethyl-1-[1,2,4]triazole-1-ylmethylcyclopentanol(azole derivative (IV'), $X_m$=4-Cl, A=N). Yield 84.1%.

$^1$H-NMR(CDCl$_3$)δ=1.20-1.25 (1H,m), 1.43-1.61 (5H,m), 2.05-2.15 (2H,m), 2.40-2.48 (1H,m), 3.63 (1H,d,J=11.2 Hz), 3.75 (1H,d,J=14.0 Hz), 3.77 (1H,d,J=14.0 Hz), 3.86 (1H,d,J=11.2 Hz), 4.45 (1H,d,J=14.3 Hz), 4.75 (1H,d,J=14.3 Hz), 4.84 (1H,brs), 6.97 (2H,d,J=8.4 Hz), 7.20 (2H,d,J=8.4 Hz), 8.00 (1H,s), 8.24 (1H,s).

[Production of a Compound by Performing Step 1B of the First Method]

An azole derivative (IV') ($X_m$=4-Cl, A=N) (30.0 mg) was dissolve in tetrahydrofuran (0.9 ml), and was cooled to 0° C. in an ice bath. Sodium hydride (8.2 mg) was added to this solution, and the resultant mixture was stirred at 0° C. for 10 minutes. Further, p-toluene sulfonyl chloride (16.2 mg) was added, and the mixture was stirred for 2.5 hours while letting the temperature of the mixture back to a room temperature. After the reaction, water was added, and extraction was performed with use of ethyl acetate. An organic layer of the extract was washed with a saturated brine solution, and was dried with use of anhydrous sodium sulfate. A solvent was distilled off, and a residue was purified by Silica gel column chromatography. Thus the desired substance was obtained. Yield: 71.6%

$^1$H-NMR(CDCl$_3$)δ=1.46-1.58 (2H,m), 1.79-1.96 (3H,m), 2.61 (1H,dd,J=13.7,8.3 Hz), 2.67 (1H,dd,J=13.7,6.4 Hz), 3.45 (1H,dd,J=12.9,9.6 Hz), 3.94 (1H,dd,J=12.9,3.1 Hz), 4.14 (1H,d,J=6.3 Hz), 4.19 (1H,d,J=6.3 Hz), 4.22 (1H,d,J=15.0 Hz), 4.57 (1H,dd,J=9.6,3.1 Hz), 4.68 (1H,d,J=15.0 Hz), 7.01 (2H,d,J=8.4 Hz), 7.25 (2H,d,J=8.4 Hz), 7.70 (1H,s), 7.97 (1H,s).

Production Example 6

Similarly, the following compounds were synthesized.

(1SR,4SR,5SR)-4-(4-chlorobenzyl)-1-hydroxymethyl-5-(1H-[1,2,4]triazole-1-ylmethyl)-6-oxabicyclo-[3,2,0]heptane (azole derivative (IIIa'), $X_m$=4-Cl, A=N, isomer type CT)

$^1$H-NMR(CDCl$_3$)δ=1.58-1.67 (m,2H), 2.09-2.19(m,3H), 2.28 (dd-like,J=13.3,12.3 Hz,1H), 2.42 (bs,1H), 2.97 (dd-like,J=13.3,4.1 Hz,1H), 3.60 (d,J=4.4 Hz,2H), 4.06 (d,J=6.2 Hz,1H), 4.26 (d,J=6.2 Hz,1H), 4.61 (d,J=14.8 Hz,1H), 4.91 (d,J=14.8 Hz,1H), 7.01 (d,J=8.5 Hz,2H), 7.24 (d,J=8.5 Hz,2H), 7.99 (s, 1H), 8.35 (s, 1H).

1)

(1SR,5RS)-5-(4-fluorobenzyl)-2,2-bishydroxymethyl-1-[1,2,4]triazole-1-ylmethylcyclopentanol (azole derivative (IV'), $X_m$=4-F, A=N)

$^1$H-NMR(CDCl$_3$)δ=1.19-1.28 (1H,m), 1.47-1.60 (3H,m), 2.05-2.14 (2H,m), 2.44 (1H,dd,J=13.8,10.9 Hz), 2.91 (1H,t-like,J=5.7 Hz), 3.28 (1H,dd,J=6.3,4.8 Hz), 3.63 (1H,dd,J=11.2,5.6 Hz), 3.74-3.84 (2H, m), 3.87 (1H,dd,J=11.2,5.6 Hz), 4.45 (1H,d,J=14.3 Hz), 4.75 (1H,d,J=14.3 Hz), 4.83 (1H,s), 6.90-7.01 (4H,m), 8.00 (1H,s), 8.24 (1H,s)

2)

(1SR,4SR,5RS)-4-(4-fluorobenzyl)-1-hydroxymethyl-5-(1H-[1,2,4]triazole-1-ylmethyl)-6-oxabicyclo-[3,2,0]heptane (azole derivative (IIIa'), $X_m$=4-F, A=N)

$^1$H-NMR(CDCl$_3$)δ=1.47-1.56 (2H,m), 1.84-1.97 (3H,m), 2.62 (1H,dd,J=13.7,8.2 Hz), 2.69 (1H,dd,J=13.7,6. 4 Hz), 3.45 (1H,dd,J=12.9,9.9 Hz), 3.97 (1H,dd,J=12.9,3.5 Hz), 4.15 (1H,d,J=6.3 Hz), 4.19 (1H,d,J=6.3 Hz), 4.22 (1H,d,J=15.0 Hz), 4.67 (1H,d,J=15.0 Hz), 4.69 (1H,dd,J=9.9,3.5 Hz), 6.95-7.00 (2H,m), 7.01-7.05 (2H,m), 7.64 (1H,s), 7.97 (1H,s)

1)

(1SR,5RS)-5-benzyl-2,2-bishydroxymethyl-1-[1,2,4]triazole-1-ylmethylcyclopentanol(azole derivative (IV'), $X_m$=unsubstituted, A=N)

$^1$H-NMR(CDCl$_3$)δ=1.20-1.28 (1H,m), 1.47-1.61 (3H,m), 2.11-2.16 (1H,m), 2.20 (1H,dd,J=13.4,5.3 Hz), 2.48 (1H,dd,J=13.4,10.5 Hz), 2.98 (1H,t-like,J=5.8 Hz), 3.40 (1H,dd,J=6.5,4.7 Hz), 3.63 (1H,dd,J=11.3,5.7 Hz), 3.72-3.81 (2H, m), 3.87 (1H,dd,J=11.3,5.7 Hz), 4.44 (1H,d,J=14.3 Hz), 4.75 (1H,d,J=14.3 Hz), 4.81 (1H,s), 7.04-7.06 (2H,m), 7.14-7.18 (1H,m), 7.23-7.24 (1H,m), 8.00 (1H,s), 8.23 (1H,s)

2)

(1SR,4SR,5RS)-4-benzyl-1-hydroxymethyl-5-(1H-[1,2,4]triazole-1-ylmethyl)-6-oxabicyclo-[3,2,0]heptane (azole derivative (IIIa'), $X_m$=unsubstituted, A=N)

$^1$H-NMR(CDCl$_3$)δ=1.50-1.53 (2H,m), 1.91-1.99 (3H,m), 2.66 (1H,dd,J=13.6,7.1 Hz), 2.76 (1H,dd,J=13.6,7. 2 Hz), 3.44 (1H,dd,J=13.0,10.2 Hz), 4.03 (1H,dd,J=13.0,3.4 Hz), 4.16 (1H,d,J=6.3 Hz), 4.16 (1H,d,J=15.0 Hz), 4.19 (1H,d,J=6.3 Hz), 4.63 (1H,d,J=15.0 Hz), 4.94 (1H,dd,J=10.2,3.4 Hz), 7.08-7.10 (2H,m), 7.22-7.30 (3H,m), 7.23 (1H,s), 7.93 (1H,s)

Production Example 7

Synthesis 1 of 2-(4-chlorobenzyl)-8,8-dimethyl-1-[1,2,4]triazole-1-ylmethyl-7,9-dioxaspiro[4,5]decane-1-ol (Compound V'-a: azole derivative (V'), $R^6$=CH$_3$, $R^7$=CH$_3$, $X_m$=4-Cl, A=N): (Production of a compound by performing Step 1C1 of the first method)

[1,2,4]-triazolesodium salt (1.14g) was dissolved in N-methylpyrrolidinone (6.4 ml), and heated to an internal temperature of 115° C. 2-(4-chlorobenzyl)-8,8-dimethyl-7,9-dioxaspiro[4,5]decane-1-on (azole derivative (VIII'), $R^6$=CH$_3$, $R^7$=CH$_3$, $X_m$=4-Cl, A=N) (2.59 g) was added to this, and the mixture was washed thoroughly with N-methylpyrrolidinone (2.0 ml). After the internal temperature was back to 115° C., sodium t-butoxide (725 mg) and TMSOB (2.77 g) were gradually added over 12.5 hours. Then the mixture was stirred for 5 hours. The resultant reaction solution was cooled to a room temperature, then water was added, and extraction was performed with use of ethyl acetate. An organic layer of the extract was washed with water and a saturated brine solution, and was dried with use of anhydrous sodium sulfate. The solvent was distilled off, and the resultant crude product was purified by Silica gel column chromatography. Thus the desired substance was produced as a mixture containing 7% of trans isomers. Here, "cis isomer" and "trans isomer" are based on a steric configuration regarding how a hydroxy group and a benzyl group are attached to a cyclopentane ring of the azole derivative (V'). Also in Production Examples described below, "cis isomer" and "trans isomer" in each compound are based on a steric configuration regarding a group corresponding to the hydroxy group and a group corresponding to the benzyl group which are attached to the ring.

Yield: 55.0%

Cis Isomer $^1$H-NMR(CDCl$_3$)δ=1.22-1.32 (1H,m), 1.32-1.41 (1H,m), 1.39 (3H,s), 1.46 (3H,s), 1.46-1.62 (3H,m), 2.13-2.20 (1H, m), 2.25-2.33 (1H,m), 3.68 (1H,d,J=12.0 Hz), 3.76 (1H,d, J=12.6 Hz), 3.87 (1H,dd,J=12.6,2.1 Hz), 4.20 (1H,dd,J=12.0, 2.1 Hz), 4.26 (1H,s), 4.60 (1H,d,J=14.4 Hz), 4.79 (1H,d, J=14.4 Hz), 6.90 (2H,d,J=8.3 Hz), 7.16 (2H,d,J=8.3 Hz), 8.02 (1H,s), 8.29 (1H,s).

Trans Isomer $^1$H-NMR(CDCl$_3$)δ=1.22-1.60 (3H,m), 1.38 (3H,s), 1.47 (3H,s), 1.65-1.80 (1H,m), 2.10-2.21 (2H,m), 2.72-2.86 (1H, m), 3.67 (1H,d,J=12.0 Hz), 3.75 (1H,d,J=12.5 Hz), 3.97 (1H, dd,J=12.5,2.5 Hz), 4.25 (1H,dd,J=12.0,2.5 Hz), 4.65-4.75 (3H,m), 6.90 (2H,d,J=8.3 Hz), 7.13-7.23 (2H,m), 8.00 (1H,s), 8.39 (1H,s).

The following compounds were synthesized in the same way as the compound in Production Example 7 described above.

2-(4-fluorobenzyl)-8,8-dimethyl-1-[1,2,4]triazole-1-ylmethyl-7,9-dioxaspiro[4,5]decane-1-ol (azole derivative (V'), $R^6$=CH$_3$, $R^7$=CH$_3$, $X_m$=4-F, A=N)

$^1$H-NMR(CDCl$_3$)δ=1.24-1.29 (1H,m), 1.39 (3H,s), 1.35-1.42 (1H,m), 1.46 (3H,s), 1.46-1.61 (3H,m), 2.16 (1H,dd, J=13.2,11.3 Hz), 2.26-2.34 (1H,m), 3.68 (1H,d,J=12.0 Hz), 3.76 (1H,d,J=12.6 Hz), 3.88 (1H,dd,J=12.6,2.2 Hz), 4.20 (1H,dd,J=12.0,2.2 Hz), 4.28 (1H,s), 4.62 (1H,d,J=14.4 Hz), 4.80 (1H,d,J=14.4 Hz), 6.86-6.94 (4H,m), 8.02 (1H,s), 8.30 (1H,s)

2-benzyl-8,8-dimethyl-1-[1,2,4]triazole-1-ylmethyl-7,9-dioxaspiro[4,5]decane-1-ol(azole derivative (V'), $R^6$=CH$_3$, $R^7$=CH$_3$, $X_m$=unsubstituted, A=N)

$^1$H-NMR(CDCl$_3$)δ=1.26-1.31 (1H,m), 1.28 (3H,s), 1.40-1.44 (1H,m), 1.46 (3H,s), 1.52-1.61 (3H,m), 2.19 (1H,dd, J=13.2,11.3 Hz),2.29-2.37 (1H,m), 3.67 (1H,d,J=12.0 Hz), 3.75 (1H,d,J=12.5 Hz), 3. 89 (1H,dd,J=12.5,2.2 Hz), 4.19 (1H,dd,J=12.0,2.2 Hz), 4.26 (1H,s), 4.62 (1H,d,J=14.5 Hz), 4.79 (1H,d,J=14.5 Hz), 6.97-6.98 (2H,m), 7.11-7.15 (H,m), 7.19-7.22 (2H,m), 8.02 (1H,s), 8.30 (1H,s)

Production Example 8

Synthesis 1 of 2-(4-chlorobenzyl)-8,8-dimethyl-7,9-dioxaspiro[4,5]decane-1-on (Compound (VIII'), $R^6$=CH$_3$, $R^7$=CH$_3$, $X_m$=4-Cl): (Production of a compound by performing Step 1D of the first method)

Potassium carbonate (3.5 g) and 12 ml of aqueous solution of formaldehyde were added to methyl 1-(4-chlorobenzyl)-2-oxocyclopentanecarboxylic acid (Compound (XII), $X_m$=4-Cl, $R^4$=CH$_3$) (13.34 g), and the mixture was vigorously stirred at a room temperature for 7 hours. After the reaction, water was added, and extraction was performed with use of ethyl acetate. An organic layer of the extract was washed with a saturated brine solution, and was dried with use of anhydrous sodium sulfate. The solvent was distilled off, to obtain a crude product of methyl 1-(4-chlorobenzyl)-3,3-bis(hydroxylmethyl)-2-oxocyclopentane carboxylic acid (Compound (X'), $R^4$=CH$_3$, $X_m$=4-Cl). This crude product was dissolved in acetone (26 ml), and acetonedimethylacetal (Compound (XIV), $R^6$=CH$_3$, $R^7$=CH$_3$, $R^8$=CH$_3$, $R^9$=CH$_3$) (33 ml), and p-toluenesulfonic acid monohydrate (1.5 g) were added. The resultant mixture was stirred at a room temperature for 2.7 hours. After the reaction, an aqueous saturated sodium hydrogen carbonate was added, and then a white solid was deposited. Extraction was performed with use of ethyl acetate, then an organic layer of the extract was washed with a saturated brine solution and was dried with use of anhydrous sodium sulfate. The solvent was distilled off, to obtain a crude product of methyl 2-(4-chlorobenzyl)-8,8-dimethyl-1-oxo-7,9-dioxaspiro[4,5]decane-2-carboxylate (Compound (IX'), $X^6$=CH$_3$, $X^7$=CH$_3$, $X_m$=4-Cl, $R^4$=CH$_3$).

$^1$H-NMR(CDCl$_3$)δ=1.33 (s,3H), 1.45 (s,3H), 1.97-2.13 (m,4H), 2.33-2.38 (m,1H), 2.78 (dd,J=11.6,2.4 Hz, 1H), 3.04 (d,J=14.6 Hz,1H), 3.20 (d,J=14.6 Hz,1H), 3.55 (dd,J=11.2, 2.6 Hz, 1H), 3.71 (s,3H), 4.06 (d,J=11.2 Hz, 1H), 7.00 (d,J=8.4 Hz,2H), 7.22 (d,J=8.4 Hz,2H).

Toluene (1.1 ml) was added to the crude product of Compound (IX') ($X^6$=CH$_3$, $X^7$=CH$_3$, $X_m$=4-Cl, $R^4$=CH$_3$), and further 25% sodium hydroxide aqueous solution (36 ml) was added. Then the resultant mixture was heated at 98° C. for 3 hours under stirring. After the reaction, water and a small amount of 2N HCl aqueous solution was added, and extraction was performed with use of ethyl acetate. An organic layer of the extract was washed with water and a saturated brine solution, and was dried with use of anhydrous sodium sulfate. The solvent was distilled off, and the resultant crude product was purified by Silica gel column chromatography. Thus the desired substance was obtained.

Yield: 58%

$^1$H-NMR(CDCl$_3$)δ=1.37 (s,3H), 1.49 (s,3H), 1.53-1.57 (m,1H), 1.83-1.88 (m,1H), 2.04-2.10 (m,1H), 2.39-2.50 (m,2H), 2.60 (dd,J=14.0,8.4 Hz,1H), 3.00 (dd,J=14.0,4.4 Hz,1H), 3.24 (dd,J=11.4,2.6 Hz, 1H), 3.47 (dd,J=11.4,2.6 Hz,1H), 3.78 (dd,J=11.4,2.0 Hz,1H), 4.14 (d,J=11.4 Hz,1H), 7.05 (d,J=8.4 Hz,2H), 7.23 (d,J=8.4 Hz,2H).

Production Example 9

Similarly, the following compound was synthesized.

2-(4-fluorobenzyl)-8,8-dimethyl-7,9-dioxaspiro[4,5]decane-1-on (Compound (VIII'), $X^6$=CH$_3$, $X^7$=CH$_3$, $X_m$=4-F)

$^1$H-NMR(CDCl$_3$)δ=1.37 (3H,s), 1.49 (3H,s), 1.52-1.60 (1H,m), 1.80-1.88 (1H,m), 2.04-2.12 (1H,m), 2.39-2.50 (2H, m), 2.62 (1H,dd,J=13.9,8.3 Hz), 3.00 (1H,dd,J=13.9,4.6 Hz), 3.22 (1H,dd,J=11.4,2.6 Hz), 3.47 (1H,dd,J=11.4,2.6 Hz), 3.77 (1H,dd,J=11.4,1.6 Hz), 4.15 (1H,d,J=11.4 Hz), 6.93-6.97 (2H,m), 7.06-7.09 (2H,m)

Production Example 10

Similarly, the following compound was synthesized.

2-benzyl-8,8-dimethyl-7,9-dioxaspiro[4,5]decane-1-on (Compound (VIII'), $X^6$=CH$_3$, $X^7$=CH$_3$, $X_m$=unsubstituted)

$^1$H-NMR(CDCl$_3$)δ=1.37 (3H,s), 1.49 (3H,s), 1.52-1.63 (1H,m), 1.82-1.87 (1H,m), 2.06-2.11 (1H,m), 2.37-2.43 (1H, m), 2.45-2.53 (1H,m), 2.61 (1H,dd,J=13.7,8.6 Hz), 3.04 (1H, dd,J=13.7,4.3 Hz), 3.24 (1H,dd,J=11.4,2.6 Hz), 3.47 (1H,dd, J=11.4,2.6 Hz), 3.79 (1H,dd,J=11.4,1.6 Hz), 4.15 (1H,d, J=11.4 Hz), 7.12 (2H,d,J=6.8 Hz), 7.20 (1H,t,J=7.3 Hz), 7.25-7.29 (2H,m).

Production Example 11

Synthesis 2 of Compound (VIII') ($R^6$=CH$_3$, $R^7$=CH$_3$, $X_m$=4-Cl)

(1) Synthesis of Compound X'-a Which is Compound (X') Wherein $R^4$=CH$_3$, $X_m$=4-Cl Compound (XII) ($R^4$=CH$_3$, $X_m$=4-Cl) (79.98 g) was added to tetrahydrofuran (250 ml), and potassium carbonate (10.38 g) and a 37% formaldehyde aqueous solution (65 ml) were added to this. The resultant mixture was stirred at a room temperature for 23 hours. Water (250 ml) and a concentrated hydrochloric acid (51 ml) were added to the resultant reaction solution, and then the resultant mixture was further stirred for 7 hours. After the reaction, water was added, and extraction was performed with use of ethyl acetate. An organic layer of the extract was washed with water and a saturated brine solution, and was dried with use of anhydrous sodium sulfate. The solvent was distilled off. Thus a crude extract of Compound X'-a was obtained.
(2) Synthesis of Compound IX'-a Which is Compound (IX') Wherein $R^4$=CH$_3$, $R^6$=CH$_3$, $R^7$=CH$_3$, $X_m$=4-Cl Acetonedimethylacetal (Compound (XIV), $R^6$=CH$_3$, $R^7$=CH$_3$, $R^8$=CH$_3$, $R^9$=CH$_3$) (90 ml), toluene (180 ml), and p-toluenesulfonic acid monohydrate (1.43 g) were added to a whole quantity of the crude extract of Compound X'-a obtained in the above (1), and the resultant mixture was stirred at 55° C. for 1 hour, and then was further stirred at a room temperature for 15 hours. Sodium bicarbonate and toluene were added to the resultant reaction solution, and were partitioned. An aqueous layer was extracted with use of toluene, and then an organic layer of the extract was dried with use of anhydrous sodium sulfate. The solvent was distilled off. Thus, a crude extract of Compound IX'-a was obtained.

1H-NMR(CDCl$_3$)δ=1.33 (3H,s), 1.45 (3H,s), 1.97-2.13 (4H,m), 2.33-2.38 (1H,m), 2.78 (1H,dd,J=11.6,2.4 Hz), 3.04 (1H,d,J=14.6 Hz), 3.20 (1H,d,J=14.6 Hz), 3.55 (1H,dd, J=11.2,2.6 Hz), 3.71 (3H,s), 4.06 (1H,d,J=11.2 Hz), 7.00 (2H,d,J=8.4 Hz), 7.22 (2H,d,J=8.4 Hz).
(3) Synthesis of Compound VIII'-a which is Compound (VIII') wherein $R^6$=CH$_3$, $R^7$=CH$_3$, $X_m$=4-Cl Toluene (8 ml) was added to the crude extract of Compound IX'-a obtained in the above (2), and the resultant mixture was heated to 100° C. so that Compound IX'-a is dissolved in the toluene. 25 wt % sodium hydroxide aqueous solution (80.0 g) was added to the mixture, was reacted for 2 hours under reflux, and was let stand so as to be cooled. Water was added to the resultant reaction solution, and extraction was performed with use of toluene. An organic layer of the extract was washed with aqueous ammonium chloride, and was dried with use of anhydrous sodium sulfate. The solvent was distilled off. Thus Compound VIII'-a was obtained.

Yield: 69.0% (Yield after 3 steps from Compound (XII))
$^1$H-NMR(CDCl$_3$)δ=1.37 (3H,s), 1.49 (3H,s), 1.53-1.57 (1H,m), 1.83-1.88 (1H,m), 2.04-2.10 (1H,m), 2.39-2.50 (2H, m), 2.60 (1H,dd,J=14.0,8.4 Hz), 3.00 (1H,dd,J=14.0,4.4 Hz), 3.24 (1H,dd,J=11.4,2.6 Hz), 3.47 (1H,dd,J=11.4,2.6 Hz), 3.78 (1H,dd,J=11.4,2.0 Hz), 4.14 (1H,d,J=11.4 Hz), 7.02-7.10 (2H,m), 7.21-7.27 (2H,m).

Production Example 12

Synthesis 2 of Compound V'-a

Sodium hydride (0.91 g) was suspended in NMP (8 ml), and 1,2,4-triazole (1.67 g) was added to the resultant suspension and was stirred for 0.5 hour. Thus sodium salt of 1,2,4-triazole was produced. Compound VIII'-a (5.00 g) was added to the sodium salt, and the mixture was heated to 90° C. (bath temperature). Then TMSOB (4.20 g) and t-BuONa (0.77 g) were added intermittently to the mixture over 1.5 hours, and then the mixture was reacted for 1.5 hours. The resultant reaction solution was heated to 125° C. (bath temperature), and was reacted for 1 hour. An ammonium chloride aqueous solution was added to the resultant reaction solution, and extraction was performed with use of ethyl acetate. An organic layer of the extract was dried with use of anhydrous sodium sulfate, and the solvent was distilled off. A resultant crude product was purified by Silica gel column. Thus Compound V'-a was obtained as an isomer mixture (cis isomer: trans isomer=93:7).

Yield: 74.3%

Production Example 13

Synthesis 3 of Compound V'-a

NMP (2 ml) was added to a mixture of Compound VIII'-a (1.00 g), 1,2,4-triazole sodium salt (0.442 g), and TMSOB (0.785 g), and then the resultant mixture was heated to 85° C. under an argon atmosphere. To the mixture, t-BuONa (0.157 g) was added intermittently over 50 minutes, and then the resultant mixture was reacted for 50 minutes.

Water was added to the resultant reaction solution, and extraction was performed with use of ethyl acetate. An organic layer of the extract was washed with water and a saturated brine solution, and was dried with use of anhydrous sodium sulfate. The solvent was distilled off, and the resultant crude product was purified by Silica gel column. Thus Compound V'-a was obtained as an isomer mixture (cis isomer: trans isomer=94:6).

Yield: 80%

Production Example 14

Synthesis 4 of Compound V'-a

NMP (8 ml) was added to a mixture of Compound VIII'-a (5.00 g), 1,2,4-triazole sodium salt (1.92 g), and TMSOB (3.36 g), and the resultant mixture was heated to 85° C. under an argon atmosphere. Here, t-BuONa (0.94 g) was added, and then the resultant mixture was reacted for 3 hours, then was stirred at 115° C. for 15 minutes.

Water was added to the reaction solution, and extraction was performed with use of toluene. An organic layer of the extract was washed with water, and was dried with use of anhydrous sodium sulfate. The solvent was distilled off, and the resultant crude product was purified by Silica gel column. Thus Compound V'-a was obtained as isomer mixture (cis isomer:trans isomer=92:8).

Yield: 70%

Production Example 15

Synthesis of 5-(4-chlorobenzyl)-2,2-bis(hydroxylmethyl)-1-(1H-1,2,4-triazole-1-ylmethyl)cyclopentanol (azole derivative (IV') which is Compound IV'-a wherein $X_m$=4-Cl, A=N)

Compound V'-a (8.98 g) was dissolved in a solution mixture of methanol (30 ml) and 6N hydrochloric acid aqueous solution (40 ml), and the resultant mixture was stirred at a room temperature for 4 hours. Water was added to the resultant reaction solution, and then the resultant mixture was neutralized with use of sodium carbonate and sodium hydrogen carbonate. Extraction was performed with use of ethyl acetate, and an organic layer of the extract was washed with a saturated brine solution (100 ml). The organic layer was dried with use of anhydrous sodium sulfate, and the solvent was distilled off. Thus Compound IV'-a was obtained as an isomer mixture.

Yield: 98.7%

As to $^1$H-NMR values, only that of a cis isomer of Compound IV'-a is described below.

$^1$H-NMR(CDCl$_3$)δ=1.20-1.25 (1H,m), 1.43-1.61 (5H,m), 2.05-2.15 (2H,m), 2.40-2.48 (1H,m), 3.63 (1H,d,J=11.2 Hz), 3.75 (1H,d,J=14.0 Hz), 3.77 (1H,d,J=14.0 Hz), 3.86 (1H,d, J=11.2 Hz), 4.45 (1H,d,J=14.3 Hz), 4.75 (1H,d,J=14.3 Hz), 4.84 (1H,brs), 6.97 (2H,d,J=8.4 Hz), 7.20 (2H,d,J=8.4 Hz), 8.00 (1H,s), 8.24 (1H,s).

Production Example 16

Synthesis 2 of 2-benzyl-8,8-dimethyl-7,9-dioxaspiro [4,5]decane-1-on (Compound VIII'-b which is Compound (VIII') wherein $R^6$=CH$_3$, $R^7$=CH$_3$, $X_m$=unsubstituted)

Synthesis was performed in the same way as Production Example 11 except that methyl 1-benzyl-2-oxocyclopentanecarboxylate (Compound (XII), $R^4$=CH$_3$, $X_m$=unsubstituted) was used instead of Compound (XII) ($R^4$=CH$_3$, $X_m$=4-Cl), to thereby obtain Compound VIII'-b. A $^1$H-NMR value of the resultant compound is described below.

$^1$H-NMR(CDCl$_3$)δ=1.37 (3H,s), 1.49 (3H,s), 1.52-1.63 (1H,m), 1.82-1.87 (1H,m), 2.06-2.11 (1H,m), 2.37-2.43 (1H, m), 2.45-2.53 (1H,m), 2.61 (1H,dd,J=13.7,8.6 Hz), 3.04 (1H, dd,J=13.7,4.3 Hz), 3.24 (1H,dd,J=11.4,2.6 Hz), 3.47 (1H,dd, J=11.4,2.6 Hz), 3.79 (1H,dd,J=11.4,1.6 Hz), 4.15 (1H,d, J=11.4 Hz), 7.12 (2H,d,J=6.8 Hz), 7.20 (1H,t,J=7.3 Hz), 7.25-7.29 (2H m).

Production Example 17

Synthesis of 2-benzyl-8,8-dimethyl-1-(1H-1,2,4-triazole-1-ylmethyl)-7,9-dioxaspiro[4,5]decane-1-ol (Azole derivative (V') which is Compound V'-b wherein $R^6$=CH$_3$, $R^7$=CH$_3$, $X_m$=unsubstituted, A=N)

1,2,4-triazole sodium salt (0.973 g) was dissolved in NMP (4 ml), and was heated to 115° C. (internal temperature). Compound VIII'-b (1.96 g) dissolved in NMP (3 ml) was added. TMSOB (1.55 g) and t-BuONa (0.363 g) were added intermittently to the mixture over 2 hours at 115° C., and the resultant mixture was reacted for 0.5 hour. The resultant reaction solution was heated to 125° C. (bath temperature), and was reacted for 1 hour. After the reaction, a saturated brine solution is added to the reaction solution, and extraction was performed with use of ethyl acetate. An organic layer of the extract was washed with a saturated brine solution, and was dried with use of anhydrous sodium sulfate. The solvent was distilled off, and the resultant crude product was obtained by Silica gel column. Thus Compound V'-b was obtained as an isomer mixture (cis isomer:trans isomer=94:6).

Yield: 78.9%

As to $^1$H-NMR values, only that of a cis isomer of Compound V'-b is described below.

$^1$H-NMR(CDCl$_3$)δ=1.26-1.31 (1H,m), 1.28 (3H,s), 1.40-1.44 (1H,m), 1.46 (3H,s), 1.52-1.61 (3H,m), 2.19 (1H,dd, J=13.2,11.3 Hz),2.29-2.37 (1H,m),3.67 (1H,d,J=12.0 Hz), 3.75 (1H,d,J=12.5 Hz), 3.89 (1H,dd,J=12.5,2.2 Hz), 4.19 (1H,dd,J=12.0,2.2 Hz), 4.26 (1H,s), 4.62 (1H,d,J=14.5 Hz), 4.79 (1H,d,J=14.5 Hz), 6.97-6.98 (2H,m), 7.11-7.15 (1H,m), 7.19-7.22 (2H,m), 8.02 (1H,s), 8.30 (1H,s)

Production Example 18

Synthesis of 5-benzyl-2,2-bis(hydroxymethyl)-1-(1H-1,2,4-triazole-1-ylmeth yl)cyclopentanol (azole derivative (IV') which is Compound IV'-b wherein $X_m$=unsubstituted, A=N)

Synthesis was performed in the same way as Production Example 15 except that Compound V'-b was used instead of Compound V'-a. Thus 5-benzyl-2,2-bis(hydroxymethyl)-1-(1H-1,2,4-triazole-1-ylmeth yl)cyclopentanol (Compound IV'-b) was obtained. A $^1$H-NMR value of the resultant compound is described below.

$^1$H-NMR(CDCl$_3$)δ=1.20-1.28 (1H,m), 1.47-1.61 (3H,m), 2.11-2.16 (1H,m),2.20 (1H,dd,J=13.4,5.3 Hz), 2.48 (1H,dd, J=13.4,10.5 Hz), 2.98 (1H,t-like,J=5.8 Hz), 3.40 (1H,dd, J=6.5,4.7 Hz), 3.63 (1H,dd,J=11.3,5.7 Hz), 3.72-3.81 (2H, m), 3.87 (1H,dd,J=11.3,5.7 Hz), 4.44 (1H,d,J=14.3 Hz), 4.75 (1H,d,J=14.3 Hz), 4.81 (1H,s), 7.04-7.06 (2H,m), 7.14-7.18 (1H,m), 7.23-7.24 (2H,m), 8.00 (1H,s), 8.23 (1H,s).

Production Example 19

Synthesis of 2-(4-fluorobenzyl)-8,8-dimethyl-7,9-dioxaspiro[4,5]decane-1-on (Compound VIII'-c which is Compound (VIII') wherein $R^6$=CH$_3$, $R^7$=CH$_3$, $X_m$=4-F)

Synthesis was performed in the same way as Production Example 11 except that methyl 1-(4-fluorobenzyl)-2-oxocyclopentanecarboxylate (Compound (XII), $R^4$=CH$_3$, $X_m$=4-F) was used instead of Compound (XII) ($R^4$=CH$_3$, $X_m$=4-Cl), to thereby obtain Compound VIII'-c. A $^1$H-NMR value of the resultant compound is described below.

$^1$H-NMR(CDCl$_3$)δ=1.37 (3H,s), 1.49 (3H,s), 1.52-1.60 (1H,m), 1.80-1.88 (1H,m), 2.04-2.12 (1H,m), 2.39-2.50 (2H, m), 2.62 (1H,dd,J=13.9,8.3 Hz), 3.00 (1H,dd,J=13.9,4.6 Hz), 3.22 (1H,dd,J=11.4,2.6 Hz), 3.47 (1H,dd,J=11.4,2.6 Hz), 3.77 (1H,dd,J=11.4,1.6 Hz), 4.15 (1H,d,J=11.4 Hz), 6.93-6.97 (2H,m), 7.06-7.09 (2H,m).

Production Example 20

Synthesis of 2-(4-fluorobenzyl)-8,8-dimethyl-1-(1H-1,2,4-triazole-1-ylmethyl)-7,9-dioxaspiro[4,5]decane-1-ol (azole derivative (V')) which is Compound V'-c wherein $R^6$=$CH_3$, $R^7$=$CH_3$, $X_m$=4-F, A=N)

Synthesis was performed in the same way as Production Example 17 except that Compound VIII'-c was used instead of compound VIII'-b, to thereby obtain Compound V'-c as an isomer mixture.

As to $^1$H-NMR values, only that of a cis isomer of Compound V'-c is described below.
$^1$H-NMR(CDCl$_3$)δ=1.24-1.29 (1H,m), 1.39 (3H,s), 1.35-1.42 (1H,m), 1.46 (3H,s), 1.46-1.61 (3H,m), 2.16 (1H,dd, J=13.2,11.3 Hz), 2.26-2.34 (1H,m), 3.68 (1H,d,J=12.0 Hz), 3.76 (1H,d,J=12.6 Hz), 3.88 (1H,dd,J=12.6,2.2 Hz), 4.20 (1H,dd,J=12.0,2.2 Hz), 4.28 (1H,s), 4.62 (1H,d,J=14.4 Hz), 4.80 (1H,d,J=14.4 Hz), 6.86-6.94 (4H,m), 8.02 (1H,s), 8.30 (1H,s).

Production Example 21

Synthesis of 5-(4-fluorobenzyl)-2,2-bis(hydroxylmethyl)-1-(1H-1,2,4-triazole-1-ylmethyl)cyclopentanol (azole derivative (IV') which is Compound IV'-c wherein $X_m$=4-F, A=N)

Synthesis was performed in the same way as Production Example 15 except that Compound V'-c was used instead of Compound V'-a, to thereby obtain Compound IV'-c as an isomer mixture. As to $^1$H-NMR values, only that of a cis isomer of Compound IV'-c is described below.
$^1$H-NMR(CDCl$_3$)δ=1.19-1.28 (1H,m), 1.47-1.60 (3H,m), 2.05-2.14 (2H,m), 2.44 (1H,dd,J=13.8,10.9 Hz), 2.91 (1H,t-like,J=5.7 Hz), 3.28 (1H,dd,J=6.3,4.8 Hz), 3.63 (1H,dd, J=11.2,5.6 Hz), 3.74-3.84 (2H,m), 3.87 (1H,dd,J=11.2,5.6 Hz), 4.45 (1H,d,J=14.3 Hz), 4.75 (1H,d,J=14.3 Hz), 4.83 (1H,s), 6.90-7.01 (4H,m), 8.00 (1H,s), 8.24 (1H,s).

Production Example 22

Synthesis of 2-(4-chlorobenzyl)-7,9-dioxaspiro[4,5]decane-1-on (Compound VIII'-d which is Compound (VIII') wherein $R^6$=H, $R^7$=H, $X_m$=4-Cl)

(1) Synthesis of methyl 2-(4-chlorobenzyl)-1-oxo-7,9-dioxaspiro[4,5]decane-2-carboxylate (Compound IX'-d which is Compound (IX') wherein $R^4$=$CH_3$, $R^6$=H, $R^7$=H, $X_m$=4-Cl)

Compound X'-a (1.00 g) prepared in Production Example 11-(1) was dissolved in chloroform (4 ml) and dimethoxymethane (4 ml), and p-toluenesulfonic acid monohydrate (58.2 mg) and lithium chloride (53.2 mg) were added. The resultant mixture was stirred at a room temperature for 1.5 hours. After the reaction, an aqueous saturated sodium hydrogen carbonate was added to the mixture and extraction was performed with use of chloroform. An organic layer of the extract was washed with a saturated brine solution, and was dried with use of anhydrous sodium sulfate. Then the solvent was concentrated, and was dried in vacuum. Thus an intermediate crude product (1.28 g) was obtained. The intermediate crude product (100 mg) was dissolved in toluene (3 ml), and p-toluenesulfonic acid monohydrate (2.7 mg) was added. The resultant mixture was stirred at 100° C. for 9 hours. After the reaction, an aqueous saturated sodium hydrogen carbonate was added to the resultant mixture, and extraction was performed with use of toluene. An organic layer of the extract was washed with a saturated brine solution, and was dried with use of anhydrous sodium sulfate. The solvent was distilled off, and the residue was purified by Silica gel column chromatography. Thus Compound IX'-d was obtained (yield 74.9%).
$^1$H-NMR(400MHz,CDCl$_3$):δ=1.90-2.03 (2H,m), 2.10-2.20 (1H,m), 2.32-2.39 (1H,m), 3.00 (1H,dd,J=11.1,1.9 Hz), 3.05 (1H,d,J=13.8 Hz), 3.20 (1H,d,J=13.8 Hz), 3.42 (1H,dd,J=11.1,1.1 Hz), 3.72 (3H,s), 3.77 (1H,dd,J=11.1,2.1 Hz), 3.82 (1H,d,J=11.1 Hz), 4.61 (1H,d,J=6.1 Hz), 4.91 (1H, d,J=6.1 Hz), 7.01 (2H,d,J=8.5 Hz), 7.23 (2H,d,J=8.5 Hz).

(2) Synthesis of Compound VIII'-d

Toluene (0.065 ml) and a 1 mol/L sodium hydroxide aqueous solution (1.88 ml) were added to Compound IX'-d (640 mg), and was refluxed for 2.5 hours. A 1 mol/L sodium hydroxide aqueous solution (0.94 ml) was added, and the resultant mixture was further refluxed for 4 hours. After the reaction, extraction was performed with use of toluene. An organic layer of the extract was washed with a saturated brine solution, and was dried with use of anhydrous sodium sulfate. The solvent was distilled off, and the residue was purified by Silica gel column chromatography. Thus Compound VIII'-d was obtained (yield 72.7%).
$^1$H-NMR(400MHz,CDCl$_3$):δ=1.51-1.59 (1H,m), 1.83-1.93 (1H,m), 2.03-2.14 (1H,m), 2.37-2.46 (1H,m), 2.46-2.52 (1H,m), 2.60 (1H,dd,J=13.8,8.3 Hz), 3.00 (1H,dd, J=13.8,4.4 Hz), 3.47 (1H,dd,J=11.1,2.3 Hz), 3.54 (1H,dd, J=11.1,1.5 Hz), 3.70 (1H,dd,J=11.1,2.3 Hz), 3.88 (1H,d, J=11.1 Hz), 4.67 (1H,d,J=6.1 Hz), 4.97 (1H,d,J=6.1 Hz), 7.05 (2H,d,J=8.4 Hz), 7.23 (1H,d,J=8.4 Hz).

Production Example 23

Synthesis of 2-(4-chlorobenzyl)-1-(1H-1,2,4-triazole-1-ylmethyl)-7,9-dioxaspiro[4,5]decane-1-ol (azole derivative (V') which is Compound V'-d wherein $R^6$=H, $R^7$=H, $X_m$=4-Cl, A=N)

Synthesis was performed in the same way as Production Example 17 except that Compound VIII'-d was used instead of Compound VIII'-b, to thereby obtain Compound V'-d as an isomer mixture.

As to $^1$H-NMR values, only that of a cis isomer of Compound V'-d is described below.
$^1$H-NMR(400MHz,CDCl$_3$):δ=1.10-1.14 (1H,m), 1.36-1.45 (1H,m), 1.45-1.57 (2H,m), 1.93 (1H,dd,J=12.7,2.9 Hz), 2.27-2.35 (1H,m), 2.38 (1H,dd,J=12.7,10.9 Hz), 3.35 (1H,d,J=11.1 Hz), 3.54 (1H,d,J=12.3 Hz), 4.07 (1H,dd, J=12.3,2.3 Hz), 4.29 (1H,d,J=11.1,1.9 Hz), 4.50 (1H,d, J=14.3 Hz), 4.59 (1H,J=6.0 Hz), 4.74 (1H,d,J=14.3 Hz), 4.83 (1H,s), 4.87 (1H,d,J=6.0 Hz), 6.98 (2H,d,J=8.4 Hz), 7.19 (2H,d,J=8.4 Hz), 8.00 (1H,s), 8.23 (1H,s).

Production Example 24

Synthesis of 2-(4-chlorobenzyl)-8-methyl-7,9-dioxaspiro[4,5]decane-1-on (Compound VIII'-e which is Compound (VIII') wherein $R^6$=$CH_3$, $R^7$=H, $X_m$=4-Cl)

(1) Synthesis of methyl 2-(4-chlorobenzyl)-8-methyl-1-oxo-7,9-dioxaspiro[4,5]decane-2-carboxylate (Compound IX'-e which is Compound (IX') wherein $R^4$=$CH_3$, $R^6$=$CH_3$, $R^7$=H, $X_m$=4-Cl)

Compound X'-a (2.50 g) prepared in Production Example 11-(1) was dissolved in toluene (12.5 ml), and acetaldehyde diethyl acetal (2.72 ml) and p-toluenesulfonic acid monohydrate (72.8 mg) are added, and the resultant mixture was stirred at a room temperature for 3.5 hours. The mixture was further stirred at 60° C. for 2 hours, and was further stirred at 80° C. for 2 hours. After the reaction, the resultant reaction solution was concentrated until an amount of the reaction solution was reduced by half. An aqueous saturated sodium hydrogen carbonate was added, and extraction was performed with use of toluene. An organic layer of the extract was washed with a saturated brine solution, and was dried with use of anhydrous sodium sulfate. The solvent was concentrated, and was dried in vacuum. Thus Compound IX'-e was obtained (yield 89.2%).

$^1$H-NMR(400MHz,CDCl$_3$):δ=1.27 (3H,d,J=5.1 Hz), 1.95-2.04 (2H,m), 2.09-2.18 (1H,m), 2.32-2.41 (1H,m), 2.96 (1H,dd,J=11.1,2.7 Hz), 3.04 (1H,d,J=13.7 Hz), 3.20 (1H,d, J=13.7 Hz), 3.47 (1H,dd,J=11.1,1.3 Hz), 3.72 (3H,s), 3.78 (1H,dd,J=11.1,2.7 Hz), 3.84 (1H,d,J=11.1 Hz), 4.60 (1H,q, J=5.1 Hz), 7.00 (2H,d,J=8.5 Hz), 7.23 (2H,d,J=8.5 Hz).

(2) Synthesis of Compound VIII'-e

Toluene (0.234 ml) and a 0.5 mol/L sodium hydroxide aqueous solution (21.8 ml) were added to Compound IX'-e (2.34 g) in one-third portions every hour while the resultant mixture was being refluxed for 4 hours. A 6.25 mol/L sodium hydroxide aqueous solution (0.57 ml) was added, and the resultant mixture was further refluxed for 2 hours. After the reaction, extraction was performed with use of toluene. An organic layer of the extract was washed with a saturated brine solution, and was dried with use of anhydrous sodium sulfate. By distilling the solvent, Compound VIII'-e was obtained (yield 72.0%).

$^1$H-NMR(400MHz,CDC$_{13}$):δ=1.31 (3H,d, J=5.1 Hz), 1.49-1.61 (1H,m), 1.84-1.93 (1H,m), 2.05-2.14 (1H,m), 2.40-2.51 (2H,m), 2.59 (1H,dd,J=13.8, 8.3 Hz), 2.99 (1H,dd, J=13.8,4.4 Hz), 3.46 (1H,dd,J=11.1,2.8 Hz), 3.57 (1H,dd, J=11.1,1.8 Hz), 3.70 (1H,dd,J=11.1,2.8 Hz), 3.94 (1H,d, J=11.1 Hz), 4.66 (1H,q,J=5.1 Hz), 7.05 (2H,d,J=8.4 Hz), 7.23 (1H,d,J=8.4 Hz).

Production Example 25

Synthesis of 2-(4-chlorobenzyl)-8-methyl-1-(1H-1,2,4-triazole-1-ylmethyl)-7,9-dioxaspiro[4,5]decane-1-ol (azole derivative (V') which is Compound V'-e wherein $R^6$=CH$_3$, $R^7$=H, $X_m$=4-Cl, A=N)

Synthesis was performed in the same way as Production Example 17 except that Compound VIII'-e was used instead of Compound VIII'-b, to thereby obtain Compound V'-e as an isomer mixture.

As to $^1$H-NMR values, only that of a cis isomer of Compound V'-e is described below.

$^1$H-NMR(400MHz,CDCl$_3$):δ=1.03-1.10 (1H,m), 1.31 (3H,d,J=5.1 Hz), 1.35-1.41 (1H,m), 1.41.42-1.55 (3H,m), 2.17 (1H,dd,J=13.3,11.4 Hz), 2.30-2.39 (1H,m), 3.44 (1H,d, J=11.7 Hz), 3.58 (1H,d,J=12.5 Hz), 4.09 (1H,dd,J=12.5,2.9 Hz), 4.51 (1H,s), 4.56 (1H,dd J=11.7,2.9 Hz), 4.59 (1H,d, J=14.5 Hz), 4.67 (1H,q,J=5.1 Hz), 4.83 (1H,d,J=14.5 Hz), 6.91 (2H,d,J=8.4 Hz), 7.17 (2H,d,J=8.4 Hz), 8.02 (1H,s), 8.28 (1H,s).

Production Example 26

Synthesis of Compound IX'-a

Synthesis was performed in the same way as Production Example 8 except that the reaction temperature in Production Example 8 was changed to 95° C. (bath temperature).
Yield: 95.5%

In Test Examples 1 to 5 described below, Compounds (Compound No. I-16, I-170, I-187, I-226, I-234, I-198, and I-203) produced in Production Examples described above were used as compounds in accordance with the present invention. Further, a compound of Compound No. I-16 having an isomer type of CC is defined as "I-16a", whereas a compound of Compound No. I-16 having an isomer type of CT is defined as "I-16b". Meanwhile, in Test Examples 6 to 8, Compound V'-a produced in Production Examples described above was used as a compound in accordance with the present invention.

Formulation Example 1

| (Wettable formulation) | |
| --- | --- |
| Compound (I-16) | 50 parts |
| Lignin sulfonate salt | 5 parts |
| Alkyl sulfonate salt | 3 parts |
| Diatomaceous earth | 42 parts | are ground and mixed with each other, and is produced as a wettable formulation. The wettable formulation is used as being diluted with water.

| (Dust formulation) | |
| --- | --- |
| Compound (I-16) | 3 parts |
| Clay | 40 parts |
| Talc | 57 parts | are ground and mixed, and used as a dusting formulation.

| (Granule formulation) | |
| --- | --- |
| Compound (I-16) | 5 parts |
| Bentonite | 43 parts |
| Clay | 45 parts |
| Lignin sulfonate salt | 7 parts | are mixed uniformly, and water is added. The resultant mixture is kneaded and is processed by an extruding granulator. The resultant granules are dried and produced as a granule formulation.

| (Emulsifiable concentrate) | |
| --- | --- |
| Compound (I-16) | 20 parts |
| Polyoxyethylene alkylaryl ether | 10 parts |
| Polyoxyethylene sorbitan monolaurate | 3 parts |
| Xylene | 67 parts | are mixed and dissolved uniformly to obtain an emulsifiable concentrate.

Formulation Example 2

A cis isomer and a trans isomer of Compound V'-a thus synthesized were used to prepare a wettable formulation, a dust formulation, a granule formulation, and an emulsion formulation. Hereinafter, the cis isomer of Compound V'-a is represented by "Compound V'-a-cis", and the trans isomer of Compound V'-a is represented by "Compound V'-a-trans". For the sake of easy explanation, only combinations with use of Compound V'-a-cis is described below, however, Compound V'-a-trans was prepared in the same combination. Note that the term "part(s)" in Formulation Examples represents weight by parts.

| (Wettable formulation) | |
|---|---|
| Compound V'-a-cis | 50 parts |
| Lignin sulfonate salt | 5 parts |
| Alkyl sulfonate salt | 3 parts |
| Diatomaceous earth | 42 parts | were ground and mixed to form a wettable formulation, and the wettable formulation was used as being diluted with water.

| (Powder formulation) | |
|---|---|
| Compound V'-a-cis | 3 parts |
| Clay | 40 parts |
| Talc | 57 parts | were ground and mixed, and used as a dusting formulation.

| (Granule formulation) | |
|---|---|
| Compound V'-a-cis | 5 parts |
| Bentonite | 43 parts |
| Clay | 45 parts |
| Lignin sulfonate salt | 7 parts | were mixed uniformly, and water was added. The resultant mixture was kneaded and was processed by an extruding granulator. The resultant granules were dried and produced as a granule formulation.

| (Emulsion formulation) | |
|---|---|
| Compound V'-a-cis | 20 parts |
| Polyoxyethylene alkylaryl ether | 10 parts |
| Polyoxyethylene sorbitan monolaurate | 3 parts |
| Xylene | 67 parts | were mixed and dissolved uniformly to obtain an emulsion formulation.

Test Example 1

Test for Anti-Bacterial Effect on Wheat Leaf Blight-Causing Microorganisms

In Test Examples, an anti-bacterial effect of a compound in accordance with the present invention on the wheat leaf blight-causing microorganisms was tested, and was compared with the anti-bacterial effect of a comparative compound (1).

Comparative compound (1): (1RS,5SR)-5-(4-chlorobenzyl)-2-methyl-2-methylethoxymethyl-1-(1H-1,2,4-triazole-1-ylmethyl)cyclopentanol

[Chem. 35]

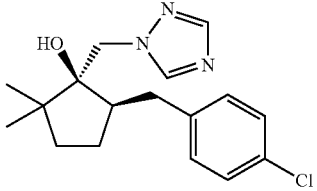

(1)

A dimethyl sulfoxide solution (0.6 ml) containing a compound in accordance with the present invention was added to a PDA medium (potato dextrose agar medium) (60 ml) having about 60° C., and the resultant mixture was mixed thoroughly in a 100-ml conical flask. The mixture was poured into a dish, and was solidified. Thus a plate medium containing the compound of the present invention at a concentration of 1.25 g/L was obtained.

On the other hand, a subject microorganism previously cultured on a plate medium was cut out with use of a cork borer whose diameter was 4 mm, and the wheat leaf blight-causing microorganism on the plate medium thus cut out was inoculated to the chemical-containing plate medium described above. After such inoculation, the chemical-containing plate medium was incubated at 25° C. for 14 days, and then diameters of its flora were measured. A % mycelial growth inhibition was calculated with use of the formula.

$R=100(dc-dt)/dc$ (where R=% mycelial extension inhibition, dc=flora diameter in untreated plate, dt=flora diameter in treated plate)

The results obtained as described above were evaluated on a five-point scale according to the following criteria.

<Growth Inhibition Grade>
5: % Mycerial growth inhibition of 80% or higher
4: % Mycerial growth inhibition of less than 80 to 60% or higher
3: % Mycerial growth inhibition of less than 60 to 40% or higher
2: % Mycerial growth inhibition of less than 40 to 20% or higher
1: % Mycerial growth inhibition of less than 20%

TABLE 1

| Compound Number | Concentration (mg/L) | Growth inhibition grade |
|---|---|---|
| 1-16a | 1.25 | 5 |
| 1-170 | 1.25 | 5 |
| 1-187 | 1.25 | 5 |
| 1-226 | 1.25 | 5 |
| 1-234 | 1.25 | 5 |
| 1-198 | 1.25 | 5 |
| 1-203 | 1.25 | 4 |
| V'-a-cis | 1.25 | 5 |
| V'-e | 1.25 | 5 |
| Compound (1) | 1.25 | 4 |

Test Example 2

Test for Examining Controlling Effect on Wheat Brown Rust

Onto a wheat plant (cultivar: NORIN No. 61) grown to the two-leaf stage with use of a square plastic pot (6 cm×6 cm), a wettable formulation such as Formulation Example 1 which was diluted and suspended in water at a concentration of 1 mg/L was sprayed at a rate of 1,000 L/ha. The sprayed leaves were air-dried, and inoculated with spore suspension of wheat-brown-rust-causing microorganisms (adjusted at 200 spores/vision, Gramin S was added at 60 ppm) by spraying, and kept at 25° C. and a high humidity for 48 hours. Thereafter, the plant was kept in a greenhouse. Nine to fourteen days after inoculation, the wheat brown rust lesion degree was evaluated. Nine to fourteen days after inoculation, the wheat brown rust lesion degree was evaluated. The protective value was calculated by the following equation.

Protective value (%)=(1−mean lesion degree in sprayed plot/mean lesion degree in unsprayed plot)×100

TABLE 2

| Lesion degree | % Area of onset |
|---|---|
| 0 | No onset |
| 0.5 | Less than 1% |
| 1 | 1% or more but Less than 5% |
| 2 | 5% or more but Less than 10% |
| 3 | 10% or more but Less than 30% |
| 4 | 30% or more but Less than 50% |
| 5 | 50% or more |

TABLE 3

Wheat brown rust lesion protective index

| | Protective value |
|---|---|
| 1 | 0 to 20 |
| 2 | 21 to 40 |
| 3 | 41 to 60 |
| 4 | 61 to 80 |
| 5 | 81 to 100 |

TABLE 4

| Compound Number | Concentration (mg/L) | Protective value |
|---|---|---|
| 1-16a | 1 | 4 |
| 1-170 | 1 | 4 |
| 1-187 | 1 | 4 |
| 1-226 | 1 | 4 |
| 1-234 | 1 | 4 |
| 1-198 | 1 | 4 |
| 1-203 | 1 | 4 |
| V'-d | 1 | 4 |
| Compound (1) | 1 | 3 |

Test Example 3

Test for Anti-Bacterial Effect on Various Pathogenic Microorganism and Hazardous Microorganisms In this Test Example, a plate medium containing a compound of the present invention was formed at a concentration of 5 mg/L or 1.25 mg/L, and the anti-bacterial effects of the compounds of the present invention on various phytopathogenic fungi for plants and hazardous microorganism for industrial materials were examined by the method described in Test Example 1.

The results obtained as described above were evaluated on a five-point scale according to the following criteria.

<Growth Inhibition Grade>

5: % Mycerial growth inhibition of 80% or higher
4: % Mycerial growth inhibition of less than 80 to 60% or higher
3: % Mycerial growth inhibition of less than 60 to 40% or higher
2: % Mycerial growth inhibition of less than 40 to 20% or higher
1: % Mycerial growth inhibition of less than 20%

TABLE 5

| Compound Number | Concentration (mg/L) | P.n | P.h | F.g | U.n | P.o | G.f | A.m | S.s | B.c | F.c | R. sec | M.n | R.o |
|---|---|---|---|---|---|---|---|---|---|---|---|---|---|---|
| 1-16a | 5 | 5 | 5 | 5 | 5 | 5 | 5 | 5 | 5 | 5 | 5 | 5 | 5 | 5 |
| | 1.25 | 5 | 4 | 5 | 5 | 5 | 5 | 4 | 5 | 5 | 5 | 5 | 5 | 5 |
| 1-170 | 5 | 5 | 5 | 5 | 5 | 5 | 5 | 5 | 5 | 5 | 5 | 5 | 5 | 5 |
| | 1.25 | 5 | 5 | 5 | 5 | 5 | 5 | 4 | 5 | 5 | 5 | 5 | 5 | 5 |
| 1-187 | 5 | 5 | 5 | 5 | 5 | 5 | 5 | 5 | 5 | 5 | 5 | 5 | 5 | 5 |
| | 1.25 | 4 | 5 | 5 | 5 | 5 | 5 | 4 | 5 | 5 | 5 | 5 | 5 | 5 |
| 1-226 | 5 | 5 | 5 | 5 | 5 | 5 | 5 | 5 | 5 | 5 | 5 | 5 | 5 | 5 |
| | 1.25 | 5 | 4 | 5 | 5 | 5 | 5 | 4 | 5 | 5 | 5 | 5 | 5 | 5 |
| 1-234 | 5 | 5 | 5 | 5 | 5 | 5 | 5 | 5 | 5 | 5 | 5 | 5 | 5 | 5 |
| | 1.25 | 5 | 4 | 5 | 5 | 5 | 5 | 4 | 5 | 5 | 5 | 5 | 5 | 5 |
| 1-198 | 5 | 5 | 5 | 5 | 5 | 5 | 5 | 5 | 5 | 5 | 5 | 5 | 5 | 5 |
| | 1.25 | 4 | 4 | 4 | 4 | 5 | 5 | 4 | 5 | 5 | 5 | 5 | 4 | 5 |
| 1-203 | 5 | 5 | 5 | 5 | 5 | 5 | 5 | 5 | 5 | 5 | 5 | 5 | 5 | 5 |
| | 1.25 | 4 | 4 | 5 | 5 | 5 | 5 | 4 | 5 | 5 | 5 | 5 | 5 | 4 |
| 1-16b | 5 | — | — | — | — | — | — | — | — | — | — | — | 5 | 5 |
| | 1.25 | — | — | — | — | — | — | — | — | — | — | — | 3 | 5 |
| Compound (1) | 5 | — | — | — | — | — | — | — | — | — | — | — | 5 | 5 |
| | 1.25 | — | — | — | — | — | — | — | — | — | — | — | 2 | 4 |

Wheat *Septoria nodorum* blotch microorganism (*Phaeosphaeria nodorum*) P.n
Wheat eye spot (*Pseudocercoporella herpotrichoides*) P.h
Wheat *fusarium* blight (*Fusarium graminearum*) F.g
Barley loose smut (*Ustilago nuda*) U.n
Rice blast (*Pyricularia oryzae*) P.o
Rice bakanae disease (*Giberella fujikuroi*) G.f
*Alternaria* blotch (*Alternaria alternata*) A.m
*Sclerotinia* rot (*Sclerotinia sclerotiorum*) S.s
Gray mold (*Botritis cinerea*) B.c
Cucumber *fusarium* wilt (*Fusarium oxysporum*) F.c
Barley leaf blotch (*Rhynchosporium secalis*) R. sec
Wheat pink snow mold (*Microdochium nivale*) M.n
Rice bacterial seeding blight (*Rhizopus oryzae*) R.o

Test Example 4

Test for Examining Controlling Effect on Wheat Brown Rust Caused by Seed Treatment An efficacy against wheat brown rust was evaluated by performing a pot test. Compounds (2 mg) of the present invention and a comparative compound (2 mg) were weighed, and those compounds were each dissolved in DMSO (18 μl). Chemicals thus prepared were applied to wheat seeds (1 g) in a vial, and eight wheat seeds were seeded in a pot of 80 cm$^2$. The pots were kept in a greenhouse with supplying water underneath. Twenty one days after the seeding, wheat brown rust-causing microorganisms was inoculated, and the pots were stored in a humidity chamber for 2 days. The pots were kept again in a greenhouse with supplying water underneath. Fourteen days after the inoculation, a lesion degree was evaluated, and a protective value was calculated.

The protective value was calculated with use of the following formula, and was defined as a wheat brown rust protective value.

Protective value=(1−lesion degree in treated plot/lesion degree in untreated plot)×100(%)

As a result, Compound I-16a, Compound V'-d, and Compound V'-e have a protective value of 100, and Compound (1) has a protective value of 95.

Test Example 5

Growth Inhibition Test for Wheat Caused by Seed Treatment

Harmful effect (growth inhibition) to wheat was evaluated by performing a pot test. Compounds (2 mg) of the present invention and a comparative compound (2 mg) were weighed, and those compounds were each dissolved in DMSO (18 μl). Chemical thus prepared were applied to wheat seeds (1 g) in a vial, and eight wheat seeds were seeded in a pot of 80 cm$^2$. The seeds were cultivated in a greenhouse with supplying water underneath. 36 days after the seeding, damage (growth inhibition) was evaluated.

As a result, a damage index was 2 in the case of treating seeds with Compound (1), whereas the damage index was 4 in the case of using Compound I-16a, Compound V'-d, Compound V'-e, Compound V'-a-cis, or Compound V'-a-trans.

The damage (growth inhibition) index was calculated on the basis of the following table. As the growth inhibition index becomes larger, the damage of growth inhibition caused by the treatment of the chemicals becomes smaller.

TABLE 6

| Growth degree (with respect to untreated plot) | Harmful effect index (growth inhibition) |
| --- | --- |
| 80% or more | 0 |
| Less than 80% but 60% or more | 1 |
| Less than 60% but 40% or more | 2 |
| Less than 40% but 20% or more | 3 |
| Less than 20% but 1% or more | 4 |
| No growth inhibition | 5 |

Test Example 6

Harmful Effect of Necrosis to Wheat Seeds Caused by Seed Treatment

Harmful effect (growth inhibition) to wheat was evaluated by performing a pot chemicals (2 mg) of the present invention and a comparative compound (2 mg) were weighed, and those compounds were each dissolved in DMSO (18 μl). Chemicals thus prepared were applied to wheat seeds (1 g) in a vial, and eight wheat seeds were seeded in a pot of 80 cm$^2$. The seeds were cultivated in a greenhouse with supplying water underneath. Thirty one days after the seeding, a degree of necrosis (necrosis area ratio) in wheat was evaluated. By using criteria shown in Table 7, necrosis indexes were calculated on the basis of the necrosis area ratio.

As a result, the necrosis index was 1 in the case of using Compound (1), whereas the necrosis index was 0 in the case of using Compound V'-d, V'-e, V'-a-cis, or Compound V'-a-trans. Note that, as the necrosis indexes become smaller, the harmful effect of the necrosis caused by treatment of the chemicals becomes smaller.

TABLE 7

| Necrosis area rate | Necrosis index |
| --- | --- |
| Less than 1% | 0 |
| 1% or more but less than 5% | 1 |
| 5% or more but less than 20% | 2 |
| 20% or more | 3 |

Test Example 7

Test for Examining Controlling Effect on Wheat Brown Rust

Compound V'-a-cis or Compound V'-e in the form of a wettable formulation shown in Formulation Example 2 was diluted and suspended in water at a concentration of 100 mg/L, and was sprayed at a rate of 1,000 L/ha onto a wheat plant (variety: NORIN No. 61) grown to the two-leaf phase with use of a square plastic pot (6 cm×6 cm). The sprayed leaves were air-dried, and inoculated with spore suspension of *Puccinia recondita*-causing microorganisms (adjusted at 200 spores/vision, Gramin S was added at 60 ppm) by spraying, and kept at 25° C. and a high humidity for 48 hours. Thereafter, the plant was kept in a greenhouse. Nine to fourteen days after inoculation, the wheat brown rust lesion degree was evaluated, and the protective value was calculated in the same way as Test Example 2.

As a result of the test, the protective values of Compound V'-a-cis and Compound V'-e were 90% or more.

Test Example 8

Test for Anti-Bacterial Effect on Various Pathogenic Microorganisms and Hazardous Microorganisms In this Test Example, the anti-bacterial effects of Compound V'-d, compound V'-e, Compound V'-a-cis, and Compound V'-a-trans on various pathogenic microorganism were tested.

Compound V'-d, Compound V'-e, Compound V'-a-cis, and Compound V'-a-trans were each dissolved in dimethyl sulfoxide (2 ml). Each (0.6 ml) of these solutions was added to a PDA medium (potato dextrose agar medium) (60 ml) at about 60° C., and the resultant mixture was mixed thoroughly in a 100-ml conical flask, was poured into a dish, and was solidified. Thus plate mediums containing Compound V'-d, Compound V'-e, Compound V'-a-cis, and Compound V'-a-trans, respectively, are formed at 5 mg/L.

On the other hand, subject microorganisms previously cultured on plate mediums were cut out using a cork borer whose diameter was 4 mm, and were inoculated to the chemical-containing plate mediums described above. After inoculation, the dishes was grown at the optimum growth temperatures for respective microorganisms (for this growth temperature, see, for example, a reference LIST OF CULTURES 1996 microorganisms 10th edition, Institute for Fermentation (foundation)) for 1 to 14 days, and the mycelial growth was measured as a diameter of its flora. The growth degree of the microorganisms on the chemical-containing plate mediums thus observed was compared with the growth degree of the microorganism in the untreated group, and % mycelial growth inhibition was calculated in the same way as Test Example 1. Results of the test were evaluated on a five-point scale in the same way as Test Example 1. The results are shown in Table 8.

TABLE 8

| Compound | Anti-bacterial effect index against various microorganisms | | | | | | | |
|---|---|---|---|---|---|---|---|---|
| | P.n | G.g | P.g | P.o | S.t | R. sec | M.n | R.o |
| V'-a-cis | 5 | 5 | 5 | 5 | 5 | 5 | 5 | 5 |
| V'-a-trans | 5 | 5 | 5 | 5 | 5 | 5 | 5 | 5 |
| V'-d | 5 | 5 | 5 | 5 | 4 | 5 | 3 | 5 |
| V'-e | 5 | 5 | 5 | 5 | 5 | 5 | 5 | 5 |

P.n: Wheat *Septoria nodorum* blotch microorganism (*Phaeosphaeria nodorum*)
G.g:
P.g: Barley stripe (*Pyrenophora graminea*)
P.o: Rice blast (*Pyricularia oryzae*)
S.t: Wheat leaf blight (*Septoria tritici*)
R. sec: Barley leaf blotch (*Rhynchosporium secalis*)
M.n: Snow mold of winter wheat (*Microdochium nivale*)
R.o: Swollen rice seedling (*Rhizopus oryzae*)

Industrial Applicability

The present invention can be preferably used for producing a compound which can be used as an active constitutent of bactericides for an agro-horticultural agent.

The invention claimed is:

1. An azole derivative represented by the following general formula (V'):

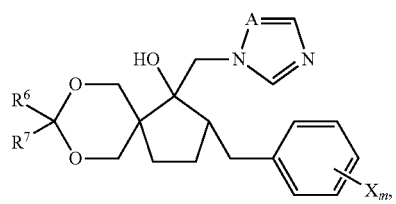

wherein R6 and R7 independently represent a hydrogen atom, a C1-C4 alkyl group, a phenyl group, or a benzyl group, and one or more hydrogen atoms of the phenyl group and one or more hydrogen atoms in a phenyl part of the benzyl group may be substituted with a C1-C4 alkyl group, a C1-C4 alkoxy group, or a halogen atom; X represents a halogen atom, a C1-C4 alkyl group, a C1-C4 haloalkyl group, a C1-C4 alkoxy group, a C1-C4 haloalkoxy group, a phenyl group, a cyano group, or a nitro group; m represents an integer of 0 to 5, and a plurality of Xs may be different from each other in the case where m is 2 or more; and A represents a nitrogen atom or a methyne group.

2. A method for producing the azole derivative recited in claim 1, comprising the step of:

reacting a compound represented by the following general formula (VII'), which compound has been obtained by converting a compound represented by the following general formula (VIII') into an oxirane, with a compound represented by the following general formula (VI) in order to obtain an azole derivative represented by the general formula (V'):

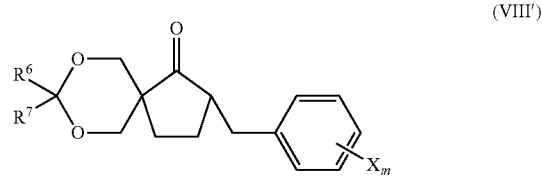

wherein R6, R7, X, and m in the formula (VIII') are identical with those in the formula (V'), respectively;

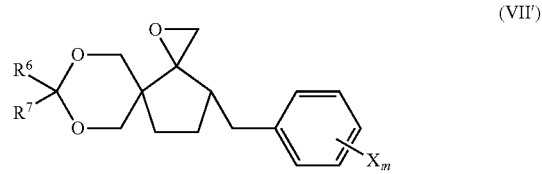

wherein R6, R7, X, and m in the formula (VII') are identical with those in the formula (V'), respectively;

wherein M represents a hydrogen atom or an alkalin metal, and A in the formula (VI) is identical with that in the formula (V').

3. A method as set forth in claim 2, further comprising the step of:

reacting a compound represented by the following general formula (IX') in the presence of a base, in order to obtain the compound represented by general formula (VIII'):

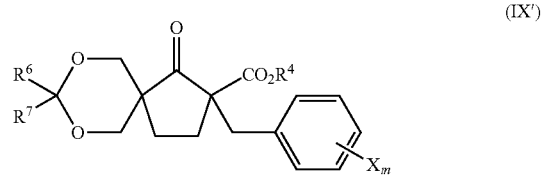

wherein R6, R7, X, and m in the formula (IX') are identical with those in the formula (V'), respectively, and R4 represents a C1-C4 alkyl group.

4. A method as set forth in claim 3, further comprising the step of:

reacting a compound represented by the following general formula (X') with an acetal represented by the following general formula (XIV) or with a ketone represented by the following general formula (XV) in the presence of an acid, in order to obtain the compound represented by the general formula (IX'):

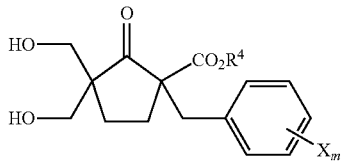
(X')

wherein X and m in the formula (X') are identical with those in the formula (V'), respectively, and R4 in the formula (X') is identical with that in the formula (IX');

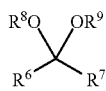
(XIV)

wherein R6 and R7 in the formula (XIV) are identical with those in the formula (V'), respectively, and R8 and R9 independently represent a C1-C4 alkyl group;

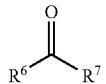
(XV)

wherein R6 and R7 in the formula (XV) are identical with those in the formula (V'), respectively.

5. A method for producing an azole derivative represented by the following general formula (IV'), comprising the step of:
reacting the azole derivative recited in claim 1 in the presence of an acid, in order to obtain the azole derivative represented by the following general formula (IV'):

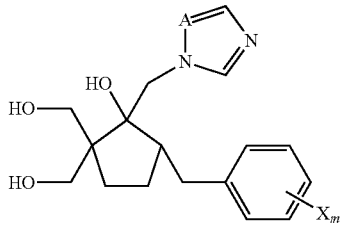
(IV')

wherein X, m, and A in the formula (IV') are identical with those in the formula (V'), respectively.

6. A method as set forth in claim 5, further comprising:
the step of reacting a compound represented by the following general formula (VII'), which compound has been obtained by converting a compound represented by the following general formula (VIII') into an oxirane, with a compound represented by the following general formula (VI) in order to obtain an azole derivative represented by the general formula (V'):

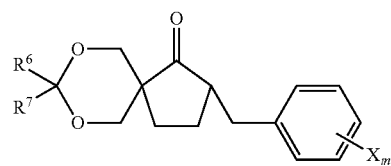
(VIII')

wherein $R^6$, $R^7$, X, and m in the formula (VIII') are identical with those in the formula (V'), respectively;

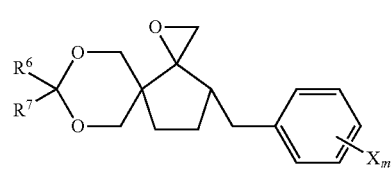
(VII')

wherein $R^6$, $R^7$, X, and m in the formula (VII') are identical with those in the formula (V'), respectively;

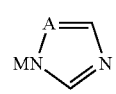
(VI)

wherein M represents a hydrogen atom or an alkalin metal, and A in the formula (VI) is identical with that in the formula (V').

7. The method as set forth in claim 2, wherein $R^6$ and $R^7$ independently represent a $C_1$-$C_4$ alkyl group.

8. An intermediate compound represented by the following general formula (VIII'), the intermediate compound being used for producing the azole derivative recited in claim 1:

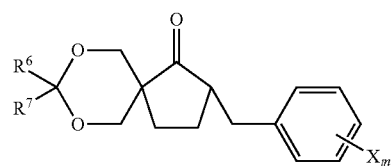
(VIII')

wherein $R^6$, $R^7$, X, and m in the formula (VIII') are identical with those in the formula (V'), respectively.

9. An intermediate compound represented by the following general formula (IX'), the intermediate compound being used for producing the azole derivative recited in claim 1:

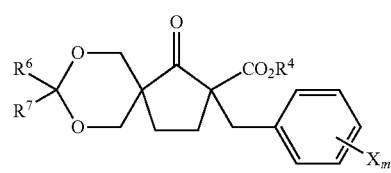
(IX')

wherein $R^6$, $R^7$, X, and m in the formula (IX') are identical with those in the formula (V'), respectively, and $R^4$ represents a $C_1$-$C_4$ alkyl group.

10. An azole derivative represented by the following general formula (Ia'), the azole derivative being produced by a method recited in claim 2:

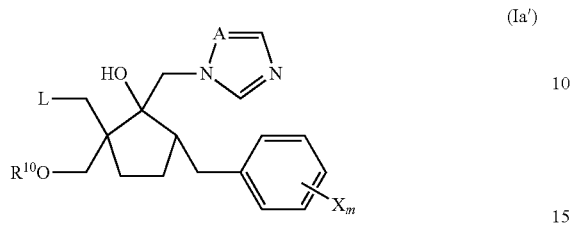

wherein $R^{10}$ represents a $C_1$-$C_3$ alkyl group, L represents a halogen atom, and X, m, A in the formula (Ia') are identical with those in the formula (V'), respectively.

11. An agro-horticultural agent containing the azole derivative recited in claim 1 as an active constituent, the agro-horticultural agent being used in a seed treatment.

12. A seed treated by the agro-horticultural agent recited in claim 11.

13. The method as set forth in claim 5, wherein $R^6$ and $R^7$ independently represent a $C_1$-$C_4$ alkyl group.

* * * * *